United States Patent [19]
Dooley et al.

[11] Patent Number: 5,641,861
[45] Date of Patent: Jun. 24, 1997

[54] μOPIOID RECEPTOR LIGANDS: AGONISTS AND ANTAGONISTS

[75] Inventors: Colette T. Dooley, San Diego; Richard A. Houghten, Del Mar, both of Calif.

[73] Assignee: Torrey Pines Institute For Molecular Studies, San Diego, Calif.

[21] Appl. No.: 487,006

[22] Filed: Jun. 7, 1995

[51] Int. Cl.$^6$ .......................... A61K 38/08; A61K 38/04
[52] U.S. Cl. .................................................... 530/329
[58] Field of Search ............................................. 530/329

[56] References Cited

U.S. PATENT DOCUMENTS 5,367,053  11/1994  Dooley et al. .................... 530/329

OTHER PUBLICATIONS

Blondelle et al., "Soluble combinatorial libraries of organic peptidomimetic and peptide diversities." *Trends in Analytical Chem.*, 14(2):83–92 (1995).

Schiller Peter W., "Development of receptor-specific opioid peptide analogues." *Progress in Medicinal Chem.*, 28:301–340 (1991).

Dooley et al., "Identification of tetrameric opioid peptides from a combinatorial library composed of L–, D– and non-proteinogenic amino acids." In H.L.S. Maia (Ed), Peptides 94: Proceedings of the 23rd European Peptide Symposium. Escom, Leides (1995).

Houghten and Dooley, "The use of synthetic peptide combinatorial libraries for the determination of peptide ligands in radio–receptor assays: opioid peptides." *BioMed. Chem Lett.*, 3:405–412 (1993).

Hruby and Gehrig, "Recent developments in the design of receptor specific opioid peptides." *Medicinal Res. Rev.*, 9(3):343–401 (1989).

Dooley et al., "Acetalins: opioid receptor antagonists determined through the use of synthetic peptide combinatorial libraries." *Proc. Natl. Acad. Sci. USA*, 90:10811–10815 (1993).

Dooley et al., "An all D–Amino acid opioid peptide with central analgesic activity from a combinatorial library." *Science*, 266:2019–2022.

Dooley et al., "Rapid identification of novel opioid peptides from an N–acetylated synthetic combinatorial library." *Regulatory Peptides*, 54:87–88 (1994).

Ostresh et al., "Libraries from libraries: Chemical transformation of combinatorial libraries to extend the range and repertoire of chemical diversity." *Proc. Natl. Acad. Sci. USA*, 91:11138–11142 (1994).

Dooley and Houghten, "The use of positional scanning synthetic peptide combinatorial libraries for the rapid determination of opioid receptor ligands." *Life Science*, 52:1509–1517 (1993).

Erchegyi et al., "Isolation of a novel tetrapeptide with opiate and antiopiate activity from human brain cortex": Tyr–Pro––Trp–Gly–NH$_2$ (Tyr–W–MIF–1) *Peptides*, 13:623–631 (1992).

Schiller et al., "Unsulfated C–terminal 7–peptide of cholecystokinin: a new ligand of the opiate receptor." *Biochem. and Biophys. Res. Comm.*, 85(4):1332–1338 (1978).

*Primary Examiner*—Edward J. Cain
*Attorney, Agent, or Firm*—Campbell & Flores, LLP

[57] ABSTRACT

The present invention provides novel opioid peptides. Disclosed are opioid peptides having the general structures Ac-Phe-Arg-Trp-Trp-Tyr-Xaa—NH$_2$ (SEQ ID NO. 1); Ac-Arg-Trp-Ile-Gly-Trp-Xaa—NH$_2$ (SEQ ID NO. 2); Trp-Trp-Pro-Lys-His-Xaa—NH$_2$ (SEQ ID NO. 3); and shorter versions of the latter, namely, Trp-Trp-Pro-Xaa—NH$_2$ (SEQ ID NO. 4); Tyr-Pro-Phe-Gly-Phe-Xaa—NH$_2$ (SEQ ID NO. 5); (D)Ile-(D)Met-(D)Ser-(D)Trp-(D)Trp-Gly$_n$-Xaa—NH$_2$ (SEQ ID NO. 6); and (D)Ile-(D)Met-(D)Thr-(D)Trp-Gly-Xaa—NH$_2$ (SEQ ID NO. 7). Within each genus, Xaa is substituted by a specific amino acid. The invention also relates to an opioid peptide having the general structure Tyr-A1-B2-C3—NH$_2$ (SEQ ID NO. 214), wherein A is D-Nve or D-Nle, B is Gly, Phe, or Trp, and C is Trp or Nap. Also included within the invention are opioid peptides of the general structure Pm and red {Me$_x$H$_y$N-Tyr-(NMe)$_z$-Tyr-Xaa$_z$—NH$_2$} (SEQ ID NO. 221), wherein Xaa is substituted by a specific amino acid.

10 Claims, 7 Drawing Sheets

162

165

163

166

164

167

168

171

169

172

170

173

174

177

175

178

176

179

180

183

181

184

182

185

186

189

187

190

188

191

192

195

193

196

194

197

198

201

199

202

200

203

SEQUENCE LISTING ( 1 ) GENERAL INFORMATION:

( i i i ) NUMBER OF SEQUENCES: 222

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( i x ) FEATURE:
        ( A ) NAME/KEY: Peptide
        ( B ) LOCATION: 6
        ( D ) OTHER INFORMATION: /note= "Xaa is any one of twenty naturally occurring amino acids."

( x i ) SEQUENCE DESCRIPTION: SEQ ID NO:1:

Phe  Arg  Trp  Trp  Tyr  Xaa
    1                           5

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( i x ) FEATURE:
        ( A ) NAME/KEY: Peptide
        ( B ) LOCATION: 6
        ( D ) OTHER INFORMATION: /note= "Xaa is any one of twenty naturally occurring amino acids."

( x i ) SEQUENCE DESCRIPTION: SEQ ID NO:2:

Arg  Trp  Ile  Gly  Trp  Xaa
    1                            5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at the C- terminal."

( i x ) FEATURE:
        ( A ) NAME/KEY: Peptide
        ( B ) LOCATION: 6
        ( D ) OTHER INFORMATION: /note= "Xaa is any one of twenty naturally occurring amino acids."

( x i ) SEQUENCE DESCRIPTION: SEQ ID NO:3:

Trp  Trp  Pro  Lys  His  Xaa
    1                            5

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 4
        ( D ) OTHER INFORMATION: /note= "Xaa is Lys or Arg."

( i x ) FEATURE:
        ( A ) NAME/KEY: Peptide
        ( B ) LOCATION: 4
        ( D ) OTHER INFORMATION: /note= "Amino acid is amidated at the C- terminal."

( x i ) SEQUENCE DESCRIPTION: SEQ ID NO:4:

Trp  Trp  Pro  Xaa
    1

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at
            the C- terminal."

( i x ) FEATURE:
        ( A ) NAME/KEY: Peptide
        ( B ) LOCATION: 6
        ( D ) OTHER INFORMATION: /note= "Xaa is any one of twenty
            naturally occurring amino acids."

( x i ) SEQUENCE DESCRIPTION: SEQ ID NO:5:

```
Tyr  Pro  Phe  Gly  Phe  Xaa
1                   5
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( D ) TOPOLOGY: linear ( i x ) FEATURE:
        ( A ) NAME/KEY: Peptide
        ( B ) LOCATION: 1..5
        ( D ) OTHER INFORMATION: /note= "These are the D-form of the
            amino acid."

( i x ) FEATURE:
        ( A ) NAME/KEY: Peptide
        ( B ) LOCATION: 6
        ( D ) OTHER INFORMATION: /note= "Peptides of this formula
            can be hexapeptides when Gly is absent or
            heptapeptides when Gly is present."

( i x ) FEATURE:
        ( A ) NAME/KEY: Peptide
        ( B ) LOCATION: 7
        ( D ) OTHER INFORMATION: /note= "Xaa is Gly or the D-form of
            a naturally- occurring amino acid"

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:6:

```
Ile  Met  Ser  Trp  Trp  Gly  Xaa
1                   5
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..4
        ( D ) OTHER INFORMATION: /note= "These are the D-form of the
            amino acids."

( i x ) FEATURE:
        ( A ) NAME/KEY: Peptide
        ( B ) LOCATION: 6
        ( D ) OTHER INFORMATION: /note= "Xaa is Gly or the D-form of a naturally- occurring amino acid."

( i x ) FEATURE:
    ( A ) NAME/KEY: Peptide
    ( B ) LOCATION: 6
    ( D ) OTHER INFORMATION: /note= "Amino acid is amidated at
        the C- terminal."

( x i ) SEQUENCE DESCRIPTION: SEQ ID NO:7:

```
Ile  Met  Thr  Trp  Gly  Xaa
1                   5
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:8:

```
Phe  Arg  Trp  Trp  Tyr  Met
1                   5
```

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:9:

```
Phe  Arg  Trp  Trp  Tyr  Leu
1                   5
```

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6

(D) OTHER INFORMATION: /note= "Amino acid is amidated at the C- terminal."

(x i) SEQUENCE DESCRIPTION: SEQ ID NO:10:

Phe Arg Trp Trp Tyr Ser
1               5

(2) INFORMATION FOR SEQ ID NO:11:

(i) SEQUENCE CHARACTERISTICS:
    (A) LENGTH: 6 amino acids
    (B) TYPE: amino acid
    (D) TOPOLOGY: linear (i x) FEATURE:
    (A) NAME/KEY: Peptide
    (B) LOCATION: 1
    (D) OTHER INFORMATION: /note= "Amino acid is acetylated at the N- terminal."

(i x) FEATURE:
    (A) NAME/KEY: Peptide
    (B) LOCATION: 6
    (D) OTHER INFORMATION: /note= "Amino acid is amidated at the C- terminal."

(x i) SEQUENCE DESCRIPTION: SEQ ID NO:11:

Phe Arg Trp Trp Tyr Ala
1               5

(2) INFORMATION FOR SEQ ID NO:12:

(i) SEQUENCE CHARACTERISTICS:
    (A) LENGTH: 6 amino acids
    (B) TYPE: amino acid
    (D) TOPOLOGY: linear (i x) FEATURE:
    (A) NAME/KEY: Peptide
    (B) LOCATION: 1
    (D) OTHER INFORMATION: /note= "Amino acid is acetylated at the N- terminal."

(i x) FEATURE:
    (A) NAME/KEY: Peptide
    (B) LOCATION: 6
    (D) OTHER INFORMATION: /note= "Amino acid is amidated at the C- terminal."

(x i) SEQUENCE DESCRIPTION: SEQ ID NO:12:

Phe Arg Trp Trp Tyr Ile
1               5

(2) INFORMATION FOR SEQ ID NO:13:

(i) SEQUENCE CHARACTERISTICS:
    (A) LENGTH: 6 amino acids
    (B) TYPE: amino acid
    (D) TOPOLOGY: linear (i x) FEATURE:
    (A) NAME/KEY: Peptide
    (B) LOCATION: 1
    (D) OTHER INFORMATION: /note= "Amino acid is acetylated at the N- terminal."

(i x) FEATURE:
    (A) NAME/KEY: Peptide
    (B) LOCATION: 6
    (D) OTHER INFORMATION: /note= "Amino acid is amidated at the C- terminal."

(x i) SEQUENCE DESCRIPTION: SEQ ID NO:13:

```
     Phe  Arg  Trp  Trp  Tyr  Thr
     1                  5
```

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note= "Amino acid is acetylated at the N- terminal."

(ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:14:

```
     Phe  Arg  Trp  Trp  Tyr  Val
     1                  5
```

(2) INFORMATION FOR SEQ ID NO:15:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note= "Amino acid is acetylated at the N- terminal."

(ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:15:

```
     Phe  Arg  Trp  Trp  Tyr  Gly
     1                  5
```

(2) INFORMATION FOR SEQ ID NO:16:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note= "Amino acid is acetylated at the N- terminal."

(ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:16:

```
     Phe  Arg  Trp  Trp  Tyr  Phe
     1                  5
```

(2) INFORMATION FOR SEQ ID NO:17:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:17:

Phe Arg Trp Trp Tyr Arg
1                   5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:18:

Phe Arg Trp Trp Tyr Lys
1                   5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:19:

Phe Arg Trp Trp Tyr Gln
1                   5

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at
        the N- terminal."

( i x ) FEATURE:
    ( A ) NAME/KEY: Peptide
    ( B ) LOCATION: 6
    ( D ) OTHER INFORMATION: /note= "Amino acid is amidated at
        the C- terminal."

( x i ) SEQUENCE DESCRIPTION: SEQ ID NO:20:

Phe Arg Trp Trp Tyr Tyr
1               5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:21:

Phe Arg Trp Trp Tyr His
1               5

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:22:

Phe Arg Trp Trp Tyr Trp
1               5

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Amino acid is amidated at
        the C- terminal."

( x i ) SEQUENCE DESCRIPTION: SEQ ID NO:23:

Phe Arg Trp Trp Tyr Cys
1               5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:24:

Phe Arg Trp Trp Tyr Asn
1               5

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:25:

Phe Arg Trp Trp Tyr Pro
1               5

( 2 ) INFORMATION FOR SEQ ID NO:26:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6

( D ) OTHER INFORMATION: /note= "Amino acid is amidated at
the C- terminal."

( x i ) SEQUENCE DESCRIPTION: SEQ ID NO:26:

Phe Arg Trp Trp Tyr Asp
1               5

( 2 ) INFORMATION FOR SEQ ID NO:27:

( i ) SEQUENCE CHARACTERISTICS:
      ( A ) LENGTH: 6 amino acids
      ( B ) TYPE: amino acid
      ( D ) TOPOLOGY: linear ( i x ) FEATURE:
      ( A ) NAME/KEY: Peptide
      ( B ) LOCATION: 1
      ( D ) OTHER INFORMATION: /note= "Amino acid is acetylated at
the N- terminal."

( i x ) FEATURE:
      ( A ) NAME/KEY: Peptide
      ( B ) LOCATION: 6
      ( D ) OTHER INFORMATION: /note= "Amino acid is amidated at
the C- terminal."

( x i ) SEQUENCE DESCRIPTION: SEQ ID NO:27:

Phe Arg Trp Trp Tyr Glu
1               5

( 2 ) INFORMATION FOR SEQ ID NO:28:

( i ) SEQUENCE CHARACTERISTICS:
      ( A ) LENGTH: 6 amino acids
      ( B ) TYPE: amino acid
      ( D ) TOPOLOGY: linear ( i x ) FEATURE:
      ( A ) NAME/KEY: Peptide
      ( B ) LOCATION: 1
      ( D ) OTHER INFORMATION: /note= "Amino acid is acetylated at
the N- terminal."

( i x ) FEATURE:
      ( A ) NAME/KEY: Peptide
      ( B ) LOCATION: 6
      ( D ) OTHER INFORMATION: /note= "Amino acid is amidated at
the C- terminal."

( x i ) SEQUENCE DESCRIPTION: SEQ ID NO:28:

Arg Trp Ile Gly Trp Arg
1               5

( 2 ) INFORMATION FOR SEQ ID NO:29:

( i ) SEQUENCE CHARACTERISTICS:
      ( A ) LENGTH: 6 amino acids
      ( B ) TYPE: amino acid
      ( D ) TOPOLOGY: linear ( i x ) FEATURE:
      ( A ) NAME/KEY: Peptide
      ( B ) LOCATION: 1
      ( D ) OTHER INFORMATION: /note= "Amino acid is acetylated at
the N- terminal."

( i x ) FEATURE:
      ( A ) NAME/KEY: Peptide
      ( B ) LOCATION: 6
      ( D ) OTHER INFORMATION: /note= "Amino acid is amidated at
the C- terminal."

( x i ) SEQUENCE DESCRIPTION: SEQ ID NO:29:

Arg Trp Ile Gly Trp Lys
1               5

( 2 ) INFORMATION FOR SEQ ID NO:30:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:30:

Arg Trp Ile Gly Trp Thr
1               5

( 2 ) INFORMATION FOR SEQ ID NO:31:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:31:

Arg Trp Ile Gly Trp Met
1               5

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:32:

Arg Trp Ile Gly Trp Ile
1               5

( 2 ) INFORMATION FOR SEQ ID NO:33:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:33:

Arg Trp Ile Gly Trp Ala
1                  5

( 2 ) INFORMATION FOR SEQ ID NO:34:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:34:

Arg Trp Ile Gly Trp Phe
1                  5

( 2 ) INFORMATION FOR SEQ ID NO:35:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:35:

Arg Trp Ile Gly Trp Ser
1                  5

( 2 ) INFORMATION FOR SEQ ID NO:36:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
  ( A ) NAME/KEY: Peptide
  ( B ) LOCATION: 1
  ( D ) OTHER INFORMATION: /note= "Amino acid is acetylated at the N- terminal."

( i x ) FEATURE:
  ( A ) NAME/KEY: Peptide
  ( B ) LOCATION: 6
  ( D ) OTHER INFORMATION: /note= "Amino acid is amidated at the C- terminal."

( x i ) SEQUENCE DESCRIPTION: SEQ ID NO:36:

Arg Trp Ile Gly Trp Leu
1               5

( 2 ) INFORMATION FOR SEQ ID NO:37:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:37:

Arg Trp Ile Gly Trp Cys
1               5

( 2 ) INFORMATION FOR SEQ ID NO:38:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:38:

Arg Trp Ile Gly Trp Trp
1               5

( 2 ) INFORMATION FOR SEQ ID NO:39:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "Amino acid is acetylated at the N- terminal."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:39:

Arg Trp Ile Gly Trp Tyr
1               5

( 2 ) INFORMATION FOR SEQ ID NO:40:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:40:

Arg Trp Ile Gly Trp Val
1               5

( 2 ) INFORMATION FOR SEQ ID NO:41:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:41:

Arg Trp Ile Gly Trp Gln
1               5

( 2 ) INFORMATION FOR SEQ ID NO:42:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6

( D ) OTHER INFORMATION: /note= "Amino acid is amidated at the C- terminal."

( x i ) SEQUENCE DESCRIPTION: SEQ ID NO:42:

Arg Trp Ile Gly Trp His
1               5

( 2 ) INFORMATION FOR SEQ ID NO:43:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:43:

Arg Trp Ile Gly Trp Gly
1               5

( 2 ) INFORMATION FOR SEQ ID NO:44:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:44:

Arg Trp Ile Gly Trp Pro
1               5

( 2 ) INFORMATION FOR SEQ ID NO:45:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at the N- terminal."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:45:

```
Arg  Trp  Ile  Gly  Trp  Asn
1                   5
```

(2) INFORMATION FOR SEQ ID NO:46:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note= "Amino acid is acetylated at the N- terminal."

(ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:46:

```
Arg  Trp  Ile  Gly  Trp  Glu
1                   5
```

(2) INFORMATION FOR SEQ ID NO:47:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 1
        (D) OTHER INFORMATION: /note= "Amino acid is acetylated at the N- terminal."

(ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:47:

```
Arg  Trp  Ile  Gly  Trp  Asp
1                   5
```

(2) INFORMATION FOR SEQ ID NO:48:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:48:

```
Trp  Trp  Pro  Lys  His  Gly
1                   5
```

(2) INFORMATION FOR SEQ ID NO:49:

(i) SEQUENCE CHARACTERISTICS:
        (A) LENGTH: 6 amino acids
        (B) TYPE: amino acid
        (D) TOPOLOGY: linear ( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:49:

Trp Trp Pro Lys His Asn
1               5

( 2 ) INFORMATION FOR SEQ ID NO:50:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:50:

Trp Trp Pro Lys His Lys
1               5

( 2 ) INFORMATION FOR SEQ ID NO:51:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:51:

Trp Trp Pro Lys His His
1               5

( 2 ) INFORMATION FOR SEQ ID NO:52:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:52:

Trp Trp Pro Lys His Ser
1               5

( 2 ) INFORMATION FOR SEQ ID NO:53:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:53:

Trp Trp Pro Lys His Arg
1               5

( 2 ) INFORMATION FOR SEQ ID NO:54:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:54:

Trp Trp Pro Lys His Ala
1               5

( 2 ) INFORMATION FOR SEQ ID NO:55:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:55:

Trp Trp Pro Lys His Gln
1               5

( 2 ) INFORMATION FOR SEQ ID NO:56:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:56:

Trp Trp Pro Lys His Ile
1               5

( 2 ) INFORMATION FOR SEQ ID NO:57:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:57:

Trp Trp Pro Lys His Pro
1               5

( 2 ) INFORMATION FOR SEQ ID NO:58:

( i ) SEQUENCE CHARACTERISTICS:
      ( A ) LENGTH: 6 amino acids
      ( B ) TYPE: amino acid
      ( D ) TOPOLOGY: linear ( i x ) FEATURE:
      ( A ) NAME/KEY: Peptide
      ( B ) LOCATION: 6
      ( D ) OTHER INFORMATION: /note= "Amino acid is amidated at
            the C- terminal."

( x i ) SEQUENCE DESCRIPTION: SEQ ID NO:58:

Trp Trp Pro Lys His Thr
1               5

( 2 ) INFORMATION FOR SEQ ID NO:59:

( i ) SEQUENCE CHARACTERISTICS:
      ( A ) LENGTH: 6 amino acids
      ( B ) TYPE: amino acid
      ( D ) TOPOLOGY: linear ( i x ) FEATURE:
      ( A ) NAME/KEY: Peptide
      ( B ) LOCATION: 6
      ( D ) OTHER INFORMATION: /note= "Amino acid is amidated at
            the C- terminal."

( x i ) SEQUENCE DESCRIPTION: SEQ ID NO:59:

Trp Trp Pro Lys His Cys
1               5

( 2 ) INFORMATION FOR SEQ ID NO:60:

( i ) SEQUENCE CHARACTERISTICS:
      ( A ) LENGTH: 6 amino acids
      ( B ) TYPE: amino acid
      ( D ) TOPOLOGY: linear ( i x ) FEATURE:
      ( A ) NAME/KEY: Peptide
      ( B ) LOCATION: 6
      ( D ) OTHER INFORMATION: /note= "Amino acid is amidated at
            the C- terminal."

( x i ) SEQUENCE DESCRIPTION: SEQ ID NO:60:

Trp Trp Pro Lys His Val
1               5

( 2 ) INFORMATION FOR SEQ ID NO:61:

( i ) SEQUENCE CHARACTERISTICS:
      ( A ) LENGTH: 6 amino acids
      ( B ) TYPE: amino acid
      ( D ) TOPOLOGY: linear ( i x ) FEATURE:
      ( A ) NAME/KEY: Peptide
      ( B ) LOCATION: 6
      ( D ) OTHER INFORMATION: /note= "Amino acid is amidated at
            the C- terminal."

( x i ) SEQUENCE DESCRIPTION: SEQ ID NO:61:

Trp Trp Pro Lys His Met
1               5

( 2 ) INFORMATION FOR SEQ ID NO:62:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:62:

Trp Trp Pro Lys His Phe
  1               5

( 2 ) INFORMATION FOR SEQ ID NO:63:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:63:

Trp Trp Pro Lys His Glu
  1               5

( 2 ) INFORMATION FOR SEQ ID NO:64:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:64:

Trp Trp Pro Lys His Tyr
  1               5

( 2 ) INFORMATION FOR SEQ ID NO:65:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:65:

Trp Trp Pro Lys His Leu
  1               5

( 2 ) INFORMATION FOR SEQ ID NO:66:

( i ) SEQUENCE CHARACTERISTICS:
        ( A ) LENGTH: 6 amino acids (B) TYPE: amino acid
(D) TOPOLOGY: linear (ix) FEATURE:
(A) NAME/KEY: Peptide
(B) LOCATION: 6
(D) OTHER INFORMATION: /note= "Amino acid is amidated at the C-terminal."

(xi) SEQUENCE DESCRIPTION: SEQ ID NO:66:

Trp Trp Pro Lys His Asp
1               5

(2) INFORMATION FOR SEQ ID NO:67:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 6
(D) OTHER INFORMATION: /note= "Amino acid is amidated at the C-terminal."

(xi) SEQUENCE DESCRIPTION: SEQ ID NO:67:

Trp Trp Pro Lys His Trp
1               5

(2) INFORMATION FOR SEQ ID NO:68:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 4
(D) OTHER INFORMATION: /note= "Amino acid is amidated at the C-terminal."

(xi) SEQUENCE DESCRIPTION: SEQ ID NO:68:

Trp Trp Pro Lys
1

(2) INFORMATION FOR SEQ ID NO:69:

(i) SEQUENCE CHARACTERISTICS:
(A) LENGTH: 4 amino acids
(B) TYPE: amino acid
(D) TOPOLOGY: linear (ix) FEATURE:
(A) NAME/KEY: Peptide
(B) LOCATION: 4
(D) OTHER INFORMATION: /note= "Amino acid is amidated at the C-terminal."

(xi) SEQUENCE DESCRIPTION: SEQ ID NO:69:

Trp Trp Pro Arg
1

(2) INFORMATION FOR SEQ ID NO:70:

(i) SEQUENCE CHARACTERISTICS:
(A) LENGTH: 6 amino acids
(B) TYPE: amino acid
(D) TOPOLOGY: linear (ix) FEATURE:

(A) NAME/KEY: Peptide
(B) LOCATION: 6
(D) OTHER INFORMATION: /note= "Amino acid is amidated at the C- terminal."

(xi) SEQUENCE DESCRIPTION: SEQ ID NO:70:

```
Tyr  Pro  Phe  Gly  Phe  Arg
1                    5
```

(2) INFORMATION FOR SEQ ID NO:71:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 6
(D) OTHER INFORMATION: /note= "Amino acid is amidated at the C- terminal."

(xi) SEQUENCE DESCRIPTION: SEQ ID NO:71:

```
Tyr  Pro  Phe  Gly  Phe  Gly
1                    5
```

(2) INFORMATION FOR SEQ ID NO:72:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 6
(D) OTHER INFORMATION: /note= "Amino acid is amidated at the C- terminal."

(xi) SEQUENCE DESCRIPTION: SEQ ID NO:72:

```
Tyr  Pro  Phe  Gly  Phe  Lys
1                    5
```

(2) INFORMATION FOR SEQ ID NO:73:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 6
(D) OTHER INFORMATION: /note= "Amino acid is amidated at the C- terminal."

(xi) SEQUENCE DESCRIPTION: SEQ ID NO:73:

```
Tyr  Pro  Phe  Gly  Phe  Ser
1                    5
```

(2) INFORMATION FOR SEQ ID NO:74:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 6
(D) OTHER INFORMATION: /note= "Amino acid is amidated at the C- terminal."

( x i ) SEQUENCE DESCRIPTION: SEQ ID NO:74:

Tyr Pro Phe Gly Phe Ala
1               5

( 2 ) INFORMATION FOR SEQ ID NO:75:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:75:

Tyr Pro Phe Gly Phe Asn
1               5

( 2 ) INFORMATION FOR SEQ ID NO:76:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:76:

Tyr Pro Phe Gly Phe Pro
1               5

( 2 ) INFORMATION FOR SEQ ID NO:77:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:77:

Tyr Pro Phe Gly Phe Gln
1               5

( 2 ) INFORMATION FOR SEQ ID NO:78:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:78:

Tyr Pro Phe Gly Phe Met (2) INFORMATION FOR SEQ ID NO:79:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:79:

Tyr Pro Phe Gly Phe His
1               5

(2) INFORMATION FOR SEQ ID NO:80:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:80:

Tyr Pro Phe Gly Phe Tyr
1               5

(2) INFORMATION FOR SEQ ID NO:81:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:81:

Tyr Pro Phe Gly Phe Ile
1               5

(2) INFORMATION FOR SEQ ID NO:82:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 6
        (D) OTHER INFORMATION: /note= "Amino acid is amidated at the C- terminal."

(xi) SEQUENCE DESCRIPTION: SEQ ID NO:82:

Tyr Pro Phe Gly Phe Thr
1               5

(2) INFORMATION FOR SEQ ID NO:83:

( i ) SEQUENCE CHARACTERISTICS:
   ( A ) LENGTH: 6 amino acids
   ( B ) TYPE: amino acid
   ( D ) TOPOLOGY: linear ( i x ) FEATURE:
   ( A ) NAME/KEY: Peptide
   ( B ) LOCATION: 6
   ( D ) OTHER INFORMATION: /note= "Amino acid is amidated at
      the C- terminal."

( x i ) SEQUENCE DESCRIPTION: SEQ ID NO:83:

Tyr Pro Phe Gly Phe Leu
1               5

( 2 ) INFORMATION FOR SEQ ID NO:84:

( i ) SEQUENCE CHARACTERISTICS:
   ( A ) LENGTH: 6 amino acids
   ( B ) TYPE: amino acid
   ( D ) TOPOLOGY: linear ( i x ) FEATURE:
   ( A ) NAME/KEY: Peptide
   ( B ) LOCATION: 6
   ( D ) OTHER INFORMATION: /note= "Amino acid is amidated at
      the C- terminal."

( x i ) SEQUENCE DESCRIPTION: SEQ ID NO:84:

Tyr Pro Phe Gly Phe Val
1               5

( 2 ) INFORMATION FOR SEQ ID NO:85:

( i ) SEQUENCE CHARACTERISTICS:
   ( A ) LENGTH: 6 amino acids
   ( B ) TYPE: amino acid
   ( D ) TOPOLOGY: linear ( i x ) FEATURE:
   ( A ) NAME/KEY: Peptide
   ( B ) LOCATION: 6
   ( D ) OTHER INFORMATION: /note= "Amino acid is amidated at
      the C- terminal."

( x i ) SEQUENCE DESCRIPTION: SEQ ID NO:85:

Tyr Pro Phe Gly Phe Phe
1               5

( 2 ) INFORMATION FOR SEQ ID NO:86:

( i ) SEQUENCE CHARACTERISTICS:
   ( A ) LENGTH: 6 amino acids
   ( B ) TYPE: amino acid
   ( D ) TOPOLOGY: linear ( i x ) FEATURE:
   ( A ) NAME/KEY: Peptide
   ( B ) LOCATION: 6
   ( D ) OTHER INFORMATION: /note= "Amino acid is amidated at
      the C- terminal."

( x i ) SEQUENCE DESCRIPTION: SEQ ID NO:86:

Tyr Pro Phe Gly Phe Asp
1               5

( 2 ) INFORMATION FOR SEQ ID NO:87:

( i ) SEQUENCE CHARACTERISTICS:
   ( A ) LENGTH: 6 amino acids
   ( B ) TYPE: amino acid (D) TOPOLOGY: linear (ix) FEATURE:
    (A) NAME/KEY: Peptide
    (B) LOCATION: 6
    (D) OTHER INFORMATION: /note= "Amino acid is amidated at the C- terminal."

(xi) SEQUENCE DESCRIPTION: SEQ ID NO:87:

```
Tyr Pro Phe Gly Phe Cys
1               5
```

(2) INFORMATION FOR SEQ ID NO:88:

(i) SEQUENCE CHARACTERISTICS:
    (A) LENGTH: 6 amino acids
    (B) TYPE: amino acid
    (D) TOPOLOGY: linear (ix) FEATURE:
    (A) NAME/KEY: Peptide
    (B) LOCATION: 6
    (D) OTHER INFORMATION: /note= "Amino acid is amidated at the C- terminal."

(xi) SEQUENCE DESCRIPTION: SEQ ID NO:88:

```
Tyr Pro Phe Gly Phe Trp
1               5
```

(2) INFORMATION FOR SEQ ID NO:89:

(i) SEQUENCE CHARACTERISTICS:
    (A) LENGTH: 6 amino acids
    (B) TYPE: amino acid
    (D) TOPOLOGY: linear (ix) FEATURE:
    (A) NAME/KEY: Peptide
    (B) LOCATION: 6
    (D) OTHER INFORMATION: /note= "Amino acid is amidated at the C- terminal."

(xi) SEQUENCE DESCRIPTION: SEQ ID NO:89:

```
Tyr Pro Phe Gly Phe Glu
1               5
```

(2) INFORMATION FOR SEQ ID NO:90:

(i) SEQUENCE CHARACTERISTICS:
    (A) LENGTH: 6 amino acids
    (B) TYPE: amino acid
    (D) TOPOLOGY: linear (ix) FEATURE:
    (A) NAME/KEY: Peptide
    (B) LOCATION: 1..6
    (D) OTHER INFORMATION: /note= "With the exception of Gly at position 6, all the amino acids are the D-amino acids."

(ix) FEATURE:
    (A) NAME/KEY: Peptide
    (B) LOCATION: 6
    (D) OTHER INFORMATION: /note= "Amino acid is amidated at the C- terminal."

(xi) SEQUENCE DESCRIPTION: SEQ ID NO:90:

```
Ile Met Ser Trp Trp Gly
1               5
```

(2) INFORMATION FOR SEQ ID NO:91:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1..6
    ( D ) OTHER INFORMATION: /note= "All amino acids are D-amino acids."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:91:

```
Ile Met Ser Trp Trp Ala
 1               5
```

( 2 ) INFORMATION FOR SEQ ID NO:92:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1..6
    ( D ) OTHER INFORMATION: /note= "All amino acids are D-amino acids."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:92:

```
Ile Met Ser Trp Trp His
 1               5
```

( 2 ) INFORMATION FOR SEQ ID NO:93:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1..6
    ( D ) OTHER INFORMATION: /note= "All amino acids are D-amino acids."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:93:

```
Ile Met Ser Trp Trp Val
 1               5
```

( 2 ) INFORMATION FOR SEQ ID NO:94:

( i ) SEQUENCE CHARACTERISTICS:
    ( A ) LENGTH: 6 amino acids
    ( B ) TYPE: amino acid
    ( D ) TOPOLOGY: linear ( i x ) FEATURE:
    ( A ) NAME/KEY: Peptide
    ( B ) LOCATION: 1..6
    ( D ) OTHER INFORMATION: /note= "All amino acids are D-amino acids."

( i x ) FEATURE:
    ( A ) NAME/KEY: Peptide
    ( B ) LOCATION: 6
    ( D ) OTHER INFORMATION: /note= "Amino acid is amidated at the C- terminal."

( x i ) SEQUENCE DESCRIPTION: SEQ ID NO:94:

Ile Met Ser Trp Trp Tyr
1                   5

( 2 ) INFORMATION FOR SEQ ID NO:95:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino acids."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:95:

Ile Met Ser Trp Trp Ser
1                   5

( 2 ) INFORMATION FOR SEQ ID NO:96:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino acids."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:96:

Ile Met Ser Trp Trp Ile
1                   5

( 2 ) INFORMATION FOR SEQ ID NO:97:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino acids."

( i x ) FEATURE:
    ( A ) NAME/KEY: Peptide
    ( B ) LOCATION: 6
    ( D ) OTHER INFORMATION: /note= "Amino acid is amidated at
        the C- terminal."

( x i ) SEQUENCE DESCRIPTION: SEQ ID NO:97:

```
Ile  Met  Ser  Trp  Trp  Arg
 1                 5
```

( 2 ) INFORMATION FOR SEQ ID NO:98:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:98:

```
Ile  Met  Ser  Trp  Trp  Met
 1                 5
```

( 2 ) INFORMATION FOR SEQ ID NO:99:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:99:

```
Ile  Met  Ser  Trp  Trp  Asn
 1                 5
```

( 2 ) INFORMATION FOR SEQ ID NO:100:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino
            acids."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:100:

Ile Met Ser Trp Trp Gln
1               5

( 2 ) INFORMATION FOR SEQ ID NO:101:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:101:

Ile Met Ser Trp Trp Pro
1               5

( 2 ) INFORMATION FOR SEQ ID NO:102:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:102:

Ile Met Ser Trp Trp Thr
1               5

( 2 ) INFORMATION FOR SEQ ID NO:103:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:103:

Ile Met Ser Trp Trp Trp 1        5

( 2 ) INFORMATION FOR SEQ ID NO:104:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:104:

Ile   Met   Ser   Trp   Trp   Asp
    1                       5

( 2 ) INFORMATION FOR SEQ ID NO:105:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:105:

Ile   Met   Ser   Trp   Trp   Glu
    1                       5

( 2 ) INFORMATION FOR SEQ ID NO:106:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "All amino acids are D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:106:

Ile   Met   Ser   Trp   Trp   Cys
    1                       5

( 2 ) INFORMATION FOR SEQ ID NO:107:

(i) SEQUENCE CHARACTERISTICS:
 (A) LENGTH: 6 amino acids
 (B) TYPE: amino acid
 (D) TOPOLOGY: linear (ix) FEATURE:
 (A) NAME/KEY: Peptide
 (B) LOCATION: 1..6
 (D) OTHER INFORMATION: /note= "All amino acids are D-amino acids."

(ix) FEATURE:
 (A) NAME/KEY: Peptide
 (B) LOCATION: 6
 (D) OTHER INFORMATION: /note= "Amino acid is amidated at the C- terminal."

(xi) SEQUENCE DESCRIPTION: SEQ ID NO:107:

```
Ile  Met  Ser  Trp  Trp  Lys
1                    5
```

(2) INFORMATION FOR SEQ ID NO:108:

(i) SEQUENCE CHARACTERISTICS:
 (A) LENGTH: 6 amino acids
 (B) TYPE: amino acid
 (D) TOPOLOGY: linear (ix) FEATURE:
 (A) NAME/KEY: Peptide
 (B) LOCATION: 1..6
 (D) OTHER INFORMATION: /note= "All amino acids are D-amino acids."

(ix) FEATURE:
 (A) NAME/KEY: Peptide
 (B) LOCATION: 6
 (D) OTHER INFORMATION: /note= "Amino acid is amidated at the C- terminal."

(xi) SEQUENCE DESCRIPTION: SEQ ID NO:108:

```
Ile  Met  Ser  Trp  Trp  Phe
1                    5
```

(2) INFORMATION FOR SEQ ID NO:109:

(i) SEQUENCE CHARACTERISTICS:
 (A) LENGTH: 6 amino acids
 (B) TYPE: amino acid
 (D) TOPOLOGY: linear (ix) FEATURE:
 (A) NAME/KEY: Peptide
 (B) LOCATION: 1..6
 (D) OTHER INFORMATION: /note= "All amino acids are D-amino acids."

(ix) FEATURE:
 (A) NAME/KEY: Peptide
 (B) LOCATION: 6
 (D) OTHER INFORMATION: /note= "Amino acid is amidated at the C- terminal."

(xi) SEQUENCE DESCRIPTION: SEQ ID NO:109:

```
Ile  Met  Ser  Trp  Trp  Leu
1                    5
```

(2) INFORMATION FOR SEQ ID NO:110:

(i) SEQUENCE CHARACTERISTICS:
 (A) LENGTH: 7 amino acids
 (B) TYPE: amino acid
 (D) TOPOLOGY: linear ( i x ) FEATURE:
    ( A ) NAME/KEY: Peptide
    ( B ) LOCATION: 1..7
    ( D ) OTHER INFORMATION: /note= "With the exception of Gly in position 6, all amino acids are D-amino acids."

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:110:

Ile Met Ser Trp Trp Gly Phe
1               5

( 2 ) INFORMATION FOR SEQ ID NO:111:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Peptide
    ( B ) LOCATION: 1..7
    ( D ) OTHER INFORMATION: /note= "With the exception of Gly in position 6, all amino acids are D-amino acids."

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:111:

Ile Met Ser Trp Trp Gly Lys
1               5

( 2 ) INFORMATION FOR SEQ ID NO:112:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Peptide
    ( B ) LOCATION: 1..7
    ( D ) OTHER INFORMATION: /note= "With the exception of Gly in position 6, all amino acids are D-amino acids."

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:112:

Ile Met Ser Trp Trp Gly Met
1               5

( 2 ) INFORMATION FOR SEQ ID NO:113:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Peptide
    ( B ) LOCATION: 1..7
    ( D ) OTHER INFORMATION: /note= "With the exception of Gly in position 6, all amino acids are D-amino acids."

(i x) FEATURE:
    (A) NAME/KEY: Peptide
    (B) LOCATION: 7
    (D) OTHER INFORMATION: /note= "Amino acid is amidated at
        the C- terminal."

(x i) SEQUENCE DESCRIPTION: SEQ ID NO:113:

Ile Met Ser Trp Trp Gly Pro
1                5

(2) INFORMATION FOR SEQ ID NO:114:

(i) SEQUENCE CHARACTERISTICS:
        (A) LENGTH: 7 amino acids
        (B) TYPE: amino acid
        (D) TOPOLOGY: linear (i x) FEATURE:
        (A) NAME/KEY: Peptide
        (B) LOCATION: 1..7
        (D) OTHER INFORMATION: /note= "With the exception of Gly
            in position 6, all amino acids are D-amino acids."

(i x) FEATURE:
        (A) NAME/KEY: Peptide
        (B) LOCATION: 7
        (D) OTHER INFORMATION: /note= "Amino acid is amidated at
            the C- terminal."

(x i) SEQUENCE DESCRIPTION: SEQ ID NO:114:

Ile Met Ser Trp Trp Gly Ile
1                5

(2) INFORMATION FOR SEQ ID NO:115:

(i) SEQUENCE CHARACTERISTICS:
        (A) LENGTH: 7 amino acids
        (B) TYPE: amino acid
        (D) TOPOLOGY: linear (i x) FEATURE:
        (A) NAME/KEY: Peptide
       (B) LOCATION: 1..7
        (D) OTHER INFORMATION: /note= "With the exception of Gly
            in position 6, all amino acids are D-amino acids."

(i x) FEATURE:
        (A) NAME/KEY: Peptide
        (B) LOCATION: 7
        (D) OTHER INFORMATION: /note= "Amino acid is amidated at
            the C- terminal."

(x i) SEQUENCE DESCRIPTION: SEQ ID NO:115:

Ile Met Ser Trp Trp Gly Arg
1                5

(2) INFORMATION FOR SEQ ID NO:116:

(i) SEQUENCE CHARACTERISTICS:
        (A) LENGTH: 7 amino acids
        (B) TYPE: amino acid
        (D) TOPOLOGY: linear (i x) FEATURE:
        (A) NAME/KEY: Peptide
        (B) LOCATION: 1..7
        (D) OTHER INFORMATION: /note= "With the exception of Gly
            in position 6, all amino acids are D-amino acids."

(i x) FEATURE:
        (A) NAME/KEY: Peptide
        (B) LOCATION: 7
        (D) OTHER INFORMATION: /note= "Amino acid is amidated at the C- terminal."

( x i ) SEQUENCE DESCRIPTION: SEQ ID NO:116:

Ile Met Ser Trp Trp Gly His
1               5

( 2 ) INFORMATION FOR SEQ ID NO:117:

( i ) SEQUENCE CHARACTERISTICS:
        ( A ) LENGTH: 7 amino acids
        ( B ) TYPE: amino acid
        ( D ) TOPOLOGY: linear ( i x ) FEATURE:
        ( A ) NAME/KEY: Peptide
        ( B ) LOCATION: 1..7
        ( D ) OTHER INFORMATION: /note= "With the exception of Gly
            in position 6, all amino acids are D-amino acids."

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:117:

Ile Met Ser Trp Trp Gly Tyr
1               5

( 2 ) INFORMATION FOR SEQ ID NO:118:

( i ) SEQUENCE CHARACTERISTICS:
        ( A ) LENGTH: 7 amino acids
        ( B ) TYPE: amino acid
        ( D ) TOPOLOGY: linear ( i x ) FEATURE:
        ( A ) NAME/KEY: Peptide
        ( B ) LOCATION: 1..7
        ( D ) OTHER INFORMATION: /note= "With the exception of Gly
            in position 6, all amino acids are D-amino acids."

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:118:

Ile Met Ser Trp Trp Gly Thr
1               5

( 2 ) INFORMATION FOR SEQ ID NO:119:

( i ) SEQUENCE CHARACTERISTICS:
        ( A ) LENGTH: 7 amino acids
        ( B ) TYPE: amino acid
        ( D ) TOPOLOGY: linear ( i x ) FEATURE:
        ( A ) NAME/KEY: Peptide
        ( B ) LOCATION: 1..7
        ( D ) OTHER INFORMATION: /note= "With the exception of Gly
            in positions 6 and 7, all amino acids are D-amino
            acids."

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:119:

```
  Ile  Met  Ser  Trp  Trp  Gly  Gly
  1                  5
```

( 2 ) INFORMATION FOR SEQ ID NO:120:

( i ) SEQUENCE CHARACTERISTICS:
        ( A ) LENGTH: 7 amino acids
        ( B ) TYPE: amino acid
        ( D ) TOPOLOGY: linear ( i x ) FEATURE:
        ( A ) NAME/KEY: Peptide
        ( B ) LOCATION: 1..7
        ( D ) OTHER INFORMATION: /note= "With the exception of Gly
            in position 6, all amino acids are D-amino acids."

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:120:

```
  Ile  Met  Ser  Trp  Trp  Gly  Ser
  1                  5
```

( 2 ) INFORMATION FOR SEQ ID NO:121:

( i ) SEQUENCE CHARACTERISTICS:
        ( A ) LENGTH: 7 amino acids
        ( B ) TYPE: amino acid
        ( D ) TOPOLOGY: linear ( i x ) FEATURE:
        ( A ) NAME/KEY: Peptide
        ( B ) LOCATION: 1..7
        ( D ) OTHER INFORMATION: /note= "With the exception of Gly
            in position 6, all amino acids are D-amino acids."

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:121:

```
  Ile  Met  Ser  Trp  Trp  Gly  Trp
  1                  5
```

( 2 ) INFORMATION FOR SEQ ID NO:122:

( i ) SEQUENCE CHARACTERISTICS:
        ( A ) LENGTH: 7 amino acids
        ( B ) TYPE: amino acid
        ( D ) TOPOLOGY: linear ( i x ) FEATURE:
        ( A ) NAME/KEY: Peptide
        ( B ) LOCATION: 1..7
        ( D ) OTHER INFORMATION: /note= "With the exception of Gly
            in position 6, all amino acids are D-amino acids."

( i x ) FEATURE:
        ( A ) NAME/KEY: Peptide
        ( B ) LOCATION: 7
        ( D ) OTHER INFORMATION: /note= "Amino acid is amidated at
            the C- terminal."

( x i ) SEQUENCE DESCRIPTION: SEQ ID NO:122:

```
  Ile  Met  Ser  Trp  Trp  Gly  Leu
  1                  5
```

( 2 ) INFORMATION FOR SEQ ID NO:123:

( i ) SEQUENCE CHARACTERISTICS:
                ( A ) LENGTH: 7 amino acids
                ( B ) TYPE: amino acid
                ( D ) TOPOLOGY: linear ( i x ) FEATURE:
                ( A ) NAME/KEY: Peptide
                ( B ) LOCATION: 1..7
                ( D ) OTHER INFORMATION: /note= "With the exception of Gly
                        in position 6, all amino acids are D-amino acids."

( i x ) FEATURE:
                ( A ) NAME/KEY: Peptide
                ( B ) LOCATION: 7
                ( D ) OTHER INFORMATION: /note= "Amino acid is amidated at
                        the C- terminal."

( x i ) SEQUENCE DESCRIPTION: SEQ ID NO:123:

Ile  Met  Ser  Trp  Trp  Gly  Ala
1                    5

( 2 ) INFORMATION FOR SEQ ID NO:124:

( i ) SEQUENCE CHARACTERISTICS:
                ( A ) LENGTH: 7 amino acids
                ( B ) TYPE: amino acid
                ( D ) TOPOLOGY: linear ( i x ) FEATURE:
                ( A ) NAME/KEY: Peptide
                ( B ) LOCATION: 1..7
                ( D ) OTHER INFORMATION: /note= "With the exception of Gly
                        in position 6, all amino acids are D-amino acids."

( i x ) FEATURE:
                ( A ) NAME/KEY: Peptide
                ( B ) LOCATION: 7
                ( D ) OTHER INFORMATION: /note= "Amino acid is amidated at
                        the C- terminal."

( x i ) SEQUENCE DESCRIPTION: SEQ ID NO:124:

Ile  Met  Ser  Trp  Trp  Gly  Asn
        1                    5

( 2 ) INFORMATION FOR SEQ ID NO:125:

( i ) SEQUENCE CHARACTERISTICS:
                ( A ) LENGTH: 7 amino acids
                ( B ) TYPE: amino acid
                ( D ) TOPOLOGY: linear ( i x ) FEATURE:
                ( A ) NAME/KEY: Peptide
                ( B ) LOCATION: 1..7
                ( D ) OTHER INFORMATION: /note= "With the exception of Gly
                        in position 6, all amino acids are D-amino acids."

( i x ) FEATURE:
                ( A ) NAME/KEY: Peptide
                ( B ) LOCATION: 7
                ( D ) OTHER INFORMATION: /note= "Amino acid is amidated at
                        the C- terminal."

( x i ) SEQUENCE DESCRIPTION: SEQ ID NO:125:

Ile  Met  Ser  Trp  Trp  Gly  Val
        1                    5

( 2 ) INFORMATION FOR SEQ ID NO:126:

( i ) SEQUENCE CHARACTERISTICS:
                ( A ) LENGTH: 7 amino acids
                ( B ) TYPE: amino acid
                ( D ) TOPOLOGY: linear ( i x ) FEATURE:
    ( A ) NAME/KEY: Peptide
    ( B ) LOCATION: 1..7
    ( D ) OTHER INFORMATION: /note= "With the exception of Gly in position 6, all amino acids are D-amino acids."

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:126:

Ile Met Ser Trp Trp Gly Gln
1               5

( 2 ) INFORMATION FOR SEQ ID NO:127:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Peptide
    ( B ) LOCATION: 1..7
    ( D ) OTHER INFORMATION: /note= "With the exception of Gly in position 6, all amino acids are D-amino acids."

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:127:

Ile Met Ser Trp Trp Gly Glu
1               5

( 2 ) INFORMATION FOR SEQ ID NO:128:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Peptide
    ( B ) LOCATION: 1..7
    ( D ) OTHER INFORMATION: /note= "With the exception of Gly in position 6, all amino acids are D-amino acids."

( i x ) FEATURE:
    ( A ) NAME/KEY: Peptide
    ( B ) LOCATION: 7
    ( D ) OTHER INFORMATION: /note= "Amino acid is amidated at the C- terminal."

( x i ) SEQUENCE DESCRIPTION: SEQ ID NO:128:

Ile Met Ser Trp Trp Gly Cys
1               5

( 2 ) INFORMATION FOR SEQ ID NO:129:

( i ) SEQUENCE CHARACTERISTICS:
    ( A ) LENGTH: 7 amino acids
    ( B ) TYPE: amino acid
    ( D ) TOPOLOGY: linear ( i x ) FEATURE:
    ( A ) NAME/KEY: Peptide
    ( B ) LOCATION: 1..7
    ( D ) OTHER INFORMATION: /note= "With the exception of Gly in position 6, all amino acids are D-amino acids."

( i x ) FEATURE:
    ( A ) NAME/KEY: Peptide
    ( B ) LOCATION: 7
    ( D ) OTHER INFORMATION: /note= "Amino acid is amidated at
        the C- terminal."

( x i ) SEQUENCE DESCRIPTION: SEQ ID NO:129:

```
Ile  Met  Ser  Trp  Trp  Gly  Asp
1                   5
```

( 2 ) INFORMATION FOR SEQ ID NO:130:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "With the exception of Gly
            at position 5, all the amino acids are the D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:130:

```
Ile  Met  Thr  Trp  Gly  Pro
1                   5
```

( 2 ) INFORMATION FOR SEQ ID NO:131:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "With the exception of Gly
            at position 5, all the amino acids are the D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:131:

```
Ile  Met  Thr  Trp  Gly  Tyr
1                   5
```

( 2 ) INFORMATION FOR SEQ ID NO:132:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "With the exception of Gly
            at position 5, all the amino acids are the D-amino
            acids."

( i x ) FEATURE:
    ( A ) NAME/KEY: Peptide
    ( B ) LOCATION: 6
    ( D ) OTHER INFORMATION: /note= "Amino acid is amidated at
        the C- terminal."

( x i ) SEQUENCE DESCRIPTION: SEQ ID NO:132:

Ile Met Thr Trp Gly Phe
1                   5

( 2 ) INFORMATION FOR SEQ ID NO:133:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "With the exception of Gly
            at position 5, all the amino acids are the D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:133:

Ile Met Thr Trp Gly Met
1                   5

( 2 ) INFORMATION FOR SEQ ID NO:134:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "With the exception of Gly
            at position 5, all the amino acids are the D-amino
            acids."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:134:

Ile Met Thr Trp Gly Trp
1                   5

( 2 ) INFORMATION FOR SEQ ID NO:135:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "With the exception of Gly
            at position 5, all the amino acids are the D-amino
            acids."

( i x ) FEATURE:
        ( A ) NAME/KEY: Peptide (B) LOCATION: 6
(D) OTHER INFORMATION: /note= "Amino acid is amidated at the C- terminal."

(x i) SEQUENCE DESCRIPTION: SEQ ID NO:135:

Ile Met Thr Trp Gly Ile
1               5

(2) INFORMATION FOR SEQ ID NO:136:

(i) SEQUENCE CHARACTERISTICS:
(A) LENGTH: 6 amino acids
(B) TYPE: amino acid
(D) TOPOLOGY: linear (i x) FEATURE:
(A) NAME/KEY: Peptide
(B) LOCATION: 1..6
(D) OTHER INFORMATION: /note= "With the exception of Gly at position 5, all the amino acids are the D-amino acids."

(i x) FEATURE:
(A) NAME/KEY: Peptide
(B) LOCATION: 6
(D) OTHER INFORMATION: /note= "Amino acid is amidated at the C- terminal."

(x i) SEQUENCE DESCRIPTION: SEQ ID NO:136:

Ile Met Thr Trp Gly Ala
1               5

(2) INFORMATION FOR SEQ ID NO:137:

(i) SEQUENCE CHARACTERISTICS:
(A) LENGTH: 6 amino acids
(B) TYPE: amino acid
(D) TOPOLOGY: linear (i x) FEATURE:
(A) NAME/KEY: Peptide
(B) LOCATION: 1..6
(D) OTHER INFORMATION: /note= "With the exception of Gly at position 5, all the amino acids are the D-amino acids."

(i x) FEATURE:
(A) NAME/KEY: Peptide
(B) LOCATION: 6
(D) OTHER INFORMATION: /note= "Amino acid is amidated at the C- terminal."

(x i) SEQUENCE DESCRIPTION: SEQ ID NO:137:

Ile Met Thr Trp Gly Leu
1               5

(2) INFORMATION FOR SEQ ID NO:138:

(i) SEQUENCE CHARACTERISTICS:
(A) LENGTH: 6 amino acids
(B) TYPE: amino acid
(D) TOPOLOGY: linear (i x) FEATURE:
(A) NAME/KEY: Peptide
(B) LOCATION: 1..6
(D) OTHER INFORMATION: /note= "With the exception of Gly at positions 5 and 6, all the amino acids are the D-amino acids."

(i x) FEATURE:
(A) NAME/KEY: Peptide
(B) LOCATION: 6
(D) OTHER INFORMATION: /note= "Amino acid is amidated at the C- terminal."

( x i ) SEQUENCE DESCRIPTION: SEQ ID NO:138:

Ile Met Thr Trp Gly Gly
1               5

( 2 ) INFORMATION FOR SEQ ID NO:139:

( i ) SEQUENCE CHARACTERISTICS:
( A ) LENGTH: 6 amino acids
( B ) TYPE: amino acid
( D ) TOPOLOGY: linear ( i x ) FEATURE:
( A ) NAME/KEY: Peptide
( B ) LOCATION: 1..6
( D ) OTHER INFORMATION: /note= "With the exception of Gly at position 5, all the amino acids are the D-amino acids."

( i x ) FEATURE:
( A ) NAME/KEY: Peptide
( B ) LOCATION: 6
( D ) OTHER INFORMATION: /note= "Amino acid is amidated at the C- terminal."

( x i ) SEQUENCE DESCRIPTION: SEQ ID NO:139:

Ile Met Thr Trp Gly Cys
1               5

( 2 ) INFORMATION FOR SEQ ID NO:140:

( i ) SEQUENCE CHARACTERISTICS:
( A ) LENGTH: 6 amino acids
( B ) TYPE: amino acid
( D ) TOPOLOGY: linear ( i x ) FEATURE:
( A ) NAME/KEY: Peptide
( B ) LOCATION: 1..6
( D ) OTHER INFORMATION: /note= "With the exception of Gly at position 5, all the amino acids are the D-amino acids."

( i x ) FEATURE:
( A ) NAME/KEY: Peptide
( B ) LOCATION: 6
( D ) OTHER INFORMATION: /note= "Amino acid is amidated at the C- terminal."

( x i ) SEQUENCE DESCRIPTION: SEQ ID NO:140:

Ile Met Thr Trp Gly Val
1               5

( 2 ) INFORMATION FOR SEQ ID NO:141:

( i ) SEQUENCE CHARACTERISTICS:
( A ) LENGTH: 6 amino acids
( B ) TYPE: amino acid
( D ) TOPOLOGY: linear ( i x ) FEATURE:
( A ) NAME/KEY: Peptide
( B ) LOCATION: 1..6
( D ) OTHER INFORMATION: /note= "With the exception of Gly at position 5, all the amino acids are the D-amino acids."

( i x ) FEATURE:
( A ) NAME/KEY: Peptide
( B ) LOCATION: 6
( D ) OTHER INFORMATION: /note= "Amino acid is amidated at the C- terminal."

( x i ) SEQUENCE DESCRIPTION: SEQ ID NO:141:

Ile Met Thr Trp Gly His
1               5

( 2 ) INFORMATION FOR SEQ ID NO:142:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "With the exception of Gly at position 5, all the amino acids are the D-amino acids."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:142:

Ile Met Thr Trp Gly Ser
1               5

( 2 ) INFORMATION FOR SEQ ID NO:143:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "With the exception of Gly at position 5, all the amino acids are the D-amino acids."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:143:

Ile Met Thr Trp Gly Arg
1               5

( 2 ) INFORMATION FOR SEQ ID NO:144:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1..6
        ( D ) OTHER INFORMATION: /note= "With the exception of Gly at position 5, all the amino acids are the D-amino acids."

( i x ) FEATURE:
        ( A ) NAME/KEY: Peptide
        ( B ) LOCATION: 6
        ( D ) OTHER INFORMATION: /note= "Amino acid is amidated at the C- terminal."

( x i ) SEQUENCE DESCRIPTION: SEQ ID NO:144:

```
    Ile Met Thr Trp Gly Lys
    1               5
```

(2) INFORMATION FOR SEQ ID NO:145:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 1..6
        (D) OTHER INFORMATION: /note= "With the exception of Gly at position 5, all the amino acids are the D-amino acids."

(ix) FEATURE:
        (A) NAME/KEY: Peptide
        (B) LOCATION: 6
        (D) OTHER INFORMATION: /note= "Amino acid is amidated at the C-terminal."

(xi) SEQUENCE DESCRIPTION: SEQ ID NO:145:

```
    Ile Met Thr Trp Gly Asn
    1               5
```

(2) INFORMATION FOR SEQ ID NO:146:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 1..6
        (D) OTHER INFORMATION: /note= "With the exception of Gly at position 5, all the amino acids are the D-amino acids."

(ix) FEATURE:
        (A) NAME/KEY: Peptide
        (B) LOCATION: 6
        (D) OTHER INFORMATION: /note= "Amino acid is amidated at the C-terminal."

(xi) SEQUENCE DESCRIPTION: SEQ ID NO:146:

```
    Ile Met Thr Trp Gly Thr
    1               5
```

(2) INFORMATION FOR SEQ ID NO:147:

(i) SEQUENCE CHARACTERISTICS:
        (A) LENGTH: 6 amino acids
        (B) TYPE: amino acid
        (D) TOPOLOGY: linear (ix) FEATURE:
        (A) NAME/KEY: Peptide
        (B) LOCATION: 1..6
        (D) OTHER INFORMATION: /note= "With the exception of Gly at position 5, all the amino acids are the D-amino acids."

(ix) FEATURE:
        (A) NAME/KEY: Peptide
        (B) LOCATION: 6
        (D) OTHER INFORMATION: /note= "Amino acid is amidated at the C-terminal."

(xi) SEQUENCE DESCRIPTION: SEQ ID NO:147:

```
    Ile Met Thr Trp Gly Gln
    1               5
```

( 2 ) INFORMATION FOR SEQ ID NO:148:

( i ) SEQUENCE CHARACTERISTICS:
       ( A ) LENGTH: 6 amino acids
       ( B ) TYPE: amino acid
       ( D ) TOPOLOGY: linear ( i x ) FEATURE:
       ( A ) NAME/KEY: Peptide
       ( B ) LOCATION: 1..6
       ( D ) OTHER INFORMATION: /note= "With the exception of Gly
           at position 5, all the amino acids are the D-amino
           acids."

( i x ) FEATURE:
       ( A ) NAME/KEY: Peptide
       ( B ) LOCATION: 6
       ( D ) OTHER INFORMATION: /note= "Amino acid is amidated at
           the C- terminal."

( x i ) SEQUENCE DESCRIPTION: SEQ ID NO:148:

Ile Met Thr Trp Gly Asp
   1               5

( 2 ) INFORMATION FOR SEQ ID NO:149:

( i ) SEQUENCE CHARACTERISTICS:
       ( A ) LENGTH: 6 amino acids
       ( B ) TYPE: amino acid
       ( D ) TOPOLOGY: linear ( i x ) FEATURE:
       ( A ) NAME/KEY: Peptide
       ( B ) LOCATION: 1..6
       ( D ) OTHER INFORMATION: /note= "With the exception of Gly
           at position 5, all the amino acids are the D-amino
           acids."

( i x ) FEATURE:
       ( A ) NAME/KEY: Peptide
       ( B ) LOCATION: 6
       ( D ) OTHER INFORMATION: /note= "Amino acid is amidated at
           the C- terminal."

( x i ) SEQUENCE DESCRIPTION: SEQ ID NO:149:

Ile Met Thr Trp Gly Glu
   1               5

( 2 ) INFORMATION FOR SEQ ID NO:150:

( i ) SEQUENCE CHARACTERISTICS:
       ( A ) LENGTH: 4 amino acids
       ( B ) TYPE: amino acid
       ( D ) TOPOLOGY: linear ( i x ) FEATURE:
       ( A ) NAME/KEY: Peptide
       ( B ) LOCATION: 2
       ( D ) OTHER INFORMATION: /note= "Xaa is (D)Nve"

( i x ) FEATURE:
       ( A ) NAME/KEY: Peptide
       ( B ) LOCATION: 4
       ( D ) OTHER INFORMATION: /note= "Xaa is Nap."

( i x ) FEATURE:
       ( A ) NAME/KEY: Peptide
       ( B ) LOCATION: 4
       ( D ) OTHER INFORMATION: /note= "Amino acid is amidated at
           the C- terminal."

( x i ) SEQUENCE DESCRIPTION: SEQ ID NO:150:

Tyr Xaa Gly Xaa ( 2 ) INFORMATION FOR SEQ ID NO:151:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 2
    ( D ) OTHER INFORMATION: /note= "Xaa is (D)Nle."

( i x ) FEATURE:
    ( A ) NAME/KEY: Peptide
    ( B ) LOCATION: 4
    ( D ) OTHER INFORMATION: /note= "Xaa is Nap."

( i x ) FEATURE:
    ( A ) NAME/KEY: Peptide
    ( B ) LOCATION: 4
    ( D ) OTHER INFORMATION: /note= "Amino acid is amidated at the C- terminal."

( x i ) SEQUENCE DESCRIPTION: SEQ ID NO:151:

Tyr Xaa Gly Xaa
1

( 2 ) INFORMATION FOR SEQ ID NO:152:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 2
    ( D ) OTHER INFORMATION: /note= "Xaa is (D)Nve."

( i x ) FEATURE:
    ( A ) NAME/KEY: Peptide
    ( B ) LOCATION: 4
    ( D ) OTHER INFORMATION: /note= "Amino acid is amidated at the C- terminal."

( x i ) SEQUENCE DESCRIPTION: SEQ ID NO:152:

Tyr Xaa Gly Trp
1

( 2 ) INFORMATION FOR SEQ ID NO:153:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 2
    ( D ) OTHER INFORMATION: /note= "Xaa is (D)Nle."

( i x ) FEATURE:
    ( A ) NAME/KEY: Peptide
    ( B ) LOCATION: 4
    ( D ) OTHER INFORMATION: /note= "Amino acid is amidated at the C- terminal."

( x i ) SEQUENCE DESCRIPTION: SEQ ID NO:153:

Tyr Xaa Gly Trp
1

( 2 ) INFORMATION FOR SEQ ID NO:154:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 2
    ( D ) OTHER INFORMATION: /note= "Xaa is (D)Nve."

( i x ) FEATURE:
    ( A ) NAME/KEY: Peptide
    ( B ) LOCATION: 4
    ( D ) OTHER INFORMATION: /note= "Amino acid is amidated at
            the C- terminal."

( x i ) SEQUENCE DESCRIPTION: SEQ ID NO:154:

Tyr  Xaa  Phe  Trp
    1

( 2 ) INFORMATION FOR SEQ ID NO:155:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 2
    ( D ) OTHER INFORMATION: /note= "Xaa is (D)Nve"

( i x ) FEATURE:
    ( A ) NAME/KEY: Peptide
    ( B ) LOCATION: 4
    ( D ) OTHER INFORMATION: /note= "Xaa is Nap."

( i x ) FEATURE:
    ( A ) NAME/KEY: Peptide
    ( B ) LOCATION: 4
    ( D ) OTHER INFORMATION: /note= "Amino acid is amidated at
            the C- terminal."

( x i ) SEQUENCE DESCRIPTION: SEQ ID NO:155:

Tyr  Xaa  Trp  Xaa
    1

( 2 ) INFORMATION FOR SEQ ID NO:156:

( i ) SEQUENCE CHARACTERISTICS:
    ( A ) LENGTH: 4 amino acids
    ( B ) TYPE: amino acid
    ( D ) TOPOLOGY: linear ( i x ) FEATURE:
    ( A ) NAME/KEY: Peptide
    ( B ) LOCATION: 2
    ( D ) OTHER INFORMATION: /note= "Xaa is (D)Nve."

( i x ) FEATURE:
    ( A ) NAME/KEY: Peptide
    ( B ) LOCATION: 4
    ( D ) OTHER INFORMATION: /note= "Amino acid is amidated at
            the C- terminal."

( x i ) SEQUENCE DESCRIPTION: SEQ ID NO:156:

Tyr  Xaa  Trp  Trp
    1

( 2 ) INFORMATION FOR SEQ ID NO:157:

( i ) SEQUENCE CHARACTERISTICS:

( A ) LENGTH: 4 amino acids
( B ) TYPE: amino acid
( D ) TOPOLOGY: linear ( i x ) FEATURE:
( A ) NAME/KEY: Peptide
( B ) LOCATION: 2
( D ) OTHER INFORMATION: /note= "Xaa is (D)Nve."

( i x ) FEATURE:
( A ) NAME/KEY: Peptide
( B ) LOCATION: 4
( D ) OTHER INFORMATION: /note= "Xaa is Nap."

( i x ) FEATURE:
( A ) NAME/KEY: Peptide
( B ) LOCATION: 4
( D ) OTHER INFORMATION: /note= "Amino acid is amidated at the C- terminal."

( x i ) SEQUENCE DESCRIPTION: SEQ ID NO:157:

Tyr Xaa Phe Xaa
1

( 2 ) INFORMATION FOR SEQ ID NO:158:

( i ) SEQUENCE CHARACTERISTICS:
( A ) LENGTH: 4 amino acids
( B ) TYPE: amino acid
( D ) TOPOLOGY: linear ( i x ) FEATURE:
( A ) NAME/KEY: Peptide
( B ) LOCATION: 2
( D ) OTHER INFORMATION: /note= "Xaa is (D)Nle."

( i x ) FEATURE:
( A ) NAME/KEY: Peptide
( B ) LOCATION: 4
( D ) OTHER INFORMATION: /note= "Amino acid is amidated at the C- terminal."

( x i ) SEQUENCE DESCRIPTION: SEQ ID NO:158:

Tyr Xaa Phe Trp
1

( 2 ) INFORMATION FOR SEQ ID NO:159:

( i ) SEQUENCE CHARACTERISTICS:
( A ) LENGTH: 4 amino acids
( B ) TYPE: amino acid
( D ) TOPOLOGY: linear ( i x ) FEATURE:
( A ) NAME/KEY: Peptide
( B ) LOCATION: 2
( D ) OTHER INFORMATION: /note= "Xaa is (D)Nle."

( i x ) FEATURE:
( A ) NAME/KEY: Peptide
( B ) LOCATION: 4
( D ) OTHER INFORMATION: /note= "Amino acid is amidated at the C- terminal."

( x i ) SEQUENCE DESCRIPTION: SEQ ID NO:159:

Tyr Xaa Trp Trp
1

( 2 ) INFORMATION FOR SEQ ID NO:160:

( i ) SEQUENCE CHARACTERISTICS:
( A ) LENGTH: 4 amino acids
( B ) TYPE: amino acid
( D ) TOPOLOGY: linear ( i x ) FEATURE:
    ( A ) NAME/KEY: Peptide
    ( B ) LOCATION: 2
    ( D ) OTHER INFORMATION: /note= "Xaa is (D)Nle."

( i x ) FEATURE:
    ( A ) NAME/KEY: Peptide
    ( B ) LOCATION: 4
    ( D ) OTHER INFORMATION: /note= "Xaa is Nap."

( i x ) FEATURE:
    ( A ) NAME/KEY: Peptide
    ( B ) LOCATION: 4
    ( D ) OTHER INFORMATION: /note= "Amino acid is amidated at the C- terminal."

( x i ) SEQUENCE DESCRIPTION: SEQ ID NO:160:

Tyr Xaa Phe Xaa
1

( 2 ) INFORMATION FOR SEQ ID NO:161:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
    ( A ) NAME/KEY: Peptide
    ( B ) LOCATION: 2
    ( D ) OTHER INFORMATION: /note= "Xaa is (D)Nle."

( i x ) FEATURE:
    ( A ) NAME/KEY: Peptide
    ( B ) LOCATION: 4
    ( D ) OTHER INFORMATION: /note= "Xaa is Nap."

( i x ) FEATURE:
    ( A ) NAME/KEY: Peptide
    ( B ) LOCATION: 4
    ( D ) OTHER INFORMATION: /note= "Amino acid is amidated at the C- terminal."

( x i ) SEQUENCE DESCRIPTION: SEQ ID NO:161:

Tyr Xaa Trp Xaa
1

( 2 ) INFORMATION FOR SEQ ID NO:162:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
    ( A ) NAME/KEY: Peptide
    ( B ) LOCATION: 1
    ( D ) OTHER INFORMATION: /note= "N-terminus is substituted with 2 methyl groups."

( i x ) FEATURE:
    ( A ) NAME/KEY: Peptide
    ( B ) LOCATION: 3
    ( D ) OTHER INFORMATION: /note= "Amino acid is amidated at the C- terminal."

( i x ) FEATURE:
    ( A ) NAME/KEY: Peptide
    ( B ) LOCATION: 1..3
    ( D ) OTHER INFORMATION: /note= "Each of the nitrogens in the peptide backbone is methylated and the carbonyls of the peptide backbone are reduced."

( x i ) SEQUENCE DESCRIPTION: SEQ ID NO:162:

```
Tyr  Tyr  Phe
1
```

( 2 ) INFORMATION FOR SEQ ID NO:163:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "N-terminus is substituted with a methyl group."

( i x ) FEATURE:
        ( A ) NAME/KEY: Peptide
        ( B ) LOCATION: 3
        ( D ) OTHER INFORMATION: /note= "Amino acid is amidated at the C- terminal."

( i x ) FEATURE:
        ( A ) NAME/KEY: Peptide
        ( B ) LOCATION: 1..3
        ( D ) OTHER INFORMATION: /note= "Each of the nitrogens in the peptide backbone is methylated and the carbonyls of the peptide backbone are reduced."

( x i ) SEQUENCE DESCRIPTION: SEQ ID NO:163:

```
Tyr  Tyr  Phe
1
```

( 2 ) INFORMATION FOR SEQ ID NO:164:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 3
        ( D ) OTHER INFORMATION: /note= "Amino acid is amidated at the C- terminal."

( i x ) FEATURE:
        ( A ) NAME/KEY: Peptide
        ( B ) LOCATION: 1..3
        ( D ) OTHER INFORMATION: /note= "Each of the nitrogens in the peptide backbone is methylated and the carbonyls of the peptide backbone are reduced."

( x i ) SEQUENCE DESCRIPTION: SEQ ID NO:164:

```
Tyr  Tyr  Phe
1
```

( 2 ) INFORMATION FOR SEQ ID NO:165:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "N-terminus is substituted with 2 methyl groups."

( i x ) FEATURE:
        ( A ) NAME/KEY: Peptide
        ( B ) LOCATION: 3
        ( D ) OTHER INFORMATION: /note= "Amino acid is amidated at the C- terminal."

( i x ) FEATURE:
    ( A ) NAME/KEY: Peptide
    ( B ) LOCATION: 1..3
    ( D ) OTHER INFORMATION: /note= "Each of the nitrogens in
        the peptide backbone is allylated and the
        carbonyls of the peptide backbone are reduced."

( x i ) SEQUENCE DESCRIPTION: SEQ ID NO:165:

Tyr Tyr Phe
1

( 2 ) INFORMATION FOR SEQ ID NO:166:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "N-terminus is substituted
            with a methyl group."

( i x ) FEATURE:
        ( A ) NAME/KEY: Peptide
        ( B ) LOCATION: 3
        ( D ) OTHER INFORMATION: /note= "Amino acid is amidated at
            the C- terminal."

( i x ) FEATURE:
        ( A ) NAME/KEY: Peptide
        ( B ) LOCATION: 1..3
        ( D ) OTHER INFORMATION: /note= "Each of the nitrogens in
            the peptide backbone is allylated and the
            carbonyls of the peptide backbone are reduced."

( x i ) SEQUENCE DESCRIPTION: SEQ ID NO:166:

Tyr Tyr Phe
1

( 2 ) INFORMATION FOR SEQ ID NO:167:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 3
        ( D ) OTHER INFORMATION: /note= "Amino acid is amidated at
            the C- terminal."

( i x ) FEATURE:
        ( A ) NAME/KEY: Peptide
        ( B ) LOCATION: 1..3
        ( D ) OTHER INFORMATION: /note= "Each of the nitrogens in
            the peptide backbone is allylated and the
            carbonyls of the peptide backbone are reduced."

( x i ) SEQUENCE DESCRIPTION: SEQ ID NO:167:

Tyr Tyr Phe
1

( 2 ) INFORMATION FOR SEQ ID NO:168:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:

(A) NAME/KEY: Peptide
(B) LOCATION: 3
(D) OTHER INFORMATION: /note= "Amino acid is amidated at the C- terminal."

(ix) FEATURE:
(A) NAME/KEY: Peptide
(B) LOCATION: 1..3
(D) OTHER INFORMATION: /note= "Each of the nitrogens in the peptide backbone is ethylated and the carbonyls of the peptide backbone are reduced."

(xi) SEQUENCE DESCRIPTION: SEQ ID NO:168:

Tyr Tyr Phe
1

(2) INFORMATION FOR SEQ ID NO:169:

(i) SEQUENCE CHARACTERISTICS:
(A) LENGTH: 3 amino acids
(B) TYPE: amino acid
(D) TOPOLOGY: linear (ix) FEATURE:
(A) NAME/KEY: Peptide
(B) LOCATION: 3
(D) OTHER INFORMATION: /note= "Amino acid is amidated at the C- terminal."

(ix) FEATURE:
(A) NAME/KEY: Peptide
(B) LOCATION: 1..3
(D) OTHER INFORMATION: /note= "Each of the nitrogens in the peptide backbone is benzylated and the carbonyls of the peptide backbone are reduced."

(xi) SEQUENCE DESCRIPTION: SEQ ID NO:169:

Tyr Tyr Phe
1

(2) INFORMATION FOR SEQ ID NO:170:

(i) SEQUENCE CHARACTERISTICS:
(A) LENGTH: 3 amino acids
(B) TYPE: amino acid
(D) TOPOLOGY: linear (ix) FEATURE:
(A) NAME/KEY: Peptide
(B) LOCATION: 3
(D) OTHER INFORMATION: /note= "Amino acid is amidated at the C- terminal."

(ix) FEATURE:
(A) NAME/KEY: Peptide
(B) LOCATION: 1..3
(D) OTHER INFORMATION: /note= "Each of the nitrogens in the peptide backbone is naphthylated and the carbonyls of the peptide backbone are reduced."

(xi) SEQUENCE DESCRIPTION: SEQ ID NO:170:

Tyr Tyr Phe
1

(2) INFORMATION FOR SEQ ID NO:171:

(i) SEQUENCE CHARACTERISTICS:
(A) LENGTH: 3 amino acids
(B) TYPE: amino acid
(D) TOPOLOGY: linear (ix) FEATURE:
(A) NAME/KEY: Peptide
(B) LOCATION: 1

(D) OTHER INFORMATION: /note= "N-terminus is substituted with 2 methyl groups."

(ix) FEATURE:
  (A) NAME/KEY: Peptide
  (B) LOCATION: 3
  (D) OTHER INFORMATION: /note= "Amino acid is amidated at the C- terminal."

(ix) FEATURE:
  (A) NAME/KEY: Peptide
  (B) LOCATION: 1..3
  (D) OTHER INFORMATION: /note= "Each of the nitrogens in the peptide backbone is methylated."

(xi) SEQUENCE DESCRIPTION: SEQ ID NO:171:

Tyr Tyr Phe
1

(2) INFORMATION FOR SEQ ID NO:172:

(i) SEQUENCE CHARACTERISTICS:
  (A) LENGTH: 3 amino acids
  (B) TYPE: amino acid
  (D) TOPOLOGY: linear (ix) FEATURE:
  (A) NAME/KEY: Peptide
  (B) LOCATION: 1
  (D) OTHER INFORMATION: /note= "N-terminus is substituted with a methyl group."

(ix) FEATURE:
  (A) NAME/KEY: Peptide
  (B) LOCATION: 3
  (D) OTHER INFORMATION: /note= "Amino acid is amidated at the C- terminal."

(ix) FEATURE:
  (A) NAME/KEY: Peptide
  (B) LOCATION: 1..3
  (D) OTHER INFORMATION: /note= "Each of the nitrogens in the peptide backbone is methylated."

(xi) SEQUENCE DESCRIPTION: SEQ ID NO:172:

Tyr Tyr Phe
1

(2) INFORMATION FOR SEQ ID NO:173:

(i) SEQUENCE CHARACTERISTICS:
  (A) LENGTH: 3 amino acids
  (B) TYPE: amino acid
  (D) TOPOLOGY: linear (ix) FEATURE:
  (A) NAME/KEY: Peptide
  (B) LOCATION: 3
  (D) OTHER INFORMATION: /note= "Amino acid is amidated at the C- terminal."

(ix) FEATURE:
  (A) NAME/KEY: Peptide
  (B) LOCATION: 1..3
  (D) OTHER INFORMATION: /note= "Each of the nitrogens in the peptide backbone is methylated."

(xi) SEQUENCE DESCRIPTION: SEQ ID NO:173:

Tyr Tyr Phe
1

(2) INFORMATION FOR SEQ ID NO:174:

(i) SEQUENCE CHARACTERISTICS:

(A) LENGTH: 3 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note= "N-terminus is substituted
                with 2 methyl groups."

(ix) FEATURE:
            (A) NAME/KEY: Peptide
            (B) LOCATION: 3
            (D) OTHER INFORMATION: /note= "Amino acid is amidated at
                the C- terminal."

(ix) FEATURE:
            (A) NAME/KEY: Peptide
            (B) LOCATION: 1..3
            (D) OTHER INFORMATION: /note= "Each of the nitrogens in
                the peptide backbone is allylated."

(xi) SEQUENCE DESCRIPTION: SEQ ID NO:174:

Tyr  Tyr  Phe
    1

(2) INFORMATION FOR SEQ ID NO:175:

(i) SEQUENCE CHARACTERISTICS:
            (A) LENGTH: 3 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note= "N-terminus is substituted
                with a methyl group."

(ix) FEATURE:
            (A) NAME/KEY: Peptide
            (B) LOCATION: 3
            (D) OTHER INFORMATION: /note= "Amino acid is amidated at
                the C- terminal."

(ix) FEATURE:
            (A) NAME/KEY: Peptide
            (B) LOCATION: 1..3
            (D) OTHER INFORMATION: /note= "Each of the nitrogens in
                the peptide backbone is allylated."

(xi) SEQUENCE DESCRIPTION: SEQ ID NO:175:

Tyr  Tyr  Phe
    1

(2) INFORMATION FOR SEQ ID NO:176:

(i) SEQUENCE CHARACTERISTICS:
            (A) LENGTH: 3 amino acids
            (B) TYPE: amino acid
            (D) TOPOLOGY: linear (ix) FEATURE:
            (A) NAME/KEY: Peptide
            (B) LOCATION: 3
            (D) OTHER INFORMATION: /note= "Amino acid is amidated at
                the C- terminal."

(ix) FEATURE:
            (A) NAME/KEY: Peptide
            (B) LOCATION: 1..3
            (D) OTHER INFORMATION: /note= "Each of the nitrogens in
                the peptide backbone is allylated."

(xi) SEQUENCE DESCRIPTION: SEQ ID NO:176:

Tyr   Tyr   Phe
1

( 2 ) INFORMATION FOR SEQ ID NO:177:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 1..3
        ( D ) OTHER INFORMATION: /note= "Each of the nitrogens in
            the peptide backbone is ethylated."

( i x ) FEATURE:
        ( A ) NAME/KEY: Peptide
        ( B ) LOCATION: 3
        ( D ) OTHER INFORMATION: /note= "Amino acid is amidated at
            the C- terminal."

( x i ) SEQUENCE DESCRIPTION: SEQ ID NO:177:

Tyr   Tyr   Phe
1

( 2 ) INFORMATION FOR SEQ ID NO:178:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 1..3
        ( D ) OTHER INFORMATION: /note= "Each of the nitrogens in
            the peptide backbone is benzylated."

( i x ) FEATURE:
        ( A ) NAME/KEY: Peptide
        ( B ) LOCATION: 3
        ( D ) OTHER INFORMATION: /note= "Amino acid is amidated at
            the C- terminal."

( x i ) SEQUENCE DESCRIPTION: SEQ ID NO:178:

Tyr   Tyr   Phe
1

( 2 ) INFORMATION FOR SEQ ID NO:179:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 1..3
        ( D ) OTHER INFORMATION: /note= "Each of the nitrogens in
            the peptide backbone is napthylated."

( i x ) FEATURE:
        ( A ) NAME/KEY: Peptide
        ( B ) LOCATION: 3
        ( D ) OTHER INFORMATION: /note= "Amino acid is amidated at
            the C- terminal."

( x i ) SEQUENCE DESCRIPTION: SEQ ID NO:179:

Tyr   Tyr   Phe
1

( 2 ) INFORMATION FOR SEQ ID NO:180:

(i) SEQUENCE CHARACTERISTICS:
  (A) LENGTH: 4 amino acids
  (B) TYPE: amino acid
  (D) TOPOLOGY: linear (ix) FEATURE:
  (A) NAME/KEY: Peptide
  (B) LOCATION: 1
  (D) OTHER INFORMATION: /note= "The N-terminus is substituted with two methyl groups."

(ix) FEATURE:
  (A) NAME/KEY: Peptide
  (B) LOCATION: 1..4
  (D) OTHER INFORMATION: /note= "Each of the nitrogens in the peptide backbone is methylated and the carbonyls of the peptide backbone are reduced."

(ix) FEATURE:
  (A) NAME/KEY: Peptide
  (B) LOCATION: 4
  (D) OTHER INFORMATION: /note= "Amino acid is amidated at the C- terminal."

(xi) SEQUENCE DESCRIPTION: SEQ ID NO:180:

Tyr Tyr Phe Pro
1

(2) INFORMATION FOR SEQ ID NO:181:

(i) SEQUENCE CHARACTERISTICS:
  (A) LENGTH: 4 amino acids
  (B) TYPE: amino acid
  (D) TOPOLOGY: linear (ix) FEATURE:
  (A) NAME/KEY: Peptide
  (B) LOCATION: 1
  (D) OTHER INFORMATION: /note= "The N-terminus is substituted with a methyl group."

(ix) FEATURE:
  (A) NAME/KEY: Peptide
  (B) LOCATION: 1..4
  (D) OTHER INFORMATION: /note= "Each of the nitrogens in the peptide backbone is methylated and the carbonyls in the peptide backbone are reduced."

(ix) FEATURE:
  (A) NAME/KEY: Peptide
  (B) LOCATION: 4
  (D) OTHER INFORMATION: /note= "Amino acid is amidated at the C- terminal."

(xi) SEQUENCE DESCRIPTION: SEQ ID NO:181:

Tyr Tyr Phe Pro
1

(2) INFORMATION FOR SEQ ID NO:182:

(i) SEQUENCE CHARACTERISTICS:
  (A) LENGTH: 4 amino acids
  (B) TYPE: amino acid
  (D) TOPOLOGY: linear (ix) FEATURE:
  (A) NAME/KEY: Peptide
  (B) LOCATION: 1..4
  (D) OTHER INFORMATION: /note= "Each of the nitrogens in the peptide backbone is methylated and the carbonyls in the peptide backbone are reduced."

(ix) FEATURE:
  (A) NAME/KEY: Peptide
  (B) LOCATION: 4

( D ) OTHER INFORMATION: /note= "Amino acid is amidated at
the C- terminal."

( x i ) SEQUENCE DESCRIPTION: SEQ ID NO:182:

Tyr Tyr Phe Pro
1

( 2 ) INFORMATION FOR SEQ ID NO:183:

( i ) SEQUENCE CHARACTERISTICS:
( A ) LENGTH: 4 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note= "N-terminus is substituted
with 2 methyl groups."

( i x ) FEATURE:
( A ) NAME/KEY: Peptide
( B ) LOCATION: 1..4
( D ) OTHER INFORMATION: /note= "Each of the nitrogens in
the peptide backbone is allylated and the
carbonyls of the peptide backbone are reduced."

( i x ) FEATURE:
( A ) NAME/KEY: Peptide
( B ) LOCATION: 4
( D ) OTHER INFORMATION: /note= "Amino acid is amidated at
the C- terminal."

( x i ) SEQUENCE DESCRIPTION: SEQ ID NO:183:

Tyr Tyr Phe Pro
1

( 2 ) INFORMATION FOR SEQ ID NO:184:

( i ) SEQUENCE CHARACTERISTICS:
( A ) LENGTH: 4 amino acids
( B ) TYPE: amino acid
( D ) TOPOLOGY: linear ( i x ) FEATURE:
( A ) NAME/KEY: Peptide
( B ) LOCATION: 1
( D ) OTHER INFORMATION: /note= "The N-terminus is
substituted with a methyl group."

( i x ) FEATURE:
( A ) NAME/KEY: Peptide
( B ) LOCATION: 1..4
( D ) OTHER INFORMATION: /note= "Each of the nitrogens in
the peptide backbone is allylated and the
carbonyls of the peptide backbone are reduced."

( i x ) FEATURE:
( A ) NAME/KEY: Peptide
( B ) LOCATION: 4
( D ) OTHER INFORMATION: /note= "Amino acid is amidated at
the C- terminal."

( x i ) SEQUENCE DESCRIPTION: SEQ ID NO:184:

Tyr Tyr Phe Pro
1

( 2 ) INFORMATION FOR SEQ ID NO:185:

( i ) SEQUENCE CHARACTERISTICS:
( A ) LENGTH: 4 amino acids
( B ) TYPE: amino acid
( D ) TOPOLOGY: linear ( i x ) FEATURE:
    ( A ) NAME/KEY: Peptide
    ( B ) LOCATION: 1..4
    ( D ) OTHER INFORMATION: /note= "Each nitrogen in the peptide backbone is allylated and the carbonyls of the peptide backbone are reduced."

( i x ) FEATURE:
    ( A ) NAME/KEY: Peptide
    ( B ) LOCATION: 4
    ( D ) OTHER INFORMATION: /note= "Amino acid is amidated at the C- terminal."

( x i ) SEQUENCE DESCRIPTION: SEQ ID NO:185:

Tyr Tyr Phe Pro
1

( 2 ) INFORMATION FOR SEQ ID NO:186:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1..4
        ( D ) OTHER INFORMATION: /note= "Each nitrogen in the peptide backbone is ethylated and the carbonyls of the peptide backbone are reduced."

( i x ) FEATURE:
        ( A ) NAME/KEY: Peptide
        ( B ) LOCATION: 4
        ( D ) OTHER INFORMATION: /note= "Amino acid is amidated at the C- terminal."

( x i ) SEQUENCE DESCRIPTION: SEQ ID NO:186:

Tyr Tyr Phe Pro
1

( 2 ) INFORMATION FOR SEQ ID NO:187:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1..4
        ( D ) OTHER INFORMATION: /note= "Each nitrogen in the peptide backbone is benzylated and the carbonyls of the peptide backbone are reduced."

( i x ) FEATURE:
        ( A ) NAME/KEY: Peptide
        ( B ) LOCATION: 4
        ( D ) OTHER INFORMATION: /note= "Amino acid is amidated at the C- terminal."

( x i ) SEQUENCE DESCRIPTION: SEQ ID NO:187:

Tyr Tyr Phe Pro
1

( 2 ) INFORMATION FOR SEQ ID NO:188:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide ( B ) LOCATION: 1..4
( D ) OTHER INFORMATION: /note= "Each nitrogen in the
peptide backbone is naphthylated and the carbonyls
of the peptide backbone are reduced."

( i x ) FEATURE:
    ( A ) NAME/KEY: Peptide
    ( B ) LOCATION: 4
    ( D ) OTHER INFORMATION: /note= "Amino acid is amidated at
        the C- terminal."

( x i ) SEQUENCE DESCRIPTION: SEQ ID NO:188:

Tyr Tyr Phe Pro
1

( 2 ) INFORMATION FOR SEQ ID NO:189:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "The N-terminus is
            substituted with two methyl groups."

( i x ) FEATURE:
        ( A ) NAME/KEY: Peptide
        ( B ) LOCATION: 1..4
        ( D ) OTHER INFORMATION: /note= "Each of the nitrogens in
            the peptide backbone is methylated."

( i x ) FEATURE:
        ( A ) NAME/KEY: Peptide
        ( B ) LOCATION: 4
        ( D ) OTHER INFORMATION: /note= "Amino acid is amidated at
            the C- terminal."

( x i ) SEQUENCE DESCRIPTION: SEQ ID NO:189:

Tyr Tyr Phe Pro
1

( 2 ) INFORMATION FOR SEQ ID NO:190:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "The N-terminus is
            substituted with a methyl group."

( i x ) FEATURE:
        ( A ) NAME/KEY: Peptide
        ( B ) LOCATION: 1..4
        ( D ) OTHER INFORMATION: /note= "Each of the nitrogens in
            the peptide backbone is methylated."

( i x ) FEATURE:
        ( A ) NAME/KEY: Peptide
        ( B ) LOCATION: 4
        ( D ) OTHER INFORMATION: /note= "Amino acid is amidated at
            the C- terminal."

( x i ) SEQUENCE DESCRIPTION: SEQ ID NO:190:

Tyr Tyr Phe Pro
1

( 2 ) INFORMATION FOR SEQ ID NO:191:

( i ) SEQUENCE CHARACTERISTICS:
  ( A ) LENGTH: 4 amino acids
  ( B ) TYPE: amino acid
  ( D ) TOPOLOGY: linear ( i x ) FEATURE:
  ( A ) NAME/KEY: Peptide
  ( B ) LOCATION: 1..4
  ( D ) OTHER INFORMATION: /note= "Each of the nitrogens in the peptide backbone is methylated."

( i x ) FEATURE:
  ( A ) NAME/KEY: Peptide
  ( B ) LOCATION: 4
  ( D ) OTHER INFORMATION: /note= "Amino acid is amidated at the C- terminal."

( x i ) SEQUENCE DESCRIPTION: SEQ ID NO:191:

Tyr  Tyr  Phe  Pro
1

( 2 ) INFORMATION FOR SEQ ID NO:192:

( i ) SEQUENCE CHARACTERISTICS:
  ( A ) LENGTH: 4 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note= "N-terminus is substituted with 2 methyl groups."

( i x ) FEATURE:
  ( A ) NAME/KEY: Peptide
  ( B ) LOCATION: 1..4
  ( D ) OTHER INFORMATION: /note= "Each of the nitrogens in the peptide backbone is allylated."

( i x ) FEATURE:
  ( A ) NAME/KEY: Peptide
  ( B ) LOCATION: 4
  ( D ) OTHER INFORMATION: /note= "Amino acid is amidated at the C- terminal."

( x i ) SEQUENCE DESCRIPTION: SEQ ID NO:192:

Tyr  Tyr  Phe  Pro
1

( 2 ) INFORMATION FOR SEQ ID NO:193:

( i ) SEQUENCE CHARACTERISTICS:
  ( A ) LENGTH: 4 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note= "The N-terminus is substituted with a methyl group."

( i x ) FEATURE:
  ( A ) NAME/KEY: Peptide
  ( B ) LOCATION: 1..4
  ( D ) OTHER INFORMATION: /note= "Each of the nitrogens in the peptide backbone is allylated."

( i x ) FEATURE:
  ( A ) NAME/KEY: Peptide
  ( B ) LOCATION: 4
  ( D ) OTHER INFORMATION: /note= "Amino acid is amidated at the C- terminal."

( x i ) SEQUENCE DESCRIPTION: SEQ ID NO:193:

Tyr Tyr Phe Pro
1

( 2 ) INFORMATION FOR SEQ ID NO:194:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1..4
        ( D ) OTHER INFORMATION: /note= "Each of the nitrogens in the peptide backbone is allylated."

( i x ) FEATURE:
        ( A ) NAME/KEY: Peptide
        ( B ) LOCATION: 4
        ( D ) OTHER INFORMATION: /note= "Amino acid is amidated at the C- terminal."

( x i ) SEQUENCE DESCRIPTION: SEQ ID NO:194:

Tyr Tyr Phe Pro
1

( 2 ) INFORMATION FOR SEQ ID NO:195:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1..4
        ( D ) OTHER INFORMATION: /note= "Each of the nitrogens in the peptide backbone is ethylated."

( i x ) FEATURE:
        ( A ) NAME/KEY: Peptide
        ( B ) LOCATION: 4
        ( D ) OTHER INFORMATION: /note= "Amino acid is amidated at the C- terminal."

( x i ) SEQUENCE DESCRIPTION: SEQ ID NO:195:

Tyr Tyr Phe Pro
1

( 2 ) INFORMATION FOR SEQ ID NO:196:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1..4
        ( D ) OTHER INFORMATION: /note= "Each of the nitrogens in the peptide backbone is benzylated."

( i x ) FEATURE:
        ( A ) NAME/KEY: Peptide
        ( B ) LOCATION: 4
        ( D ) OTHER INFORMATION: /note= "Amino acid is amidated at the C- terminal."

( x i ) SEQUENCE DESCRIPTION: SEQ ID NO:196:

Tyr Tyr Phe Pro
1

( 2 ) INFORMATION FOR SEQ ID NO:197:

( i ) SEQUENCE CHARACTERISTICS:
        ( A ) LENGTH: 4 amino acids
        ( B ) TYPE: amino acid
        ( D ) TOPOLOGY: linear ( i x ) FEATURE:
        ( A ) NAME/KEY: Peptide
        ( B ) LOCATION: 1..4
        ( D ) OTHER INFORMATION: /note= "Each of the nitrogens in
            the peptide backbone is naphthylated."

( i x ) FEATURE:
        ( A ) NAME/KEY: Peptide
        ( B ) LOCATION: 4
        ( D ) OTHER INFORMATION: /note= "Amino acid is amidated at
            the C- terminal."

( x i ) SEQUENCE DESCRIPTION: SEQ ID NO:197:

Tyr Tyr Phe Pro
1

( 2 ) INFORMATION FOR SEQ ID NO:198:

( i ) SEQUENCE CHARACTERISTICS:
        ( A ) LENGTH: 2 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "N-terminus is substituted
            with 2 methyl groups."

( i x ) FEATURE:
        ( A ) NAME/KEY: Peptide
        ( B ) LOCATION: 2
        ( D ) OTHER INFORMATION: /note= "Amino acid is amidated at
            the C- terminal."

( i x ) FEATURE:
        ( A ) NAME/KEY: Peptide
        ( B ) LOCATION: 1..2
        ( D ) OTHER INFORMATION: /note= "Each of the nitrogens in
            the peptide backbone is methylated and the
            carbonyls of the peptide backbone are reduced."

( x i ) SEQUENCE DESCRIPTION: SEQ ID NO:198:

Tyr Tyr
1

( 2 ) INFORMATION FOR SEQ ID NO:199:

( i ) SEQUENCE CHARACTERISTICS:
        ( A ) LENGTH: 2 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "N-terminus has a methyl
            group."

( i x ) FEATURE:
        ( A ) NAME/KEY: Peptide
        ( B ) LOCATION: 1..2
        ( D ) OTHER INFORMATION: /note= "Each of the nitrogens in
            the peptide backbone is methylated and the
            carbonyls in the peptide backbone are reduced."

( i x ) FEATURE:
        ( A ) NAME/KEY: Peptide (B) LOCATION: 2
(D) OTHER INFORMATION: /note= "Amino acid is amidated at
the C- terminal."

(xi) SEQUENCE DESCRIPTION: SEQ ID NO:199:

Tyr Tyr
1

(2) INFORMATION FOR SEQ ID NO:200:

(i) SEQUENCE CHARACTERISTICS:
(A) LENGTH: 2 amino acids
(B) TYPE: amino acid
(D) TOPOLOGY: linear (ix) FEATURE:
(A) NAME/KEY: Peptide
(B) LOCATION: 1..2
(D) OTHER INFORMATION: /note= "Each of the nitrogens in
the peptide backbone is methylated and the
carbonyls of the peptide backbone are reduced."

(ix) FEATURE:
(A) NAME/KEY: Peptide
(B) LOCATION: 2
(D) OTHER INFORMATION: /note= "Amino acid is amidated at
the C- terminal."

(xi) SEQUENCE DESCRIPTION: SEQ ID NO:200:

Tyr Tyr
1

(2) INFORMATION FOR SEQ ID NO:201:

(i) SEQUENCE CHARACTERISTICS:
(A) LENGTH: 2 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "N-terminus is substituted
with 2 methyl groups."

(ix) FEATURE:
(A) NAME/KEY: Peptide
(B) LOCATION: 2
(D) OTHER INFORMATION: /note= "Amino acid is amidated at
the C- terminal."

(ix) FEATURE:
(A) NAME/KEY: Peptide
(B) LOCATION: 1..2
(D) OTHER INFORMATION: /note= "Each of the carbonyls of
the peptide backbone is reduced."

(ix) FEATURE:
(A) NAME/KEY: Peptide
(B) LOCATION: 1
(D) OTHER INFORMATION: /note= "The amine in the peptide
backbone is methylated (NMe)."

(ix) FEATURE:
(A) NAME/KEY: Peptide
(B) LOCATION: 2
(D) OTHER INFORMATION: /note= "The amine in the peptide
backbone is benzylated (NHBzl)."

(xi) SEQUENCE DESCRIPTION: SEQ ID NO:201:

Tyr Tyr
1

(2) INFORMATION FOR SEQ ID NO:202:

( i ) SEQUENCE CHARACTERISTICS:
  ( A ) LENGTH: 2 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note= "N-terminus has a methyl group."

( i x ) FEATURE:
  ( A ) NAME/KEY: Peptide
  ( B ) LOCATION: 1..2
  ( D ) OTHER INFORMATION: /note= "Each of the carbonyls in the peptide backbone is reduced."

( i x ) FEATURE:
  ( A ) NAME/KEY: Peptide
  ( B ) LOCATION: 2
  ( D ) OTHER INFORMATION: /note= "Amino acid is amidated at the C- terminal."

( i x ) FEATURE:
  ( A ) NAME/KEY: Peptide
  ( B ) LOCATION: 1
  ( D ) OTHER INFORMATION: /note= "The amine in the peptide backbone is methylated (NMe)."

( i x ) FEATURE:
  ( A ) NAME/KEY: Peptide
  ( B ) LOCATION: 2
  ( D ) OTHER INFORMATION: /note= "The amine in the peptide backbone is benzylated (NHBzl)."

( x i ) SEQUENCE DESCRIPTION: SEQ ID NO:202:

Tyr Tyr
1

( 2 ) INFORMATION FOR SEQ ID NO:203:

( i ) SEQUENCE CHARACTERISTICS:
  ( A ) LENGTH: 2 amino acids
  ( B ) TYPE: amino acid
  ( D ) TOPOLOGY: linear ( i x ) FEATURE:
  ( A ) NAME/KEY: Peptide
  ( B ) LOCATION: 1..2
  ( D ) OTHER INFORMATION: /note= "Each of the carbonyls of the peptide backbone is reduced."

( i x ) FEATURE:
  ( A ) NAME/KEY: Peptide
  ( B ) LOCATION: 2
  ( D ) OTHER INFORMATION: /note= "Amino acid is amidated at the C- terminal."

( i x ) FEATURE:
  ( A ) NAME/KEY: Peptide
  ( B ) LOCATION: 1
  ( D ) OTHER INFORMATION: /note= "The amine in the peptide backbone is methylated (NMe)."

( i x ) FEATURE:
  ( A ) NAME/KEY: Peptide
  ( B ) LOCATION: 2
  ( D ) OTHER INFORMATION: /note= "The amine in the peptide backbone is benzylated (NHBzl)."

( x i ) SEQUENCE DESCRIPTION: SEQ ID NO:203:

Tyr Tyr
1

( 2 ) INFORMATION FOR SEQ ID NO:204:

( i ) SEQUENCE CHARACTERISTICS:
    ( A ) LENGTH: 2 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "N-terminus is substituted with 2 methyl groups."

( i x ) FEATURE:
    ( A ) NAME/KEY: Peptide
    ( B ) LOCATION: 2
    ( D ) OTHER INFORMATION: /note= "Amino acid is amidated at the C- terminal."

( i x ) FEATURE:
    ( A ) NAME/KEY: Peptide
    ( B ) LOCATION: 1..2
    ( D ) OTHER INFORMATION: /note= "Each of the nitrogens in the peptide backbone is methylated and the carbonyls of the peptide backbone are reduced."

( i x ) FEATURE:
    ( A ) NAME/KEY: Peptide
    ( B ) LOCATION: 1
    ( D ) OTHER INFORMATION: /note= "One amine in the peptide backbone is benzylated (NHBzl)."

( i x ) FEATURE:
    ( A ) NAME/KEY: Peptide
    ( B ) LOCATION: 2
    ( D ) OTHER INFORMATION: /note= "One amine in the peptide backbone is methylated (NHMe)."

( x i ) SEQUENCE DESCRIPTION: SEQ ID NO:204:

Tyr Tyr
1

( 2 ) INFORMATION FOR SEQ ID NO:205:

( i ) SEQUENCE CHARACTERISTICS:
    ( A ) LENGTH: 2 amino acids
    ( B ) TYPE: amino acid
    ( D ) TOPOLOGY: linear ( i x ) FEATURE:
    ( A ) NAME/KEY: Peptide
    ( B ) LOCATION: 1
    ( D ) OTHER INFORMATION: /note= "N-terminus has a methyl group."

( i x ) FEATURE:
    ( A ) NAME/KEY: Peptide
    ( B ) LOCATION: 1..2
    ( D ) OTHER INFORMATION: /note= "Each of the carbonyls in the peptide backbone is reduced."

( i x ) FEATURE:
    ( A ) NAME/KEY: Peptide
    ( B ) LOCATION: 2
    ( D ) OTHER INFORMATION: /note= "Amino acid is amidated at the C- terminal."

( i x ) FEATURE:
    ( A ) NAME/KEY: Peptide
    ( B ) LOCATION: 1
    ( D ) OTHER INFORMATION: /note= "One amine in the peptide backbone is benzylated (NHBzl)."

( i x ) FEATURE:
    ( A ) NAME/KEY: Peptide
    ( B ) LOCATION: 2
    ( D ) OTHER INFORMATION: /note= "One amine in the peptide backbone is methylated (NMe)."

( x i ) SEQUENCE DESCRIPTION: SEQ ID NO:205:

Tyr Tyr
1

( 2 ) INFORMATION FOR SEQ ID NO:206:

( i ) SEQUENCE CHARACTERISTICS:
        ( A ) LENGTH: 2 amino acids
        ( B ) TYPE: amino acid
        ( D ) TOPOLOGY: linear ( i x ) FEATURE:
        ( A ) NAME/KEY: Peptide
        ( B ) LOCATION: 1..2
        ( D ) OTHER INFORMATION: /note= "Each of the carbonyls of
            the peptide backbone is reduced."

( i x ) FEATURE:
        ( A ) NAME/KEY: Peptide
        ( B ) LOCATION: 2
        ( D ) OTHER INFORMATION: /note= "Amino acid is amidated at
            the C- terminal."

( i x ) FEATURE:
        ( A ) NAME/KEY: Peptide
        ( B ) LOCATION: 1
        ( D ) OTHER INFORMATION: /note= "One amine in the peptide
            backbone is benzylated (NHBzl)."

( i x ) FEATURE:
        ( A ) NAME/KEY: Peptide
        ( B ) LOCATION: 2
        ( D ) OTHER INFORMATION: /note= "One amine in the peptide
            backbone is methylated (NHMe)."

( x i ) SEQUENCE DESCRIPTION: SEQ ID NO:206:

Tyr Tyr
1

( 2 ) INFORMATION FOR SEQ ID NO:207:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "N-terminus is substituted
            with 2 methyl groups."

( i x ) FEATURE:
        ( A ) NAME/KEY: Peptide
        ( B ) LOCATION: 3
        ( D ) OTHER INFORMATION: /note= "Amino acid is amidated at
            the C- terminal."

( i x ) FEATURE:
        ( A ) NAME/KEY: Peptide
        ( B ) LOCATION: 1..3
        ( D ) OTHER INFORMATION: /note= "Each of the nitrogens in
            the peptide backbone is methylated and the
            carbonyls of the peptide backbone are reduced."

( i x ) FEATURE:
        ( A ) NAME/KEY: Peptide
        ( B ) LOCATION: 3
        ( D ) OTHER INFORMATION: /note= "Phe is the D-form of the
            amino acid."

( x i ) SEQUENCE DESCRIPTION: SEQ ID NO:207:

Tyr Tyr Phe
1

( 2 ) INFORMATION FOR SEQ ID NO:208:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "N-terminus is substituted with 2 methyl groups."

( i x ) FEATURE:
        ( A ) NAME/KEY: Peptide
        ( B ) LOCATION: 3
        ( D ) OTHER INFORMATION: /note= "Amino acid is amidated at the C- terminal."

( i x ) FEATURE:
        ( A ) NAME/KEY: Peptide
        ( B ) LOCATION: 1..3
        ( D ) OTHER INFORMATION: /note= "Each of the nitrogens in the peptide backbone is methylated and the carbonyls of the peptide backbone are reduced."

( i x ) FEATURE:
        ( A ) NAME/KEY: Peptide
        ( B ) LOCATION: 2
        ( D ) OTHER INFORMATION: /note= "Tyr is the D-form of the amino acid."

( x i ) SEQUENCE DESCRIPTION: SEQ ID NO:208:

Tyr   Tyr   Phe
    1

( 2 ) INFORMATION FOR SEQ ID NO:209:

( i ) SEQUENCE CHARACTERISTICS:
        ( A ) LENGTH: 3 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "N-terminus is substituted with 2 methyl groups."

( i x ) FEATURE:
        ( A ) NAME/KEY: Peptide
        ( B ) LOCATION: 3
        ( D ) OTHER INFORMATION: /note= "Amino acid is amidated at the C- terminal."

( i x ) FEATURE:
        ( A ) NAME/KEY: Peptide
        ( B ) LOCATION: 1..3
        ( D ) OTHER INFORMATION: /note= "Each of the nitrogens in the peptide backbone is methylated and the carbonyls of the peptide backbone are reduced."

( i x ) FEATURE:
        ( A ) NAME/KEY: Peptide
        ( B ) LOCATION: 1
        ( D ) OTHER INFORMATION: /note= "Tyr is the D-form of the amino acid."

( x i ) SEQUENCE DESCRIPTION: SEQ ID NO:209:

Tyr   Tyr   Phe
    1

( 2 ) INFORMATION FOR SEQ ID NO:210:

( i ) SEQUENCE CHARACTERISTICS:

(A) LENGTH: 3 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note= "N-terminus is substituted
                with 2 methyl groups."

(ix) FEATURE:
            (A) NAME/KEY: Peptide
            (B) LOCATION: 3
            (D) OTHER INFORMATION: /note= "Amino acid is amidated at
                the C- terminal."

(ix) FEATURE:
            (A) NAME/KEY: Peptide
            (B) LOCATION: 1..3
            (D) OTHER INFORMATION: /note= "Each of the nitrogens in
                the peptide backbone is methylated and the
                carbonyls of the peptide backbone are reduced."

(ix) FEATURE:
            (A) NAME/KEY: Peptide
            (B) LOCATION: 1..3
            (D) OTHER INFORMATION: /note= "All amino acids are the
                D-form."

(xi) SEQUENCE DESCRIPTION: SEQ ID NO:210:

Tyr  Tyr  Phe
1

(2) INFORMATION FOR SEQ ID NO:211:

(i) SEQUENCE CHARACTERISTICS:
            (A) LENGTH: 3 amino acids
            (B) TYPE: amino acid
            (D) TOPOLOGY: linear (ix) FEATURE:
            (A) NAME/KEY: Peptide
            (B) LOCATION: 1
            (D) OTHER INFORMATION: /note= "N-terminus is substituted
                with 2 methyl groups."

(ix) FEATURE:
            (A) NAME/KEY: Peptide
            (B) LOCATION: 3
            (D) OTHER INFORMATION: /note= "Amino acid is amidated at
                the C- terminal."

(ix) FEATURE:
            (A) NAME/KEY: Peptide
            (B) LOCATION: 1..3
            (D) OTHER INFORMATION: /note= "Each of the nitrogens in
                the peptide backbone is methylated and the
                carbonyls of the peptide backbone are reduced."

(ix) FEATURE:
            (A) NAME/KEY: Peptide
            (B) LOCATION: 1
            (D) OTHER INFORMATION: /note= "Tyr is the D-form of the
                amino acid."

(ix) FEATURE:
            (A) NAME/KEY: Peptide
            (B) LOCATION: 2
            (D) OTHER INFORMATION: /note= "Tyr is the D-form of the
                amino acid."

(xi) SEQUENCE DESCRIPTION: SEQ ID NO:211:

Tyr  Tyr  Phe
1

(2) INFORMATION FOR SEQ ID NO:212:

( i ) SEQUENCE CHARACTERISTICS:
  ( A ) LENGTH: 3 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note= "N-terminus is substituted
    with 2 methyl groups."

( i x ) FEATURE:
  ( A ) NAME/KEY: Peptide
  ( B ) LOCATION: 3
  ( D ) OTHER INFORMATION: /note= "Amino acid is amidated at
    the C- terminal."

( i x ) FEATURE:
  ( A ) NAME/KEY: Peptide
  ( B ) LOCATION: 1..3
  ( D ) OTHER INFORMATION: /note= "Each of the nitrogens in
    the peptide backbone is methylated and the
    carbonyls of the peptide backbone are reduced."

( i x ) FEATURE:
  ( A ) NAME/KEY: Peptide
  ( B ) LOCATION: 2
  ( D ) OTHER INFORMATION: /note= "Tyr is the D-form of the
    amino acid."

( i x ) FEATURE:
  ( A ) NAME/KEY: Peptide
  ( B ) LOCATION: 3
  ( D ) OTHER INFORMATION: /note= "Phe is the D-form of the
    amino acid."

( x i ) SEQUENCE DESCRIPTION: SEQ ID NO:212:

Tyr Tyr Phe
1

( 2 ) INFORMATION FOR SEQ ID NO:213:

( i ) SEQUENCE CHARACTERISTICS:
  ( A ) LENGTH: 3 amino acids
  ( B ) TYPE: amino acid
  ( D ) TOPOLOGY: linear ( i x ) FEATURE:
  ( A ) NAME/KEY: Peptide
  ( B ) LOCATION: 1
  ( D ) OTHER INFORMATION: /note= "N-terminus is substituted
    with 2 methyl groups."

( i x ) FEATURE:
  ( A ) NAME/KEY: Peptide
  ( B ) LOCATION: 3
  ( D ) OTHER INFORMATION: /note= "Amino acid is amidated at
    the C- terminal."

( i x ) FEATURE:
  ( A ) NAME/KEY: Peptide
  ( B ) LOCATION: 1..3
  ( D ) OTHER INFORMATION: /note= "Each of the nitrogens in
    the peptide backbone is methylated and the
    carbonyls of the peptide backbone are reduced."

( i x ) FEATURE:
  ( A ) NAME/KEY: Peptide
  ( B ) LOCATION: 1
  ( D ) OTHER INFORMATION: /note= "Tyr is the D-form of the
    amino acid."

( i x ) FEATURE:
  ( A ) NAME/KEY: Peptide
  ( B ) LOCATION: 3
  ( D ) OTHER INFORMATION: /note= "Phe is the D-form of the
    amino acid."

( x i ) SEQUENCE DESCRIPTION: SEQ ID NO:213:

Tyr Tyr Phe
1

( 2 ) INFORMATION FOR SEQ ID NO:214:

( i ) SEQUENCE CHARACTERISTICS:
  ( A ) LENGTH: 4 amino acids
  ( B ) TYPE: amino acid
  ( D ) TOPOLOGY: linear ( i x ) FEATURE:
  ( A ) NAME/KEY: Peptide
  ( B ) LOCATION: 2
  ( D ) OTHER INFORMATION: /note= "Xaa is A1, where A1 is
   ( D )Nve or (D)Nle."

( i x ) FEATURE:
  ( A ) NAME/KEY: Peptide
  ( B ) LOCATION: 2
  ( D ) OTHER INFORMATION: /note= "Xaa is B2, where B2 is Gly,
   Phe or Trp."

( i x ) FEATURE:
  ( A ) NAME/KEY: Peptide
  ( B ) LOCATION: 3
  ( D ) OTHER INFORMATION: /note= "Xaa is C3, where C3 is Trp
   or Nap."

( i x ) FEATURE:
  ( A ) NAME/KEY: Peptide
  ( B ) LOCATION: 3
  ( D ) OTHER INFORMATION: /note= "Amino acid is amidated at
   the C- terminal."

( x i ) SEQUENCE DESCRIPTION: SEQ ID NO:214:

Tyr Xaa Xaa Xaa
1

( 2 ) INFORMATION FOR SEQ ID NO:215:

( i ) SEQUENCE CHARACTERISTICS:
  ( A ) LENGTH: 6 amino acids
  ( B ) TYPE: amino acid
  ( D ) TOPOLOGY: linear ( i x ) FEATURE:
  ( A ) NAME/KEY: Peptide
  ( B ) LOCATION: 1..5
  ( D ) OTHER INFORMATION: /note= "All amino acids are the
   D-form."

( i x ) FEATURE:
  ( A ) NAME/KEY: Peptide
  ( B ) LOCATION: 6
  ( D ) OTHER INFORMATION: /note= "Xaa is Gly or the D-form of
   a naturally- occurring amino acid."

( i x ) FEATURE:
  ( A ) NAME/KEY: Peptide
  ( B ) LOCATION: 6
  ( D ) OTHER INFORMATION: /note= "Amino acid is amidated at
   the C- terminal."

( x i ) SEQUENCE DESCRIPTION: SEQ ID NO:215:

Ile Met Ser Trp Trp Xaa
1      5

( 2 ) INFORMATION FOR SEQ ID NO:216:

( i ) SEQUENCE CHARACTERISTICS:
  ( A ) LENGTH: 7 amino acids
  ( B ) TYPE: amino acid ( D ) TOPOLOGY: linear ( i x ) FEATURE:
    ( A ) NAME/KEY: Peptide
    ( B ) LOCATION: 1..6
    ( D ) OTHER INFORMATION: /note= "Amino acids are the
        D-form."

( i x ) FEATURE:
    ( A ) NAME/KEY: Peptide
    ( B ) LOCATION: 7
    ( D ) OTHER INFORMATION: /note= "Xaa is Gly or the D-form of
        a naturally- occurring amino acid."

( i x ) FEATURE:
    ( A ) NAME/KEY: Peptide
    ( B ) LOCATION: 7
    ( D ) OTHER INFORMATION: /note= "Amino acid is amidated at
        the C- terminal."

( x i ) SEQUENCE DESCRIPTION: SEQ ID NO:216:

Ile Met Ser Trp Trp Gly Xaa
1                 5

( 2 ) INFORMATION FOR SEQ ID NO:217:

( i ) SEQUENCE CHARACTERISTICS:
        ( A ) LENGTH: 4 amino acids
        ( B ) TYPE: amino acid
        ( D ) TOPOLOGY: linear ( x i ) SEQUENCE DESCRIPTION: SEQ ID NO:217:

Tyr Tyr Phe Pro
1

( 2 ) INFORMATION FOR SEQ ID NO:218:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:218:

Tyr Gly Gly Phe Leu
1               5

( 2 ) INFORMATION FOR SEQ ID NO:219:

( i ) SEQUENCE CHARACTERISTICS:
        ( A ) LENGTH: 6 amino acids
        ( B ) TYPE: amino acid
        ( D ) TOPOLOGY: linear ( i x ) FEATURE:
        ( A ) NAME/KEY: Peptide
        ( B ) LOCATION: 1
        ( D ) OTHER INFORMATION: /note= "Amino acid is acetylated at
            the N- terminal."

( i x ) FEATURE:
        ( A ) NAME/KEY: Peptide
        ( B ) LOCATION: 6
        ( D ) OTHER INFORMATION: /note= "Amino acid is amidated at
            the C- terminal."

( x i ) SEQUENCE DESCRIPTION: SEQ ID NO:219:

Arg Phe Met Trp Met Lys
1                 5

( 2 ) INFORMATION FOR SEQ ID NO:220:

( i ) SEQUENCE CHARACTERISTICS:

(A) LENGTH: 6 amino acids
(B) TYPE: amino acid
(D) TOPOLOGY: linear (ix) FEATURE:
(A) NAME/KEY: Peptide
(B) LOCATION: 1..5
(D) OTHER INFORMATION: /note= "The amino acids in positions 1 through 5 are the D-form."

(ix) FEATURE:
(A) NAME/KEY: Peptide
(B) LOCATION: 6
(D) OTHER INFORMATION: /note= "Amino acid is amidated at the C- terminal."

(xi) SEQUENCE DESCRIPTION: SEQ ID NO:220:

Ile Met Ser Trp Trp Gly
1               5

(2) INFORMATION FOR SEQ ID NO:221:

(i) SEQUENCE CHARACTERISTICS:
(A) LENGTH: 3 amino acids
(B) TYPE: amino acid
(D) TOPOLOGY: linear (ix) FEATURE:
(A) NAME/KEY: Peptide
(B) LOCATION: 1
(D) OTHER INFORMATION: /note= "Tyr has at its N-terminal an Me-x-H-y- N group, wherein x is 0, 1, or 2; and y is 0, 1, or 2, with the proviso that x and y is never greater than 2."

(ix) FEATURE:
(A) NAME/KEY: Peptide
(B) LOCATION: 1..2
(D) OTHER INFORMATION: /note= "The amine between the first Tyr and the second Tyr is methylated."

(ix) FEATURE:
(A) NAME/KEY: Peptide
(B) LOCATION: 3
(D) OTHER INFORMATION: /note= "Xaa is Xaa-z wherein Xaa is Phe, (D)Phe or NHBzl, and wherein z is 0 or 1."

(ix) FEATURE:
(A) NAME/KEY: Peptide
(B) LOCATION: 3
(D) OTHER INFORMATION: /note= "Amino acid is amidated at the C- terminal."

(xi) SEQUENCE DESCRIPTION: SEQ ID NO:221:

Tyr Tyr Xaa
1

(2) INFORMATION FOR SEQ ID NO:222:

(i) SEQUENCE CHARACTERISTICS:
(A) LENGTH: 6 amino acids
(B) TYPE: amino acid
(D) TOPOLOGY: linear (ix) FEATURE:
(A) NAME/KEY: Peptide
(B) LOCATION: 4
(D) OTHER INFORMATION: /note= "Xaa is Lys or Arg."

(ix) FEATURE:
(A) NAME/KEY: Peptide
(B) LOCATION: 5
(D) OTHER INFORMATION: /note= "His is His-z, wherein z is 0 or 1."

(ix) FEATURE:

```
        ( A ) NAME/KEY: Peptide
        ( B ) LOCATION: 6
        ( D ) OTHER INFORMATION: /note= "Xaa is Xaa-z, wherein Xaa
              is a naturally-occurring amino acid and z is 0 or
              1."

( i x ) FEATURE:
        ( A ) NAME/KEY: Peptide
        ( B ) LOCATION: 6
        ( D ) OTHER INFORMATION: /note= "Amino acid is amidated at
              the C- terminal."

( x i ) SEQUENCE DESCRIPTION: SEQ ID NO:222:

Trp  Trp  Pro  Xaa  His  Xaa
  1                   5
```

μ OPIOID RECEPTOR LIGANDS: AGONISTS AND ANTAGONISTS

BACKGROUND OF THE INVENTION

1. Field of the Invention

The present invention relates generally to the field of peptide chemistry and, more specifically, to novel opioid peptides that can inhibit ligand binding to an opioid receptor.

2. Background Information

There are at least three known subtypes of opioid receptors, mu (μ), delta (δ), and kappa (κ), to which morphine, the enkephalins, and the dynorphins, respectively, bind. The three receptor subtypes possess analgesic properties. However, the type of pain inhibited and the secondary functions vary with each receptor type. The μ receptor is generally regarded as the one associated with pain relief, respiratory depression, intestinal motility, antidiuresis, an immune response, and drug or other physical dependence. The δ receptor, on the other hand, is associated with thermal analgesia and, to a lesser extent, respiration and addiction. The κ receptor, though associated with dysphoric and psychometric effects, also has a lower potential for dependence as compared to the μ receptor. The κ receptor is potent in affecting analgesia in response to pain, including chemical stimuli. The κ receptor also induces diuresis and sedation. These differences in the opioid receptor functions encourage the search for drugs which produce analgesia without deleterious side effects.

The use of synthetic peptides has been instrumental in the delineation of these subtypes and in providing analogues that can be used for studying the interactions of ligands specific to these receptor systems in both in vitro and in vivo systems. Certain opioid compounds are agonists (bind to the receptor and produce an effect) while others are antagonists (bind to the receptor but do not produce an effect). Most previously known agonists and antagonists of the opioid receptors are analogues of the enkephalins and related peptides, including the dynorphins, the dermenkephalins and the casomorphins. The compounds of the present invention have little to no sequence homology with any of these known opioid peptides.

Recent advances in methods for the preparation and screening of large numbers of individual peptides has led to the identification of numerous peptides useful in all areas of biomedical research, including research regarding the interaction of a ligand to the opiate receptor. Both receptor-specific agonists and antagonists are needed as pharmacological tools and as therapeutic agents. Even with these advances, however, basic research and drug discovery has been limited by the availability of the requisite large number of diverse opiate agonists and antagonists required to ascertain the relationship between a ligand for a particular opiate receptor subtype. Thus, a need exists for large numbers of individual compounds for use in biomedical research, including those for the study of opiate ligand-receptor interactions. As well there is a need for opioid peptides which have therapeutic value. This invention satisfies these needs and provides related advantages as well.

SUMMARY OF THE INVENTION

The present invention provides novel opioid peptides. These opioid peptides have the general structures Ac-Phe-Arg-Trp-Trp-Tyr-Xaa—NH$_2$ (SEQ ID NO. 1); Ac-Arg-Trp-Ile-Gly-Trp-Xaa—NH$_2$ (SEQ ID NO. 2); Trp-Trp-Pro-Lys-His-Xaa—NH$_2$ (SEQ ID NO. 3); Trp-Trp-Pro-Xaa—NH$_2$ (SEQ ID NO. 4); Tyr-Pro-Phe-Gly-Phe-Xaa—NH$_2$ (SEQ ID NO. 5); (D)Ile-(D)Met-(D)Ser-(D)Trp-(D)Trp-Gly$_n$-Xaa—NH$_2$ (SEQ ID NO. 6); and (D)Ile-(D)Met-(D)Thr-(D)Trp-Gly-Xaa—NH$_2$ (SEQ ID NO. 7). Within each above genus, Xaa is substituted by an amino acid. The invention also relates to an opioid peptide having the general structure Tyr-A1-B2-C3—NH$_2$ (SEQ ID NO. 214), wherein A1 is (D)Nve or (D)Nle, B2 is Gly, Phe, or Trp, and C3 is Trp or Nap. Also included within the invention are opioid compounds of the general structure Pm and red {Me$_x$H$_y$N-Tyr-(NMe)$_z$-Tyr-Xaa$_z$—NH$_2$} (SEQ ID NO. 221), wherein Xaa is substituted by a specific amino acid.

DETAILED DESCRIPTION OF THE INVENTION

Figure 1:
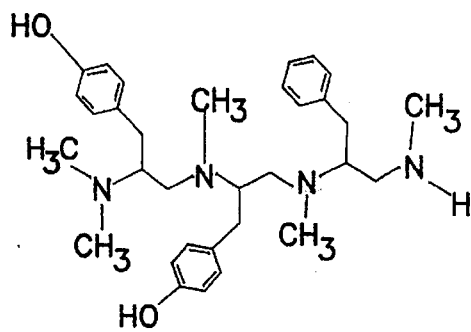
FIG. 1 shows the chemical structures for the compounds of SEQ ID NOS. 162 through 167. The chemical structures shown in FIG. 1 are two-dimensional.
Figure 1:
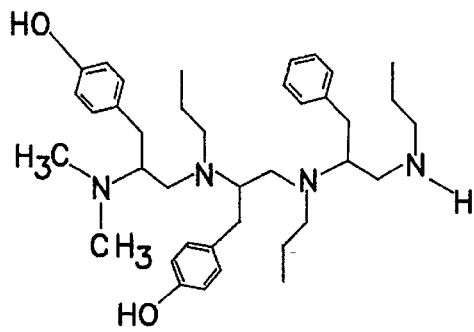
Figure 1:
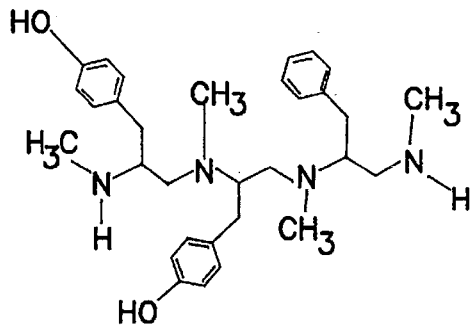
Figure 1:
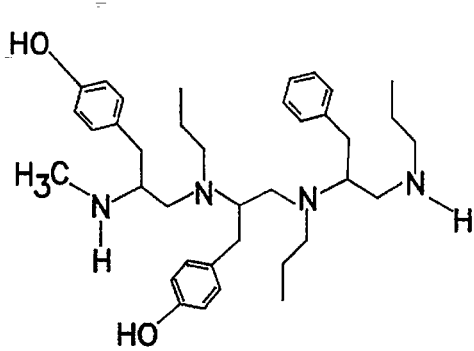
Figure 1:
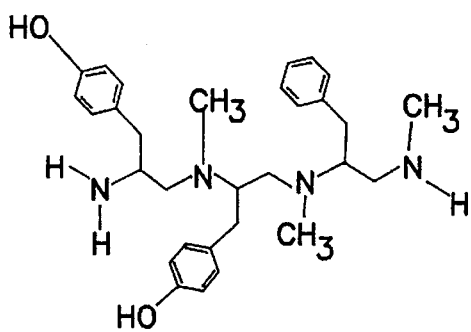
Figure 1:
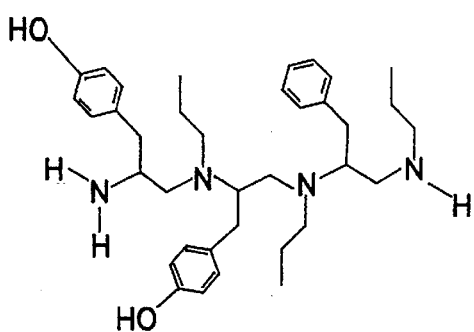

The present invention provides novel opioid peptides which are capable of inhibiting the binding of the μ-selective opioid peptide [$^3$H]-[D-Ala$^2$, MePhe$^4$, Gly-ol$^5$]enkephalin. In one embodiment, the peptides have the general structure Ac-Phe-Arg-Trp-Trp-Tyr-Xaa—NH$_2$ (SEQ ID NO. 1), wherein Xaa is any one of the twenty naturally occurring amino acids.

In another embodiment, the novel peptides are those encompassed by the formula Ac-Arg-Trp-Ile-Gly-Trp-Xaa—NH$_2$ (SEQ ID NO. 2), where Xaa can be any one of the twenty naturally occurring amino acids.

In yet other embodiments of the present invention, the peptides have the structure Trp-Trp-Pro-Lys-His-Xaa—NH$_2$ (SEQ ID NO. 3), where Xaa can be any one of the twenty naturally occurring amino acids, or Trp-Trp-Pro-Xaa—NH$_2$ (SEQ ID NO. 4), where Xaa is Lys or Arg.

Another embodiment of the invention provides peptides having the structure Tyr-Pro-Phe-Gly-Phe-Xaa—NH$_2$ (SEQ ID NO. 5), wherein Xaa can be any one of the twenty naturally occurring amino acids.

The invention also provides peptides falling within the structural formula (D)Ile-(D)Met-(D)Ser-(D)Trp-(D)Trp-Gly$_n$-Xaa—NH$_2$ (SEQ ID NO. 6), wherein Xaa is Gly or the D-form of a naturally-occurring amino acid and n is 0 or 1. Peptides of this formula can be hexapeptides when Gly is absent (n is 0) and heptapeptides when Gly is present (n is 1).

Another embodiment also comprising D-amino acids are those peptides within the formula (D)Ile-(D)Met-(D)Thr- (D)Trp-Gly-Xaa—NH$_2$ (SEQ ID NO. 7), wherein Xaa is Gly or the D-form of a naturally-occurring amino acid.

The invention also provides opioid peptides having the general structure Tyr-A1-B2-C3—NH$_2$ (SEQ ID NO. 214), wherein A1 is (D)Nve or (D)Nle, B2 is Gly, Phe, or Trp, and C3 is Trp or Nap.

Also included within the invention are opioid compounds of the general structure Pm and red {Me$_x$H$_y$N-Tyr-(NMe)$_z$-Tyr-Xaa$_z$—NH$_2$} (SEQ ID NO. 221), wherein x and y independently are 0, 1, or 2 and z is 0 or 1, and wherein Xaa is Phe D-Phe, or NHBzl.

The following standard abbreviations are used herein to identify amino acid residues.

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| NapthylAlaline | Nap | — |
| NorLeucine | Nle | — |
| NorValine | Nve | — |
| Phenylalanine | Phe | F |
| Proline | Pro | P |
| Serine | Ser | S |
| Threonine | Thr | T |
| Tetrahydroisoquinone-3-carboxylic acid | Tic | |
| Tryptophan | Trp | W |
| Tyrosine | Tyr | Y |
| Valine | Val | V |

The amino acids are indicated by these commonly known three and one letter codes as provided above and (D) designates an amino acid having the "D" configuration, as opposed to the naturally occurring L-amino acids. Where no specific configuration is indicated, one skilled in the art would understand the amino acid to be an (L)-amino acid. The alpha carbon atom of Gly is not asymmetric because it has two hydrogen atoms. Accordingly, Gly does not occur as a D or L isomer and is, therefore, not indicated to have either configuration.

As used herein, the phrase "any one of the twenty naturally occurring amino acids" means any one of the following: Ala, Arg, Asn, Asp, Cys, Gln, Glu, Gly, His, Ile, Leu, Lys, Met, Phe, Pro, Ser, Thr, Trp, Tyr, and Val. As used herein, the language "the D-form of a naturally-occurring amino acid" means the D-isomer of any one of these naturally-occurring amino acids, with the exception of Gly, which, as discussed above, does not occur as D or L isomers.

One skilled in the art would know that one or more amino acids within the exemplified peptides could be modified or substituted, as for example, by a conservative amino acid substitution of one or more of the specific amino acids shown in the exemplified peptides. A conservative amino acid substitution change can include, for example, the substitution of one acidic amino acid for another acidic amino acid, of one hydrophobic amino acid for another hydrophobic amino acid or other conservative substitutions known in the art, including the use of non-naturally occurring amino acids, such as Nle for Leu or ornithine (Orn) or homoArginine (homoArg) for Arg.

In addition to the above types of modifications or substitutions, a mimic of one or more amino acids, otherwise known as a peptide mimetic or peptidominetic, can also be used. As used herein, the term "mimic" means an amino acid or an amino acid analog that has the same or similar functional characteristic of an amino acid. Thus, for example, a (D)arginine analog can be a mimic of (D)arginine if the analog contains a side chain having a positive charge at physiological pH, as is characteristic of the guinidinium side chain reactive group of arginine. A peptide mimetic or peptidomimetic is an organic molecule that retains similar peptide chain pharmacophore groups as are present in the corresponding peptide.

The substitution of amino acids by non-naturally occurring amino acids and peptidomimetics as described above can enhance the overall activity or properties of an individual peptide based on the modifications to the side chain functionalities. For example, these types of alterations to the specifically exemplified peptides can enhance the peptide's stability to enzymatic breakdown and increase biological activity.

One skilled in the art, using the above formulae, can easily synthesize the peptides of this invention. Standard procedures for preparing synthetic peptides are well known in the art. The novel opioid peptides can be synthesized using the solid phase peptide synthesis (SPPS) method of Merrifield (*J. Am. Chem. Soc.*, 85:2149 (1964), which is incorporated herein by reference) or modifications of SPPS, or the peptides can be synthesized using standard solution methods well known in the art (see, for example, Bodanzsky, M., *Principles of Peptide Synthesis* 2nd revised ed. (Springer-Verlag, 1988 and 1993), which is incorporated herein by reference). Alternatively, simultaneous multiple peptide synthesis (SMPS) techniques well known in the art can be used. Peptides prepared by the method of Merrifield can be synthesized using an automated peptide synthesizer such as the Applied Biosystems 431A-01 Peptide Synthesizer (Mountain View, Calif.) or using the manual peptide synthesis technique described by Houghten, *Proc. Natl. Acad. Sci., USA* 82:5131 (1985), which is incorporated herein by reference.

Peptides can be synthesized using amino acids or amino acid analogs, the active groups of which are protected as necessary using, for example, a t-butyldicarbonate (t-BOC) group or a fluorenylmethoxy carbonyl (FMOC) group. Amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)phenoxymethyl-copoly(styrene-1% divinylbenzene) (Wang resin), all of which are commercially available, or to p-nitrobenzophenone oxime polymer (oxime resin), which can be synthesized as described by De Grado and Kaiser, *J. Org. Chem.* 47:3258 (1982), which is incorporated herein by reference.

In the exemplified peptides, "Ac" indicates an acetyl group at the amino terminus and "NH$_2$" an amide group on the carboxy terminus. Peptides can be manipulated, for example, while still attached to a resin to obtain N-terminal modified compounds such as an acetylated peptide or can be removed from the resin using hydrogen fluoride or an equivalent cleaving reagent and then modified. Compounds synthesized containing the C-terminal carboxy group (Wang resin) can be modified after cleavage from the resin or, in some cases, prior to solution phase synthesis. Methods for modifying the N-terminus or C-terminus such as methods for acetylation of the N-terminus or methods for amidation of the C-terminus are well known in the art.

Figure 2:
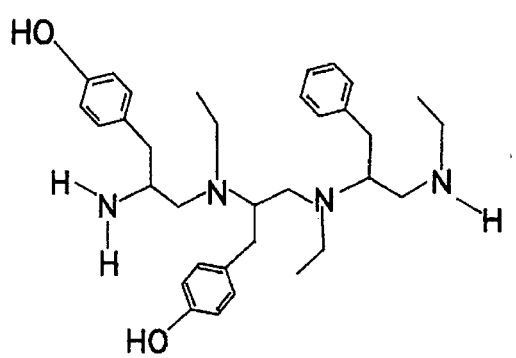
FIG. 2 provides the two-dimensional chemical structures for the compounds identified by SEQ ID NOS. 168 to 173.
Figure 2:
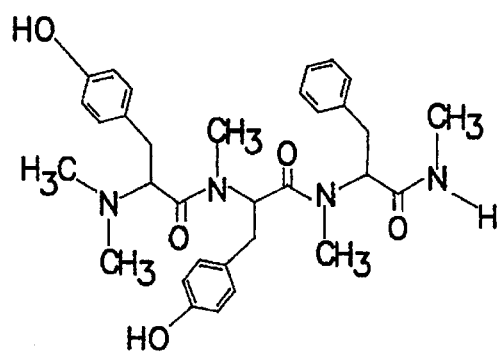
Figure 2:
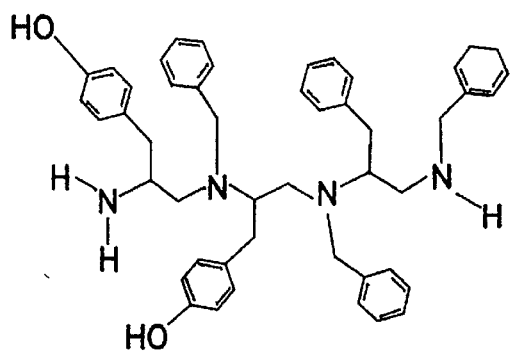
Figure 2:
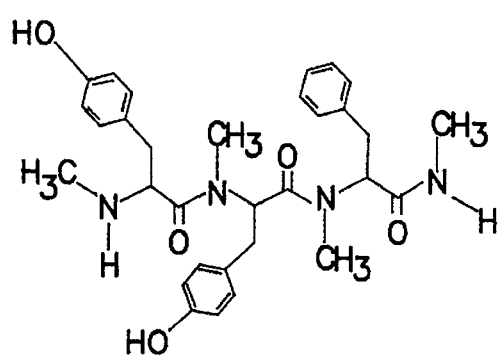
Figure 2:
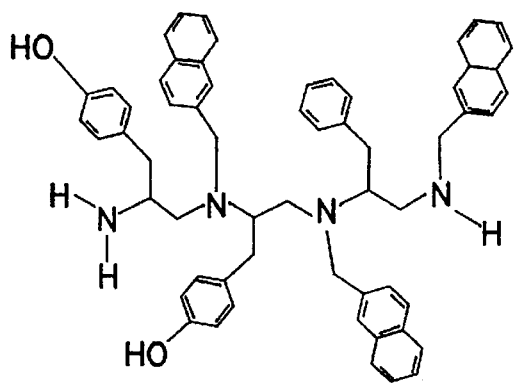
Figure 2:
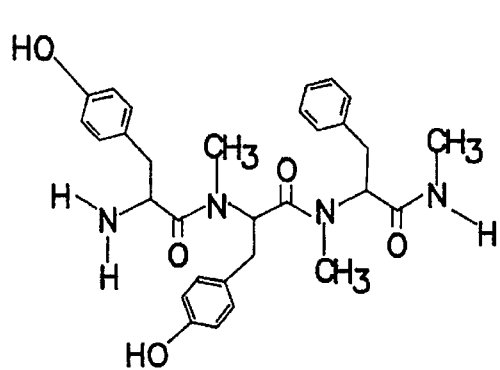
Figure 3:
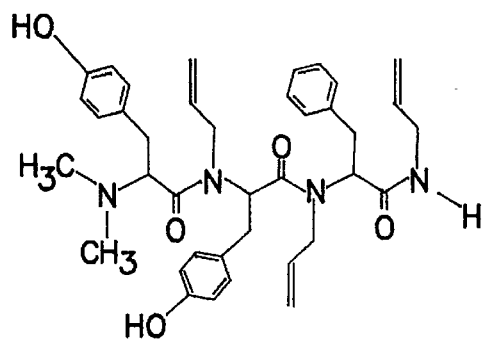
FIG. 3 depicts the two-dimensional chemical structures for the compounds corresponding to SEQ ID NOS. 174 through 179.
Figure 3:
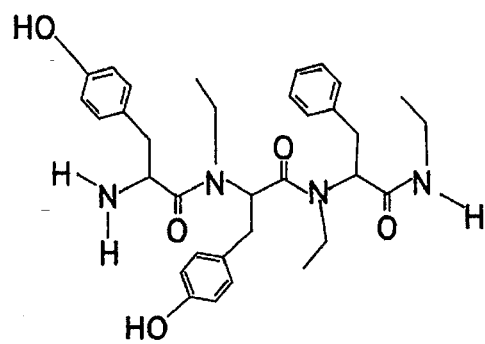
Figure 3:
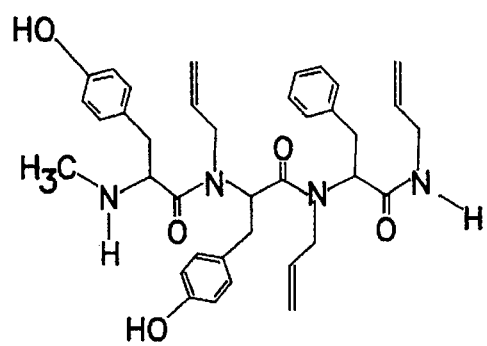
Figure 3:
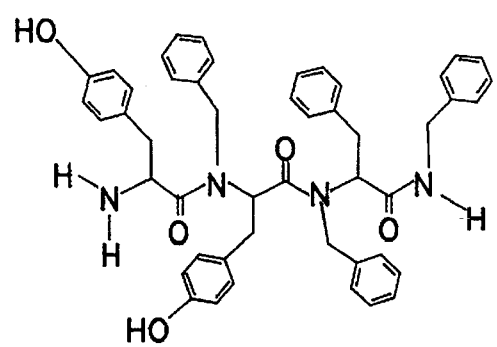
Figure 3:
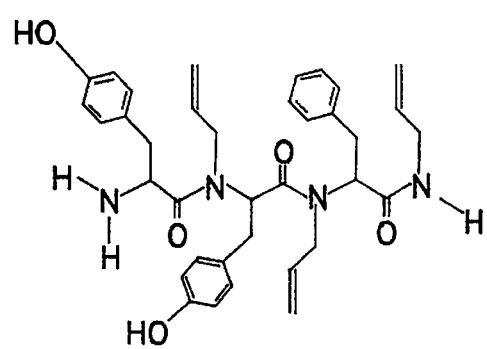
Figure 3:
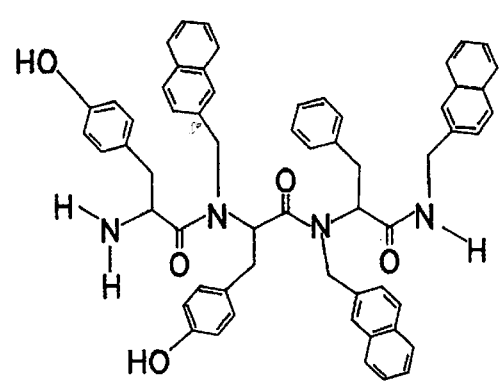
Figure 4:
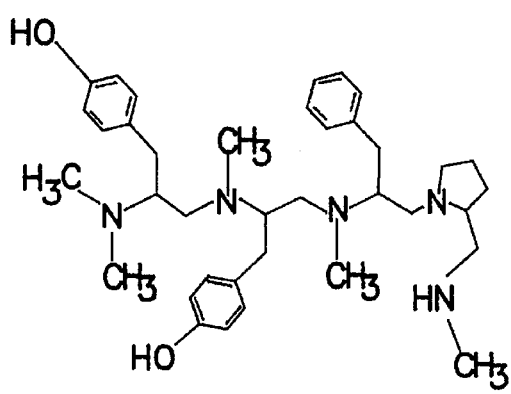
FIG. 4 shows the two-dimensional chemical structures for the compounds of SEQ ID. NOS. 180 to 185.
Figure 4:
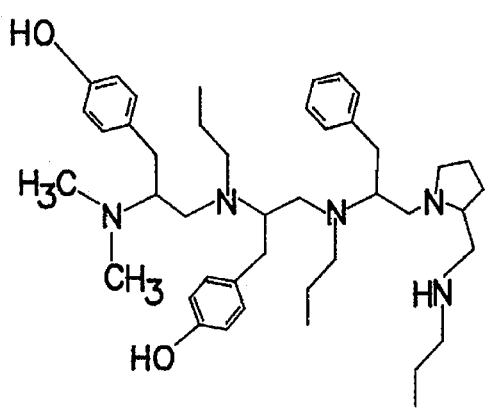
Figure 4:
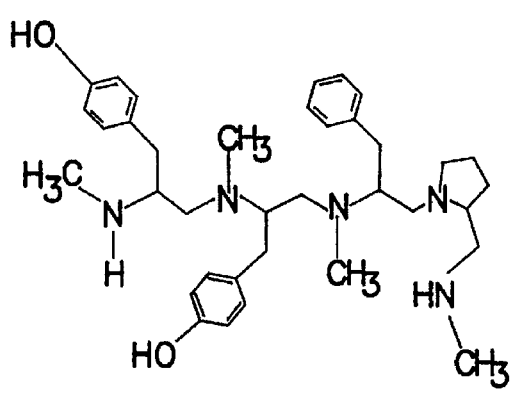
Figure 4:
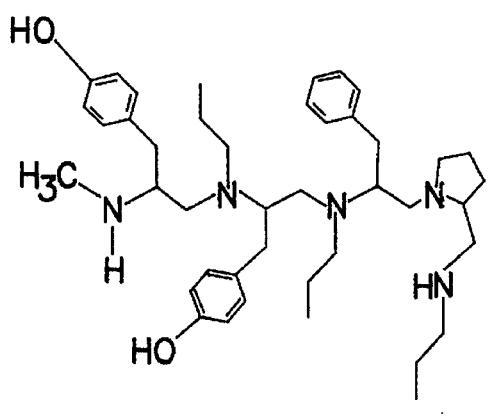
Figure 4:
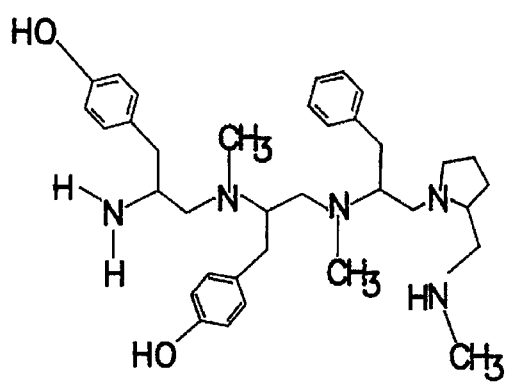
Figure 4:
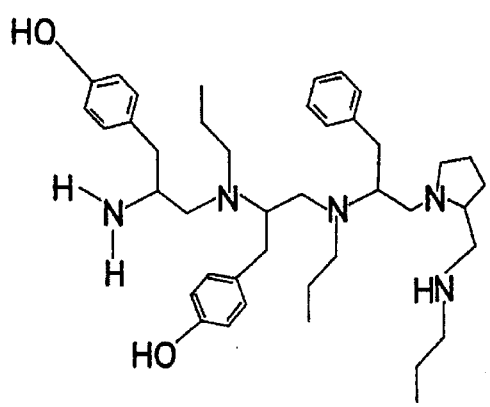
Figure 5:
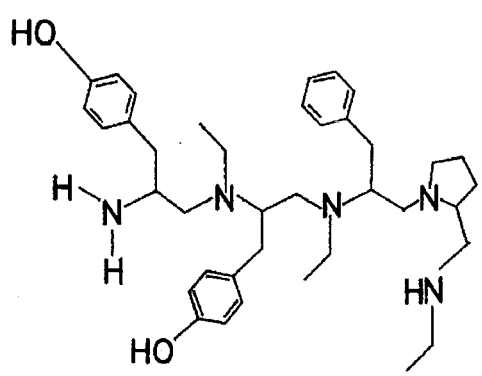
FIG. 5 provides the two-dimensional chemical structures for the compounds corresponding to SEQ ID NOS. 186 through 191.
Figure 5:
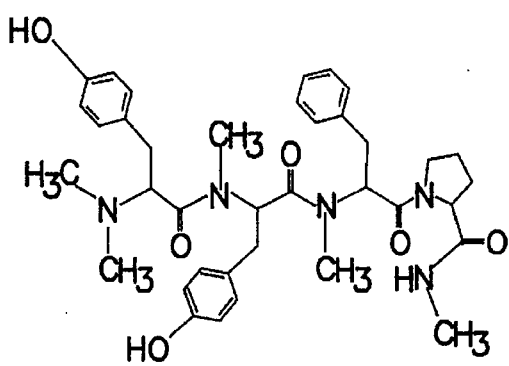
Figure 5:
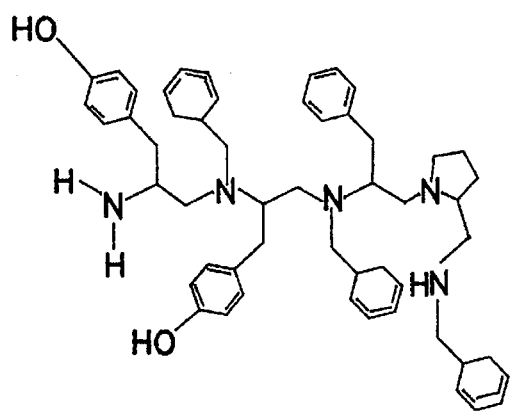
Figure 5:
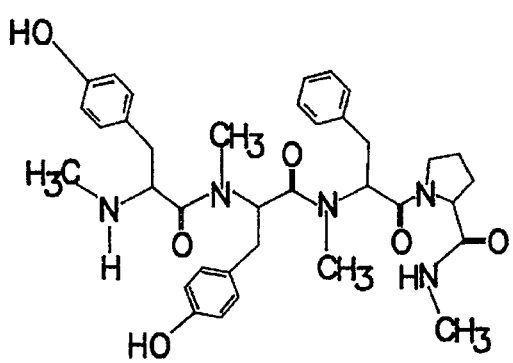
Figure 5:
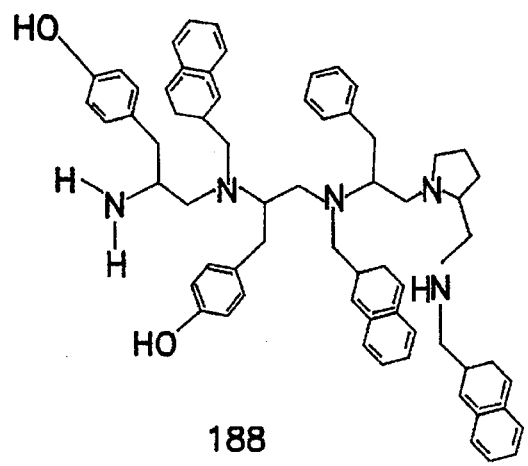
Figure 5:
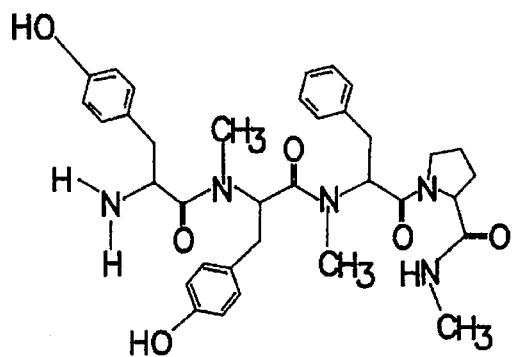
Figure 6:
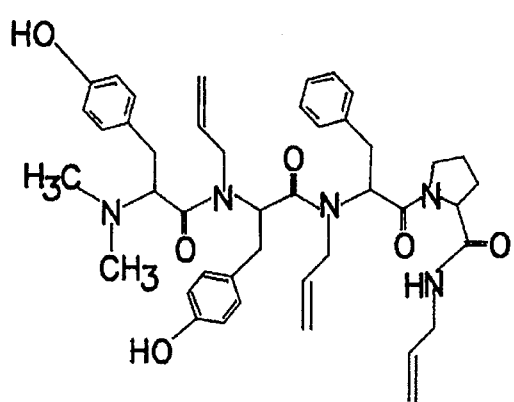
FIG. 6 shows the two-dimensional chemical structures of the compounds corresponding to SEQ ID NOS. 192 through 197.
Figure 6:
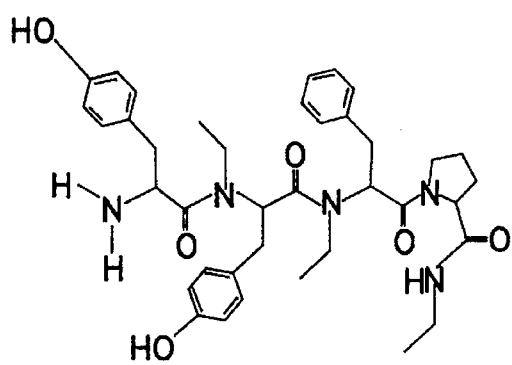
Figure 6:
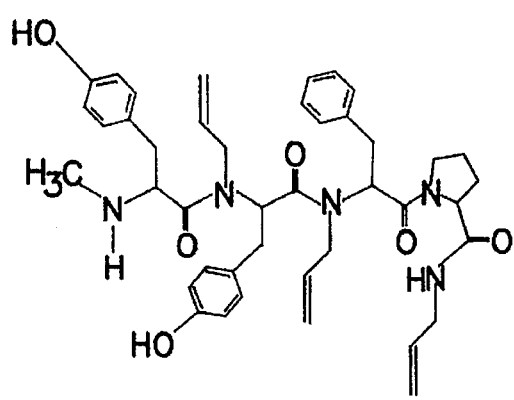
Figure 6:
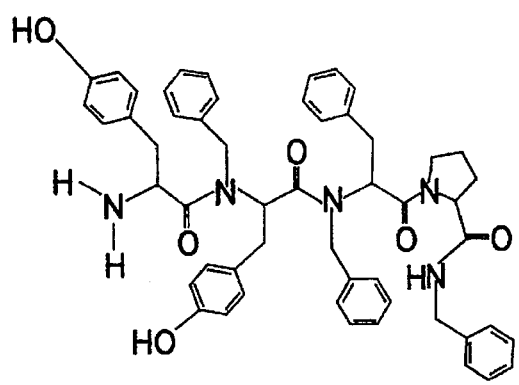
Figure 6:
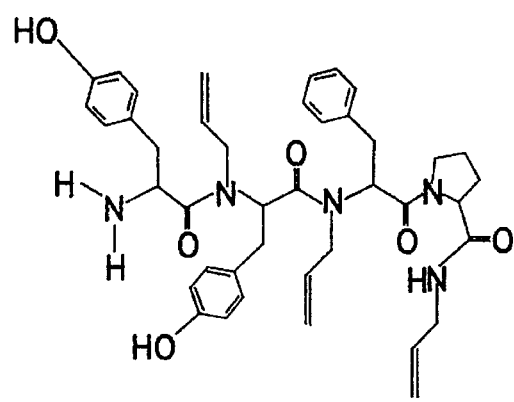
Figure 6:
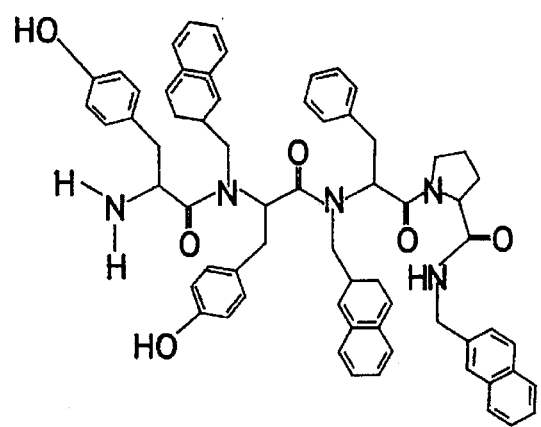
Figure 7:
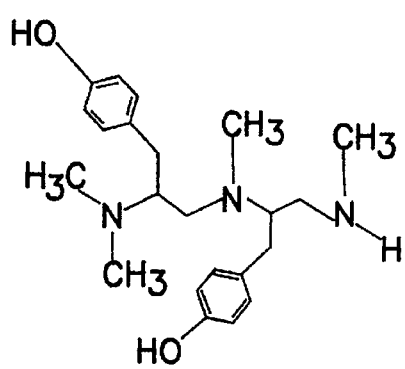
FIG. 7 depicts the two-dimensional chemical structures for the compounds of SEQ ID NOS. 198 through 203.
Figure 7:
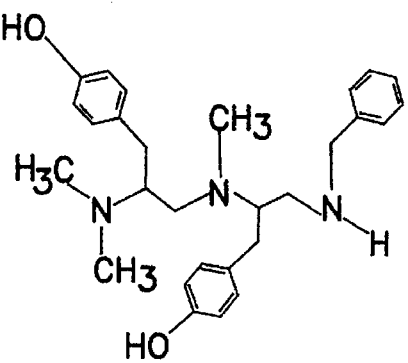
Figure 7:
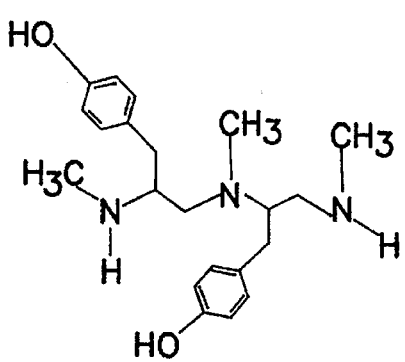
Figure 7:
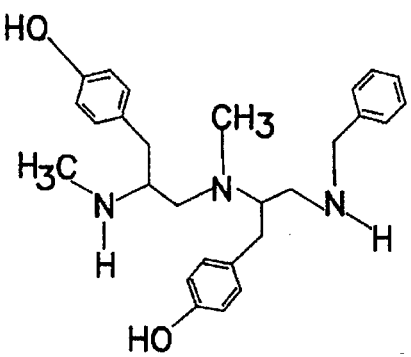
Figure 7:
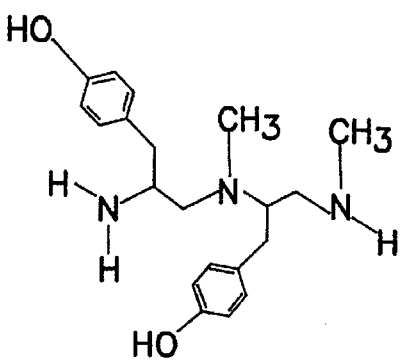
Figure 7:
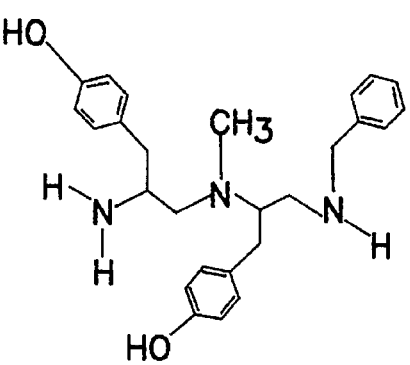

Additional nomenclature used in the exemplified peptides includes, and means, the following: "Pm", permethylated; "Pa", perallylated; "Pe", perethylated; "Pb", perbenzylated; "Pn", pernaphthylated. The methylation, allylation, ethylation, benzylation, and naphthylation in the respective peptides is at each of the nitrogen atoms in the peptide backbone as shown in FIGS. 1 through 7. Modification of the amide backbone by permethylation and the like yields peptidomimetics with diverse physio-chemical properties different from the peptides from which they were obtained, such as enhanced stability to enzymatic breakdown and increased biological activity. Various methods for permethylation and the like have been described, including Ostresh et al., *Proc. Natl. Acad. Sci. USA,* 91:11138 (1994), Hakomori, S., *J. Biochem.,* 55:205 (1964), Challis and Challis, *The Chemistry of Amides,* pp.731 (1970), all of which are incorporated herein by reference.

The reduction of the peptide amides is another means for the chemical transformation of peptides which adds stability and can enhance activity. In the exemplified peptides, the use of "red" means that the carbonyls of the amide peptide backbone are reduced to amines, as shown, for instance in FIGS. 1 through 7 and more specifically, for example, in FIG. 1, number 162. A number of reagents are available and well known for the reduction of amides to amines such as those disclosed in Wann et al., *JOC,* 46:257 (1981) and Raucher et al., *Tett. Let.,* 21:14061 (1980), both of which are incorporated herein by reference. Diborane has the advantage that trimethylborate, the only by-product in the reaction workup, is volatile and is therefore readily removed by evaporation. The use of excess diborane in refluxing tetrahydrofuran permits simple aliphatic and aromatic amides to be rapidly, and often quantitatively be reduced into their corresponding amines.

A newly synthesized peptide can be purified using a method such as reverse phase high performance liquid chromatography (RP-HPLC) or other methods of separation based on the size or charge of the peptide. Furthermore, the purified peptide can be characterized using these and other well known methods such as amino acid analysis and mass spectrometry.

After manufacture, the peptides can be assayed for receptor binding activity using the radioreceptor assay (Examples I and II) or other assays outlined below, including the adenylyl cyclase assay (Example III), or the guinea-pig ileum assay (Example IV) or the mouse vas deferens assay (Example IV). In addition, the warm water mouse tail-flick assay is an in vivo animal model useful for testing peptides of the present invention. The tail-flick assay is described, for example, in Dooley et al., *Science,* 266:2019–2022 (1994) and Jiang et al., *J. Pharmacol. Exp. Ther.,* 262:526 (1992), both of which are incorporated herein by reference.

Because the peptides of the present invention bind to the μ receptor, they can be used in in vitro assays to study the opiate receptor subtypes. For example, in a sample receptor of unknown type or origin, the peptides, after being labeled with a detectable marker such as a radioisotope, can be contacted with the receptor sample under conditions which specifically favor binding to a particular receptor subtype. Unbound receptor and peptide can be removed, for example, by washing with a saline solution, and bound receptor can then be detected using methods well known to those skilled in the art. Therefore, the peptides of the present invention are useful in vitro for the diagnosis of relevant opioid receptor subtypes, and in particular the μ type, in brain and other tissue samples.

In addition to their utility in in vitro screening methods, the peptides are also useful in vivo. For example, the opioid peptides can be used in vivo diagnostically to localize opioid receptor subtypes. The peptides are also useful as drugs to treat pathologies associated with other compounds which interact with the opioid receptor system. It can be envisioned that these peptides can be used for therapeutic purposes to block the peripheral effects of a centrally acting pain killer. For instance, morphine is a centrally acting pain killer. Morphine, however, has a number of deleterious effects in the periphery which are not required for the desired analgesic effects, such as constipation and pruritus (itching). While it is known that the many peptides do not readily cross the blood-brain barrier and, therefore, elicit no central effect, the subject peptides can have value in blocking the periphery effects of morphine, such as constipation and pruritus.

The novel peptides claimed can be incorporated into pharmaceutical compositions. Pharmaceutically acceptable carriers are well known in the art and include aqueous solutions such as physiologically buffered saline or other buffers or solvents or vehicles such as glycols, glycerol, oils such as olive oil or injectable organic esters. A pharmaceutically acceptable carrier can contain physiologically acceptable compounds that act, for example, to stabilize the opioid peptide or increase the absorption of the peptide. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration and on the particular physio-chemical characteristics of the specific opioid peptide.

Methods of administering a pharmaceutical are well known in the art and include but are not limited to administration orally, intravenously, intramuscularly or intraperitoneal. Administration can be effected continuously or intermittently and will vary with the subject and is dependent on the type of treatment and potency of the peptide used.

The following examples are intended to illustrate but not limit the present invention.

EXAMPLE I

Identification Of Mu Selective Opioid Peptides By A Radioreceptor Assay

This example describes the identification of individual peptides, either contained within a synthetic combinatorial library mixture or prepared separately, as inhibitors of the μ-selective opioid peptide [$^3$H]-[D-Ala$^2$, MePhe$^4$, Gly-Ol$^5$ enkephalin ([$^3$H]-DAMGO). Individual peptides were identified as capable of inhibiting [$^3$H]-DAMGO by a radioreceptor assay.

Synthetic combinatorial libraries (SCLs) made up of mixtures of tens of millions of different peptides can be used to rapidly identify individual, active compounds. Since the libraries are in solution (i.e., not attached to a bead, pin, phage, glass, etc.) they can be screened in virtually any assay system.

With the exception of the permethylated and reduced peptides, all opioid peptides were initially prepared and contained within SCLs. Some SCLs were composed entirely of L-amino acids, one of which contained an N-terminal acetyl moiety, while other SCLs were composed primarily of D-amino acids as detailed by the peptide structures provided below. The libraries were used in conjunction with an iterative selection process to identify individual peptides capable of inhibiting tritiated DAMGO in the radioreceptor assay.

As detailed below, the libraries were screened at a single concentration (0.08 mg/ml) in a radioreceptor assay using rat brain homogenates and [$^3$H]-DAMGO as radioligand. IC$_{50}$ values were determined for mixtures in the library which significantly inhibited the binding of [$^3$H]-DAMGO.

Radioreceptor Assays Selective For The Mu Receptor

Rat and guinea pig brains, frozen in liquid nitrogen, were obtained from Harlan Bioproducts for Science (Indianapolis, Ind.). Frozen brains were thawed, the cerebella removed and the remaining tissue weighed. Each brain was individually homogenized in 40 ml Tris—HCl buffer (50 mM, pH 7.4, 4° C.) and centrifuged (39000×g) (Model J2-HC; Beckman Instruments, Fullerton, Calif.) for 10 min at 4° C. The pellets were resuspended in fresh Tris—HCl buffer and incubated at 37° C. for 40 min. Following incubation, the suspensions were centrifuged as above, the resulting pellets resuspended in 100 volumes of Tris buffer and the suspensions combined. Membrane suspensions were prepared and used in the same day. Protein content of the crude homogenates ranged from 0.15–0.2 mg/ml as determined using the method described by Bradford (Bradford, *Anal. Biochem.* 72:248–254 (1976), which is incorporated herein by reference).

Binding assays were carried out in polypropylene tubes. Each tube contained 0.5 ml of membrane suspension, 3 nM of the μ-selective opioid peptide [$^3$H]-DAMGO (specific activity 36 Ci/mmol), 0.08 mg/ml peptide mixture and Tris—HCl buffer in a total volume of 0.65 ml. Assay tubes were incubated for 60 min at 25° C. The reaction was terminated by filtration through GF-B filters (Wallac, Inc., Gaithersburg, Md.). The filters were subsequently washed with 6 ml Tris—HCl buffer at 4° C. Bound radioactivity was counted on a Beta-plate Liquid Scintillation Counter (Life Technologies, Gaithersburg, Md.) and expressed in counts per minute (cpm). Inter- and intra-assay variation standard curves were determined by incubation of [$^3$H]-DAMGO in the presence of 0.13–3900 nM of unlabeled DAMGO. Competitive inhibition assays were performed as above using serial dilutions of the peptide mixtures. IC$_{50}$ values were then calculated using the software GRAPHPAD (ISI, San Diego, Calif.). IC$_{50}$ values of less than 1000 nM are indicative of highly active opioid peptides which bind to the μ receptor, with particularly active compounds having IC$_{50}$ values of 100 nM or less and the most active compounds with values of less than 10 nM.

Opioid peptides having the general structure Ac-Phe-Arg-Trp-Trp-Tyr-Xaa—NH$_2$ (SEQ ID NO. 1), wherein Xaa is any one of the twenty naturally-occurring amino acids were identified. IC$_{50}$ values of these peptides are provided in Table 1.

TABLE 1

Ac—Phe—Arg—Trp—Trp—Tyr—Xaa—NH$_2$
(SEQ ID NO. 1)

| SEQ ID NO. | PEPTIDE | IC$_{50}$ (nM) |
|---|---|---|
| 8  | Ac—Phe—Arg—Trp—Trp—Tyr—Met—NH$_2$ | 33 |
| 9  | Ac—Phe—Arg—Trp—Trp—Tyr—Leu—NH$_2$ | 35 |
| 10 | Ac—Phe—Arg—Trp—Trp—Tyr—Ser—NH$_2$ | 39 |
| 11 | Ac—Phe—Arg—Trp—Trp—Tyr—Ala—NH$_2$ | 50 |
| 12 | Ac—Phe—Arg—Trp—Trp—Tyr—Ile—NH$_2$ | 64 |
| 13 | Ac—Phe—Arg—Trp—Trp—Tyr—Thr—NH$_2$ | 73 |
| 14 | Ac—Phe—Arg—Trp—Trp—Tyr—Val—NH$_2$ | 77 |
| 15 | Ac—Phe—Arg—Trp—Trp—Tyr—Gly—NH$_2$ | 78 |
| 16 | Ac—Phe—Arg—Trp—Trp—Tyr—Phe—NH$_2$ | 170 |
| 17 | Ac—Phe—Arg—Trp—Trp—Tyr—Arg—NH$_2$ | 191 |
| 18 | Ac—Phe—Arg—Trp—Trp—Tyr—Lys—NH$_2$ | 221 |
| 19 | Ac—Phe—Arg—Trp—Trp—Tyr—Gln—NH$_2$ | 234 |
| 20 | Ac—Phe—Arg—Trp—Trp—Tyr—Tyr—NH$_2$ | 257 |
| 21 | Ac—Phe—Arg—Trp—Trp—Tyr—His—NH$_2$ | 272 |
| 22 | Ac—Phe—Arg—Trp—Trp—Tyr—Trp—NH$_2$ | 326 |
| 23 | Ac—Phe—Arg—Trp—Trp—Tyr—Cys—NH$_2$ | 400 |
| 24 | Ac—Phe—Arg—Trp—Trp—Tyr—Asn—NH$_2$ | 486 |
| 25 | Ac—Phe—Arg—Trp—Trp—Tyr—Pro—NH$_2$ | 668 |
| 26 | Ac—Phe—Arg—Trp—Trp—Tyr—Asp—NH$_2$ | 769 |
| 27 | Ac—Phe—Arg—Trp—Trp—Tyr—Glu—NH$_2$ | 1480 |

Also identified from screening of the acetylated SCL were peptides of the general formula Ac-Arg-Trp-Ile-Gly-Trp-Xaa—NH$_2$ (SEQ ID NO. 2), wherein Xaa is any one of the twenty naturally-occurring amino acids. Table 2 provides the respective IC$_{50}$ values for each of the twenty peptides within this formula.

TABLE 2

Ac—Arg—Trp—Ile—Gly—Trp—Xaa—NH$_2$
(SEQ ID NO. 2)

| SEQ ID NO. | PEPTIDE | IC$_{50}$ (nM) |
|---|---|---|
| 28 | Ac—Arg—Trp—Ile—Gly—Trp—Arg—NH$_2$ | 5 |
| 29 | Ac—Arg—Trp—Ile—Gly—Trp—Lys—NH$_2$ | 35 |
| 30 | Ac—Arg—Trp—Ile—Gly—Trp—Thr—NH$_2$ | 51 |
| 31 | Ac—Arg—Trp—Ile—Gly—Trp—Met—NH$_2$ | 175 |
| 32 | Ac—Arg—Trp—Ile—Gly—Trp—Ile—NH$_2$ | 224 |
| 33 | Ac—Arg—Trp—Ile—Gly—Trp—Ala—NH$_2$ | 444 |
| 34 | Ac—Arg—Trp—Ile—Gly—Trp—Phe—NH$_2$ | 539 |
| 35 | Ac—Arg—Trp—Ile—Gly—Trp—Ser—NH$_2$ | 574 |
| 36 | Ac—Arg—Trp—Ile—Gly—Trp—Leu—NH$_2$ | 620 |
| 37 | Ac—Arg—Trp—Ile—Gly—Trp—Cys—NH$_2$ | 651 |
| 38 | Ac—Arg—Trp—Ile—Gly—Trp—Trp—NH$_2$ | 703 |
| 39 | Ac—Arg—Trp—Ile—Gly—Trp—Tyr—NH$_2$ | 976 |
| 40 | Ac—Arg—Trp—Ile—Gly—Trp—Val—NH$_2$ | 1070 |
| 41 | Ac—Arg—Trp—Ile—Gly—Trp—Gln—NH$_2$ | 1390 |
| 42 | Ac—Arg—Trp—Ile—Gly—Trp—His—NH$_2$ | 2010 |
| 43 | Ac—Arg—Trp—Ile—Gly—Trp—Gly—NH$_2$ | 2050 |
| 44 | Ac—Arg—Trp—Ile—Gly—Trp—Pro—NH$_2$ | 3090 |
| 45 | Ac—Arg—Trp—Ile—Gly—Trp—Asn—NH$_2$ | 3120 |
| 46 | Ac—Arg—Trp—Ile—Gly—Trp—Glu—NH$_2$ | 6150 |
| 47 | Ac—Arg—Trp—Ile—Gly—Trp—Asp—NH$_2$ | 6480 |

Screening of a non-acetylated, all L-amino acid library revealed that peptides of the formula Trp-Trp-Pro-Lys-His-Xaa—NH$_2$ (SEQ ID NO. 3) inhibited the μ-selective radioligand. Again, Xaa can be any one of twenty naturally-occurring amino acids as shown in Table 3, along with their respective IC$_{50}$ values. In addition two shorter analogues, Trp-Trp-Pro-Lys—NH$_2$ (SEQ ID NO. 68) and Trp-Trp-Pro-Arg—NH$_2$ (SEQ ID NO. 69) were identified, the IC$_{50}$ values of which are also provided in Table 3.

TABLE 3

Trp—Trp—Pro—Lys—His—Xaa—NH$_2$ (SEQ ID NO. 3)
and
Trp—Trp—Pro—Xaa—NH$_2$ (SEQ ID NO. 4)

| SEQ ID NO. | PEPTIDE | IC$_{50}$ (nM) |
|---|---|---|
| 48 | Trp—Trp—Pro—Lys—His—Gly—NH$_2$ | 9 |
| 49 | Trp—Trp—Pro—Lys—His—Asn—NH$_2$ | 11 |
| 50 | Trp—Trp—Pro—Lys—His—Lys—NH$_2$ | 13 |
| 51 | Trp—Trp—Pro—Lys—His—His—NH$_2$ | 14 |
| 52 | Trp—Trp—Pro—Lys—His—Ser—NH$_2$ | 15 |
| 53 | Trp—Trp—Pro—Lys—His—Arg—NH$_2$ | 17 |
| 54 | Trp—Trp—Pro—Lys—His—Ala—NH$_2$ | 17 |
| 55 | Trp—Trp—Pro—Lys—His—Gln—NH$_2$ | 18 |
| 56 | Trp—Trp—Pro—Lys—His—Ile—NH$_2$ | 31 |
| 57 | Trp—Trp—Pro—Lys—His—Pro—NH$_2$ | 32 |
| 58 | Trp—Trp—Pro—Lys—His—Thr—NH$_2$ | 33 |
| 59 | Trp—Trp—Pro—Lys—His—Cys—NH$_2$ | 33 |
| 60 | Trp—Trp—Pro—Lys—His—Val—NH$_2$ | 34 |
| 61 | Trp—Trp—Pro—Lys—His—Met—NH$_2$ | 42 |
| 62 | Trp—Trp—Pro—Lys—His—Phe—NH$_2$ | 50 |
| 63 | Trp—Trp—Pro—Lys—His—Glu—NH$_2$ | 55 |
| 64 | Trp—Trp—Pro—Lys—His—Tyr—NH$_2$ | 55 |
| 65 | Trp—Trp—Pro—Lys—His—Leu—NH$_2$ | 79 |
| 66 | Trp—Trp—Pro—Lys—His—Asp—NH$_2$ | 81 |
| 67 | Trp—Trp—Pro—Lys—His—Trp—NH$_2$ | 187 |
| 68 | Trp—Trp—Pro—Lys—NH$_2$ | 17 |
| 69 | Trp—Trp—Pro—Arg—NH$_2$ | 10 |

Also identified from a non-acetylated, L-amino acid SCL were peptides of the formula Tyr-Pro-Phe-Gly-Phe-Xaa—NH$_2$ (SEQ ID NO. 5). The IC$_{50}$ values for each of the peptides of this formula are provided in Table 4.

TABLE 4

Tyr—Pro—Phe—Gly—Phe—Xaa—NH$_2$
(SEQ ID NO. 5)

| SEQ ID NO. | PEPTIDE | IC$_{50}$ (nM) |
|---|---|---|
| 70 | Tyr—Pro—Phe—Gly—Phe—Arg—NH$_2$ | 13 |
| 71 | Tyr—Pro—Phe—Gly—Phe—Gly—NH$_2$ | 18 |
| 72 | Tyr—Pro—Phe—Gly—Phe—Lys—NH$_2$ | 19 |
| 73 | Tyr—Pro—Phe—Gly—Phe—Ser—NH$_2$ | 24 |
| 74 | Tyr—Pro—Phe—Gly—Phe—Ala—NH$_2$ | 27 |
| 75 | Tyr—Pro—Phe—Gly—Phe—Asn—NH$_2$ | 28 |
| 76 | Tyr—Pro—Phe—Gly—Phe—Pro—NH$_2$ | 31 |
| 77 | Tyr—Pro—Phe—Gly—Phe—Gln—NH$_2$ | 33 |
| 78 | Tyr—Pro—Phe—Gly—Phe—Met—NH$_2$ | 33 |
| 79 | Tyr—Pro—Phe—Gly—Phe—His—NH$_2$ | 38 |
| 80 | Tyr—Pro—Phe—Gly—Phe—Tyr—NH$_2$ | 41 |
| 81 | Tyr—Pro—Phe—Gly—Phe—Ile—NH$_2$ | 43 |
| 82 | Tyr—Pro—Phe—Gly—Phe—Thr—NH$_2$ | 45 |
| 83 | Tyr—Pro—Phe—Gly—Phe—Leu—NH$_2$ | 48 |
| 84 | Tyr—Pro—Phe—Gly—Phe—Val—NH$_2$ | 50 |
| 85 | Tyr—Pro—Phe—Gly—Phe—Phe—NH$_2$ | 61 |
| 86 | Tyr—Pro—Phe—Gly—Phe—Asp—NH$_2$ | 75 |
| 87 | Tyr—Pro—Phe—Gly—Phe—Cys—NH$_2$ | 81 |
| 88 | Tyr—Pro—Phe—Gly—Phe—Trp—NH$_2$ | 87 |
| 89 | Tyr—Pro—Phe—Gly—Phe—Glu—NH$_2$ | 119 |

Peptides of the general formula (D)Ile-(D)Met-(D)Ser-(D)Trp-(D)Trp-Gly$_n$-Xaa—NH$_2$ (SEQ ID NO. 6) were also inhibitors of [$^3$H]-DAMGO binding. IC$_{50}$ for the hexapeptides (n=0) of the formula (D)Ile-(D)Met-(D)Ser-(D)Trp-(D)Trp-Xaa—NH$_2$ (SEQ ID NO. 215), and for the heptapeptides (n=1) of the formula (D)Ile-(D)Met-(D)Ser-(D)Trp-(D)Trp-Gly-Xaa-NH$_2$ (SEQ ID NO. 216), wherein Xaa is Gly or the D-form of a naturally-occurring amino acid, are provided in Tables 5 and 6, respectively.

TABLE 5

(D)Ile—(D)Met—(D)Ser—(D)Trp—(D)Trp—Xaa—NH$_2$
(SEQ ID NO. 2/5)

| SEQ ID NO. | PEPTIDE | IC$_{50}$ (nM) |
|---|---|---|
| 90 | (D)Ile—(D)Met—(D)Ser—(D)Trp—(D)Trp—Gly—NH$_2$ | 10 |
| 91 | (D)Ile—(D)Met—(D)Ser—(D)Trp—(D)Trp—(D)Ala—NH$_2$ | 12 |
| 92 | (D)Ile—(D)Met—(D)Ser—(D)Trp—(D)Trp—(D)His—NH$_2$ | 16 |
| 93 | (D)Ile—(D)Met—(D)Ser—(D)Trp—(D)Trp—(D)Val—NH$_2$ | 17 |
| 94 | (D)Ile—(D)Met—(D)Ser—(D)Trp—(D)Trp—(D)Tyr—NH$_2$ | 18 |
| 95 | (D)Ile—(D)Met—(D)Ser—(D)Trp—(D)Trp—(D)Ser—NH$_2$ | 20 |
| 96 | (D)Ile—(D)Met—(D)Ser—(D)Trp—(D)Trp—(D)Ile—NH$_2$ | 20 |
| 97 | (D)Ile—(D)Met—(D)Ser—(D)Trp—(D)Trp—(D)Arg—NH$_2$ | 22 |
| 98 | (D)Ile—(D)Met—(D)Ser—(D)Trp—(D)Trp—(D)Met—NH$_2$ | 26 |
| 99 | (D)Ile—(D)Met—(D)Ser—(D)Trp—(D)Trp—(D)Asn—NH$_2$ | 29 |
| 100 | (D)Ile—(D)Met—(D)Ser—(D)Trp—(D)Trp—(D)Gln—NH$_2$ | 30 |
| 101 | (D)Ile—(D)Met—(D)Ser—(D)Trp—(D)Trp—(D)Pro—NH$_2$ | 32 |
| 102 | (D)Ile—(D)Met—(D)Ser—(D)Trp—(D)Trp—(D)Thr—NH$_2$ | 36 |
| 103 | (D)Ile—(D)Met—(D)Ser—(D)Trp—(D)Trp—(D)Trp—NH$_2$ | 58 |
| 104 | (D)Ile—(D)Met—(D)Ser—(D)Trp—(D)Trp—(D)Asp—NH$_2$ | 60 |
| 105 | (D)Ile—(D)Met—(D)Ser—(D)Trp—(D)Trp—(D)Glu—NH$_2$ | 64 |
| 106 | (D)Ile—(D)Met—(D)Ser—(D)Trp—(D)Trp—(D)Cys—NH$_2$ | 79 |
| 107 | (D)Ile—(D)Met—(D)Ser—(D)Trp—(D)Trp—(D)Lys—NH$_2$ | 118 |
| 108 | (D)Ile—(D)Met—(D)Ser—(D)Trp—(D)Trp—(D)Phe—NH$_2$ | 153 |

TABLE 5-continued (D)Ile—(D)Met—(D)Ser—(D)Trp—(D)Trp—Xaa—NH$_2$
(SEQ ID NO. 2/5)

| SEQ ID NO. | PEPTIDE | IC$_{50}$ (nM) |
|---|---|---|
| 109 | (D)Ile—(D)Met—(D)Ser—(D)Trp—(D)Trp—(D)Leu—NH$_2$ | 2541 |

TABLE 6

(D)Ile—(D)Met—(D)Ser—(D)Trp—(D)Trp—Gly—Xaa—NH$_2$
(SEQ ID NO NO. 2/6)

| SEQ ID NO. | PEPTIDE | IC$_{50}$ (nM) |
|---|---|---|
| 110 | (D)Ile—(D)Met—(D)Ser—(D)Trp—(D)Trp—Gly—(D)Phe—NH$_2$ | 1 |
| 111 | (D)Ile—(D)Met—(D)Ser—(D)Trp—(D)Trp—Gly—(D)Lys—NH$_2$ | 4 |
| 112 | (D)Ile—(D)Met—(D)Ser—(D)Trp—(D)Trp—Gly—(D)Met—NH$_2$ | 9 |
| 113 | (D)Ile—(D)Met—(D)Ser—(D)Trp—(D)Trp—Gly—(D)Pro—NH$_2$ | 10 |
| 114 | (D)Ile—(D)Met—(D)Ser—(D)Trp—(D)Trp—Gly—(D)Ile—NH$_2$ | 10 |
| 115 | (D)Ile—(D)Met—(D)Ser—(D)Trp—(D)Trp—Gly—(D)Arg—NH$_2$ | 10 |
| 116 | (D)Ile—(D)Met—(D)Ser—(D)Trp—(D)Trp—Gly—(D)His—NH$_2$ | 10 |
| 117 | (D)Ile—(D)Met—(D)Ser—(D)Trp—(D)Trp—Gly—(D)Tyr—NH$_2$ | 13 |
| 118 | (D)Ile—(D)Met—(D)Ser—(D)Trp—(D)Trp—Gly—(D)Thr—NH$_2$ | 14 |
| 119 | (D)Ile—(D)Met—(D)Ser—(D)Trp—(D)Trp—Gly—Gly—NH$_2$ | 14 |
| 120 | (D)Ile—(D)Met—(D)Ser—(D)Trp—(D)Trp—Gly—(D)Ser—NH$_2$ | 14 |
| 121 | (D)Ile—(D)Met—(D)Ser—(D)Trp—(D)Trp—Gly—(D)Trp—NH$_2$ | 15 |
| 122 | (D)Ile—(D)Met—(D)Ser—(D)Trp—(D)Trp—Gly—(D)Leu—NH$_2$ | 18 |
| 123 | (D)Ile—(D)Met—(D)Ser—(D)Trp—(D)Trp—Gly—(D)Ala—NH$_2$ | 18 |
| 124 | (D)Ile—(D)Met—(D)Ser—(D)Trp—(D)Trp—Gly—(D)Asn—NH$_2$ | 18 |
| 125 | (D)Ile—(D)Met—(D)Ser—(D)Trp—(D)Trp—Gly—(D)Val—NH$_2$ | 18 |
| 126 | (D)Ile—(D)Met—(D)Ser—(D)Trp—(D)Trp—Gly—(D)Gln—NH$_2$ | 20 |
| 127 | (D)Ile—(D)Met—(D)Ser—(D)Trp—(D)Trp—Gly—(D)Glu—NH$_2$ | 78 |
| 128 | (D)Ile—(D)Met—(D)Ser—(D)Trp—(D)Trp—Gly—(D)Cys—NH$_2$ | 94 |
| 129 | (D)Ile—(D)Met—(D)Ser—(D)Trp—(D)Trp—Gly—(D)Asp—NH$_2$ | 97 |

Table 7 provides the IC$_{50}$ values of the opioid peptides identified as inhibitors which are within the general formula (D)Ile-(D)Met-(D)Thr-(D)-Trp-Gly-Xaa—NH$_2$ (SEQ ID NO. 7), wherein Xaa is Gly or the D-form of a naturally occurring amino acid.

TABLE 7

(D)Ile—(D)Met—(D)Thr—(D)Trp—Gly—Xaa—NH$_2$
(SEQ ID NO. 7)

| SEQ ID NO. | PEPTIDE | IC$_{50}$ (nM) |
|---|---|---|
| 130 | (D)Ile—(D)Met—(D)Thr—(D)Trp—Gly—(D)Pro—NH$_2$ | 15 |
| 131 | (D)Ile—(D)Met—(D)Thr—(D)Trp—Gly—(D)Tyr—NH$_2$ | 16 |
| 132 | (D)Ile—(D)Met—(D)Thr—(D)Trp—Gly—(D)Phe—NH$_2$ | 27 |
| 133 | (D)Ile—(D)Met—(D)Thr—(D)Trp—Gly—(D)Met—NH$_2$ | 35 |
| 134 | (D)Ile—(D)Met—(D)Thr—(D)Trp—Gly—(D)Trp—NH$_2$ | 37 |
| 135 | (D)Ile—(D)Met—(D)Thr—(D)Trp—Gly—(D)Ile—NH$_2$ | 38 |
| 136 | (D)Ile—(D)Met—(D)Thr—(D)Trp—Gly—(D)Ala—NH$_2$ | 45 |
| 137 | (D)Ile—(D)Met—(D)Thr—(D)Trp—Gly—(D)Leu—NH$_2$ | 49 |
| 138 | (D)Ile—(D)Met—(D)Thr—(D)Trp—Gly—Gly—NH$_2$ | 58 |
| 139 | (D)Ile—(D)Met—(D)Thr—(D)Trp—Gly—(D)Cys—NH$_2$ | 58 |
| 140 | (D)Ile—(D)Met—(D)Thr—(D)Trp—Gly—(D)Val—NH$_2$ | 71 |
| 141 | (D)Ile—(D)Met—(D)Thr—(D)Trp—Gly—(D)His—NH$_2$ | 86 |
| 142 | (D)Ile—(D)Met—(D)Thr—(D)Trp—Gly—(D)Ser—NH$_2$ | 87 |
| 143 | (D)Ile—(D)Met—(D)Thr—(D)Trp—Gly—(D)Arg—NH$_2$ | 97 |
| 144 | (D)Ile—(D)Met—(D)Thr—(D)Trp—Gly—(D)Lys—NH$_2$ | 107 |
| 145 | (D)Ile—(D)Met—(D)Thr—(D)Trp—Gly—(D)Asn—NH$_2$ | 109 |
| 146 | (D)Ile—(D)Met—(D)Thr—(D)Trp—Gly—(D)Thr—NH$_2$ | 130 |
| 147 | (D)Ile—(D)Met—(D)Thr—(D)Trp—Gly—(D)Gln—NH$_2$ | 139 |

TABLE 7-continued

(D)Ile—(D)Met—(D)Thr—(D)Trp—Gly—Xaa—NH$_2$
(SEQ ID NO. 7)

| SEQ ID NO. | PEPTIDE | IC$_{50}$ (nM) |
| --- | --- | --- |
| 148 | (D)Ile—(D)Met—(D)Thr—(D)Trp—Gly—(D)Asp—NH$_2$ | 1709 |
| 149 | (D)Ile—(D)Met—(D)Thr—(D)Trp—Gly—(D)Glu—NH$_2$ | 1959 |

Identified from a positional scanning synthetic combinatorial library (PS-SCL) are the peptides of Table 8 which have the generic formula Tyr-A1-B2-C3—NH2 (SEQ. ID No. 8), wherein A1 is (D)Nve or (D)Nle, B2 is Gly, Phe, or Trp, and C3 is Trp or Nap. IC$_{50}$ values for each of the peptides in the µ selective radioreceptor assay are provided below.

TABLE 8

Tyr—A1—B2—C3—NH$_2$
(SEQ ID NO. 214)

| SEQ ID NO. | PEPTIDE | IC$_{50}$ (nM) |
| --- | --- | --- |
| 150 | Tyr—(D)Nve—Gly—Nap—NH$_2$ | 0.2 |
| 151 | Tyr—(D)Nle—Gly—Nap—NH$_2$ | 1 |
| 152 | Tyr—(D)Nve—Gly—Trp—NH$_2$ | 3 |
| 153 | Tyr—(D)Nle—Gly—Trp—NH$_2$ | 5 |
| 154 | Tyr—(D)Nve—Phe—Trp—NH$_2$ | 5 |
| 155 | Tyr—(D)Nve—Trp—Nap—NH$_2$ | 5 |
| 156 | Tyr—(D)Nve—Trp—Trp—NH$_2$ | 5 |
| 157 | Tyr—(D)Nve—Phe—Nap—NH$_2$ | 7 |
| 158 | Tyr—(D)Nle—Phe—Trp—NH$_2$ | 15 |
| 159 | Tyr—(D)Nle—Trp—Trp—NH$_2$ | 17 |
| 160 | Tyr—(D)Nle—Phe—Nap—NH$_2$ | 30 |
| 161 | Tyr—(D)Nle—Trp—Nap—NH$_2$ | 32 |

Synthesis of Tyr-Tyr, Tyr-Tyr-Phe, and Tyr-Tyr-Phe-Pro (SEQ ID NO. 217) Related Compounds Specific compounds for receptor binding studies were synthesized. The protected tetrapeptide resin YYFP-MBHA and the tripeptide resin YYF-MBHA were permethylated, perethylated, perallylated, perbenzylated and pernaphthylated in their trityl protected form to obtain, after trityl deprotection, the free N-terminal amino groups. Furthermore these peptide resins were also modified by reductive alkylation prior to permethylation and perallylation. Reductive alkylation was performed using the dimethoxydityl-protected peptide resins to obtain the monomethylated N-terminal amine and the free amine to obtain the dimethylated N-terminal amine. One series of these twenty peptides (including one non alkylated peptide sequence as a control) was cleaved from the resin after peralkylation—one series was reduced after peralkylation. Synthetic details are given below for the representative example Pm and red[MeHN-YYF—NH$_2$.

Materials

Amino acid derivatives were purchased from Bachem California (Torrance, Calif.). p-Methylbenzhydrylamine resin (MBHA), 1% DVB, 100–200 mesh, 0.9 meq./g substitution, was received from Peninsula Laboratories, INC (Belmont, Calif.). Anhydrous THF, anhydrous DMSO and lithium tert. butoxide as a 1M solution in THF were purchased from Aldrich (Milwaukee, Wis.). Other solvents were obtained from Fisher (Fair Lawn, N.J.).

Synthesis of the protected peptide resin, Trt-Tyr (2, 6-di-Cl-Bzl)-Tyr(2,6-di-Cl-Bzl)-Phe-MBHA resin.

The peptide starting material was synthesized using standard Boc chemistry and simultaneous multiple peptide synthesis starting with 100 mg MBHA resin (0.09 mmol amino groups) contained in a polypropylene mesh packet.

Coupling of Triphenylmethyl chloride (Trityl chloride, TrtCl)

The Tyr(2,6-di-Cl-Bzl)-Tyr(2,6-di-Cl-Bzl)-Phe-MBHA resin (0.09 mmol primary amino groups) was washed with DCM (1×1 min×5 ml), 5% DIEA/DCM (3×2 min×5 ml) and DCM (2×1 min×5 ml). 5.84 ml DMF/DCM (9:1) and 0.455 ml DIEA (2.61 mmol) were added to the peptide-resin, followed by addition of 125.45 mg TrtCl (0.45 mmol). The reaction mixture was shaken for 6 hr. The peptide resin was washed with DCM (1×1 min×5 ml), 5% DIEA/DCM (1×1 min×5 ml) and/DCM (1×1 min×5 ml). The coupling was repeated for 2 hr using 9 ml DCM as the solvent and the same amounts of DIEA and TrtCl as used for the first coupling. The peptide-resin was washed with DMF (2×1 min×5 ml), 5% DIEA/DCM (1×2 min×5 ml), DCM (3×1 min×5 ml) and MeOH (1×1 min×5 ml). A small sample of peptide-resin was tested for the completeness of the coupling using the bromophenol blue test (Krchnak et al., Collect. Czech, Chem. Commun. 53: 2542–2548 (1988)).

Peralkylation of the resin-bound protected peptide

All manipulations were performed under nitrogen atmosphere and strictly anhydrous conditions. The peptide-resin was dried overnight at 50 mTorr. 10.8 ml 0.5M Lithium tert. butoxide in THF (5.4 mmol) was added to the Trt-Tyr (2,6-di-Cl-Bzl)-Tyr(2,6-die-Cl-Bzl)-Phe-MBHA resin packet (0.09 mmol peptide, 0.27 mmol amide groups) and shaken at room temperature for 15 min. The excess base solution was removed using a positive nitrogen pressure syphon. 10.8 ml DMSO and 1.008 ml iodomethane (16.2 mmol) were added. The reaction mixture was shaken at room temperature for 2 hr. The alkylation solution was removed by positive nitrogen pressure syphon transfer and the entire procedure repeated twice. The resin packet was washed with DMF (3×1 min×5 ml), IPA (2×1 min×5 ml), DCM (3×1 min×5 ml) and MeOH (1×1 min×5 ml).

Deprotection of Trityl protecting group

The peptide-resin was washed with DCM (1×1 min×t ml) and then treated with 2% TFA in DCM (1×2 min×5 ml and 1×30 min×5 ml), followed by the 1 min. washing steps DCM (1×5 ml), IPA (2×5 ml) and DCM (2×5 ml).

Reductive methylation of 4, 4'-dimethoxydityl (Dod) protected unmodified or permethylated peptides (Kaljuste and Unden, Int. J. Peptide Protein Res. 42:118–124 (1993)).

Coupling of 4.4'-dimethoxydityl chloride (DodCl)

The Tyr(2,6-di-Cl-Bzl)-(NMe)-Tyr(2,6-di-Cl-Bzl)-(NMe)-Phe-(NMe) MBHA resin packet (0.09 mmol primary amine) was washed with DCM (1×1 min×5 ml), 5% DIEA/DCM (3×2 min×5 ml) and DCM (2×1 minx t ml). 22.5 ml DCM and 0.455 ml DIEA (2.61 mmol) were added to the resin packet, followed by addition of 118.17 mg of DodCl (0.45 mmol). The mixture was shaken for 90 min. The resin packet was washed with DMF (2×1 min×5 ml), 5% DIEA/DCM (1×2 min×5 ml) and DCM (3×1 min×5 ml). A sample of the resin was tested for the completeness of the coupling using the bromophenol blue test.

Preparation of the formaldehyde solution 10 ml formaldehyde (37% wt solution in water), 90 ml DMF and 30 g of anhydrous magnesium sulfate were mixed and shaken 24 hr, centrifuged, and then the supernatant used for the reductive methylation.

Reductive methylation 10.8 ml formaldehyde solution were added to Dod-Tyr(2,6-di-Cl-Bzl)-(NMe)-Tyr(2,6-di-Cl-Bzl)-(NMe)-Phe-(NMe)MBHA resin packet (0.09 mmol peptide) and shaken for 5 min. The solution was poured off. Additional 10.8 ml formaldehyde solution with 0.108 ml acetic acid were added and shaken. After 5 min, 108 mg of sodium cyanoborohydride was added and the mixture shaken for 1 hr. The resin packet was washed with DMF (2×1 min×5 ml), IPA (2×1 min×5 ml), DCM (3×1 min×5 ml) and MeOH (1×1 min×5 ml).

Deprotection of the Dod protecting group (occasionally)

The resin packet was washed with DCM (1×1 min×5 ml), then treated with 55% TRA in DCM (1×5 min×5 ml and 1×30 min×5 ml), followed by the 1 min washing steps DCM (1×5 ml, IPA (2×5 ml) and DCM (2×1 min).

Reduction

Into a 50 ml glass tube (teflon-lined cap) were added the Dod-(NMe)-Tyr(2,6-di-Cl-Bzl)-(NMe)-Tyr(2,6-di-Cl-Bzl)-(Nme)-Phe-(NMe)MBHA resin packet and 310 mg boric acid (5.014 mmol). Under nitrogen atmosphere, 0.5 ml trimethylborate (0.0042 mmol) were added, followed by the addition of 15 ml of 1M borane-tetrahydrofurane complex (15 mmol). Following cessation of hydrogen evolution, the tube was sealed and placed in a controlled temperature oven at 65° for 100 hr. The tubes were then removed, cooled to room temperature and 2 ml methanol were added to quench excess reducing agent. The resin packet was washed with THF (1×1 min×10 ml) and MeOH (4×1 min×10 ml). After drying the resin packet, it was covered with 15 ml piperidine and heated at 65° C. for 18 hr. The resin packet was washed with DMF (2×1 minx 5 ml), DCM (2×1 min×5 ml), MeOH (1×1 min×5 ml), DMF (2×1 min×5 ml), DCM (2×1 min×5 ml) and MeOH (1×1 min×5 ml).

Release from the solid support

The resin packet was cleaved with hydrogen fluoride (5 ml with 0.35 ml anisole added as scavenger) using a multiple vessel cleavage apparatus for 9 hr at 0° C. (Houghten et al., *Int. J. Pept. Protein Res.*, 27:673–678 (1986)). The resulting polyamine was extracted using 50% aqueous acetonitrile (3×5 ml) following sonication. The solution was lyophilized, taken up twice more in 50% aqueous acetonitrile and lyophilized yielding the crude product 2.

TABLE 9

| SEQ ID NO. | PEPTIDE | IC$_{50}$ (nM) |
|---|---|---|
| 162 | Pm and red {Me$_2$N—Tyr—Tyr—Phe—NH$_2$} | 1 |
| 163 | Pm and red {MeHN—Tyr—Tyr—Phe—NH$_2$} | 88 |
| 164 | Pm and red {NH$_2$—Tyr—Tyr—Phe—NH$_2$} | 14 |
| 165 | Pa and red {Me$_2$N—Tyr—Tyr—Phe—NH$_2$} | 181 |
| 166 | Pa and red {MeHN—Tyr—Tyr—Phe—NH$_2$} | 178 |
| 167 | Pa and red {NH$_2$—Tyr—Tyr—Phe—NH$_2$} | 244 |
| 168 | Pe and red {NH$_2$—Tyr—Tyr—Phe—NH$_2$} | 409 |
| 169 | Pb and red {NH$_2$—Tyr—Tyr—Phe—NH$_2$} | 4906 |
| 170 | Pn and red {NH$_2$—Tyr—Tyr—Phe—NH$_2$} | 7466 |
| 171 | Pm {Me$_2$N—Tyr—Tyr—Phe—NH$_2$} | 5857 |
| 172 | Pm {MeHN—Tyr—Tyr—Phe—NH$_2$} | 6244 |
| 173 | Pm {NH$_2$—Tyr—Tyr—Phe—NH$_2$} | 288 |
| 174 | Pa {Me$_2$N—Tyr—Tyr—Phe—NH$_2$} | 10953 |
| 175 | Pa {MeHN—Tyr—Tyr—Phe—NH$_2$} | 27064 |
| 176 | Pa {NH$_2$—Tyr—Tyr—Phe—NH$_2$} | 21923 |
| 177 | Pe {NH$_2$—Tyr—Tyr—Phe—NH$_2$} | 11025 |
| 178 | Pb {NH$_2$—Tyr—Tyr—Phe—NH$_2$} | 26937 |
| 179 | Pn {NH$_2$—Tyr—Tyr—Phe—NH$_2$} | 24014 |
| 180 | Pm and red {Me$_2$N—Tyr—Tyr—Phe—Pro—NH$_2$} | 8 |
| 181 | Pm and red {MeNH—Tyr—Tyr—Phe—Pro—NH$_2$} | 2 |
| 182 | Pm and red {NH$_2$—Tyr—Tyr—Phe—Pro—NH$_2$} | 13 |
| 183 | Pa and red {Me$_2$N—Tyr—Tyr—Phe—Pro—NH$_2$} | 69 |
| 184 | Pa and red {MeHN—Tyr—Tyr—Phe—Pro—NH$_2$} | 51 |
| 185 | Pa and red {NH$_2$—Tyr—Tyr—Phe—Pro—NH$_2$} | 66 |
| 186 | Pe and red {NH$_2$—Tyr—Tyr—Phe—Pro—NH$_2$} | 45 |
| 187 | Pb and red {NH$_2$—Tyr—Tyr—Phe—Pro—NH$_2$} | 4464 |
| 188 | Pn and red {NH$_2$—Tyr—Tyr—Phe—Pro—NH$_2$} | 18589 |
| 189 | Pm {Me$_2$N—Tyr—Tyr—Phe—Pro—NH$_2$} | 5857 |
| 190 | Pm {MeHN—Tyr—Tyr—Phe—Pro—NH$_2$} | 6244 |
| 191 | Pm {NH$_2$—Tyr—Tyr—Phe—Pro—NH$_2$} | 2014 |
| 192 | Pa {Me$_2$N—Tyr—Tyr—Phe—Pro—NH$_2$} | 21524 |
| 193 | Pa {MeHN—Tyr—Tyr—Phe—Pro—NH$_2$} | 10047 |
| 194 | Pa {NH$_2$—Tyr—Tyr—Phe—Pro—NH$_2$} | 21923 |
| 195 | Pe {NH$_2$—Tyr—Tyr—Phe—Pro—NH$_2$} | 11025 |
| 196 | Pb {NH$_2$—Tyr—Tyr—Phe—Pro—NH$_2$} | 26937 |
| 197 | Pn {NH$_2$—Tyr—Tyr—Phe—Pro—NH$_2$} | 24014 |
| 198 | Pm and red {Me$_2$N—Tyr—Tyr—NH$_2$} | 194 |
| 199 | Pm and red {MeHN—Tyr—Tyr—NH$_2$} | 80 |
| 200 | Pm and red {H$_2$N—Tyr—Tyr—NH$_2$} | 4143 |
| 201 | red {Me$_2$N—Tyr—(NMe)—Tyr—(NHBzl)—NH$_2$} | 34 |

TABLE 9-continued

| SEQ ID NO. | PEPTIDE | IC$_{50}$ (nM) |
|---|---|---|
| 202 | red {MeHN—Tyr—(NMe)—Tyr—(NHBzl)—NH$_2$} | 2 |
| 203 | red {H$_2$N—Tyr—(NMe)—Tyr—(NHBzl)—NH$_2$} | 8 |
| 204 | red {Me$_2$N—Tyr—(NHBzl)—Tyr—(NHMe)—NH$_2$} | 1143 |
| 205 | red {MeHN—Tyr—(NHBzl)—Tyr—(NHMe)—NH$_2$} | 1047 |
| 206 | red {H$_2$N—Tyr—(NHBzl)—Tyr—(NHMe)—NH$_2$} | 739 |
| 207 | Pm and red {Me$_2$N—Tyr—Tyr—(D)Phe—NH$_2$} | 38 |
| 208 | Pm and red {Me$_2$N—Tyr—(D)Tyr—Phe—NH$_2$} | 352 |
| 209 | Pm and red {Me$_2$N—(D)Tyr—Tyr—Phe—NH$_2$} | 687 |
| 210 | Pm and red {Me$_2$N—(D)Tyr—(D)Tyr—(D)Phe—NH$_2$} | 866 |
| 211 | Pm and red {Me$_2$N—(D)Tyr—(D)Tyr—Phe—NH$_2$} | 1554 |
| 212 | Pm and red {Me$_2$N—Tyr—(D)Tyr—(D)Phe—NH$_2$} | 908 |
| 213 | Pm and red {Me$_2$N—(D)Tyr—Tyr—(D)Phe—NH$_2$} | 993 |

EXAMPLE II

Mu Receptor Specificity Of Opioid Peptides

This example demonstrates the specificity of the novel opioid peptides for the B receptors as compared to the δ and κ opiate receptors.

Individual peptides were synthesized and the activity of these peptides in the radioreceptor assay selective for the μ receptors from Example I were compared to radioreceptor assays selective for the δ and κ receptors as detailed below.

Individual peptides were synthesized using simultaneous multiple peptide synthesis (SMPS) and their identities confirmed by mass spectral analysis on a MALDI instrument from Kratos Analytical (Ramsey, N.J.). Peptides were purified by reversed-phase high performance liquid chromatography using a Waters Milliprep 300 preparative HPLC (Milford, Mass.) modified with a Gilson Model 232 preparative autosampler and Foxy fraction collector (Gilson Medical Electronics, Middleton, Wis.). Pure fractions (determined using analytical HPLC) were pooled and lyophilized.

Radioreceptor assays selective for δ receptors were performed using rat brain homogenates as above and [$^3$H]-naltrindole (0.5 nM, specific activity 34.7 Ci/mmol) as radioligand in Tris buffer containing 100 μM phenylmethylsulfonyl fluoride (PMSF), 5 mMMgCl$_2$ and 1 mg/ml bovine serum albumin (BSA), pH 7.4. Samples were incubated for 2.5 hr. Standard curves were prepared using 0.10–3200 nM [$^3$H]-D-Pen$_2$, Pen$_5$]-enkephalin ([$^3$H]-DPDPE).

Assays selective for κ receptors were carried out using [$^3$H]-U69,593 (3 nM, specific activity 62 Ci/mmol) as the radioligand and tissue homogenates prepared from guinea pig brains (cortex and cerebellum) using Tris buffer containing 100 μM PMSF, 5 mMMgCl$_2$ and 1 mg/ml BSA, pH 7.4. Sample tubes were incubated for 2.5 hr. Standard curves were prepared using 0.05–6300 nM naloxone.

Tritiated ligands, [$^3$H]-DAMGO, [$^3$H]-DPDPE and [$^3$H]-[D-Ser$^2$, Leu$^5$, Thr$^6$]enkephalin ([$^3$H]-DSLET), Abuse (NIDA) repository, as prepared by Multiple Peptide Systems (San Diego, Calif.), [$^3$H]-U69,593 from Amersham (Arlington Heights, Ill.) and [$^3$H]-naltrindole from DuPont NEN Research Products (Los Angeles, Calif.). The average standard deviation for IC$_{50}$ values was ±20%.

TABLE 10

| PEPTIDE | SEQ ID NO. | μ IC$_{50}$ (nM) | δ IC$_{50}$ (nM) | κ IC$_{50}$ (nM) | δ/μ | κ/μ |
|---|---|---|---|---|---|---|
| YPFGFR—NH$_2$ | 70 | 13 | 26,500 | 5,050 | 2,040 | 388 |
| YPFGFG—NH$_2$ | 71 | 18 | 18,300 | 38,600 | 1,010 | 2,150 |
| YPFGFK—NH$_2$ | 72 | 19 | 69,800 | 10,400 | 3,670 | 549 |
| YPFGFS—NH$_2$ | 73 | 24 | 38,800 | 69,100 | 1,620 | 2,880 |
| WWPKHG—NH$_2$ | 48 | 9 | 7,660 | 81,100 | 851 | 9,010 |
| WWPKHN—NH$_2$ | 49 | 11 | 42,600 | 70,700 | 3,880 | 6,430 |
| WWPKHK—NH$_2$ | 50 | 13 | 90,600 | 33,200 | 6,970 | 2,560 |
| WWPKHH—NH$_2$ | 51 | 14 | 53,900 | 66,900 | 3,850 | 4,780 |
| WWPK—NH$_s$ | 68 | 17 | 35,000 | 80,000 | 2,060 | 4,700 |
| WWPR—NH$_2$ | 6 | 10 | 17,400 | 20,600 | 1,740 | 2,060 |
| Ac—RWIGWR—NH$_2$ | 28 | 5 | 1,670 | 502 | 330 | 100 |
| Ac—RWIGWK—NH$_2$ | 29 | 35 | 5,620 | 4,240 | 160 | 121 |
| Ac—RWIGWT—NH$_2$ | 30 | 51 | 6,120 | 21,200 | 120 | 415 |
| Ac—RWIGWM—NH$_2$ | 31 | 175 | 2,900 | 20,800 | 17 | 119 |
| Ac—FRWWYM—NH$_2$ | 8 | 33 | 940 | 28,700 | 28 | 870 |
| Ac—FRWWYL—NH$_2$ | 9 | 35 | 1,540 | 21,000 | 44 | 600 |
| Ac—FRWWYI—NH$_2$ | 12 | 64 | 193 | 99,400 | 3 | 1,550 |
| Ac—FRWWYG—NH$_2$ | 15 | 78 | 303 | 8,720 | 4 | 112 |
| Y—(D)Nve—G—Nap—NH$_2$ | 150 | 0.2 | 11 | 203 | 55 | 1015 |
| Y—(D)Nle—G— | 151 | 1 | 24 | 1178 | 24 | 1178 |

TABLE 10-continued

| PEPTIDE | SEQ ID NO. | μ IC$_{50}$ (nM) | δ IC$_{50}$ (nM) | κ IC$_{50}$ (nM) | δ/μ | κ/μ |
|---|---|---|---|---|---|---|
| Nap—NH$_2$ | | | | | | |
| Y(D)NveGW—NH$_2$ | 152 | 3 | 199 | 1701 | 66 | 567 |
| Y(D)NleGW—NH$_2$ | 153 | 5 | 220 | 2250 | 44 | 450 |
| Y(D)NveFW—NH$_2$ | 154 | 5 | 127 | 228 | 25 | 46 |
| Y—(D)Nve—W—Nap—NH$_2$ | 155 | 5 | 98 | 214 | 20 | 43 |
| Y(D)NveWW—NH$_2$ | 156 | 5 | 282 | 752 | 56 | 150 |
| Y—(D)Nve—F—Nap—NH$_2$ | 157 | 7 | 652 | 1221 | 93 | 174 |
| Y(D)NleFW—NH$_2$ | 158 | 15 | 303 | 816 | 20 | 54 |
| Y(D)NleWW—NH$_2$ | 159 | 17 | 517 | 2045 | 30 | 120 |
| Y—(D)Nle—F—Nap—NH$_2$ | 160 | 30 | 1055 | 1859 | 35 | 62 |
| Y—(D)Nle—W—Nap—NH$_2$ | 161 | 32 | 449 | 1226 | 14 | 38 |
| DAMGO | — | 3 | 758 | 2,530 | 253 | 844 |
| DALDA | — | 14 | 271,800 | 6,800 | 19,400 | 485 |
| YGGFL—OH | 218 | 65 | 41 | 16,700 | 0.7 | 257 |

The above comparative data provided in Table 10 demonstrates the selectivity of the novel opioid peptides for the β receptors over the δ and κ opiate receptors.

EXAMPLE III

Mu Receptor Agonist Or Antagonist Activity By Adenylyl Cyclase Assay

Certain opioid compounds are agonists (bind to the receptor and produce an effect) while others are antagonists (bind to the receptor but do not produce an effect). This example uses the adenylyl cyclase assay to demonstrate that certain of the novel opioid peptides are agonists of the μ receptor while others are antagonists of the μ receptor.

An adenylyl cyclase assay using human SH-SY5Y neuroblastoma cell line membranes was used to rapidly determine the opioid agonists or antagonist properties of individual peptides. Opioid agonist inhibit adenylyl cyclase activity, resulting in reduced levels of cyclic AMP.

Adenylyl Cyclase Assay

The human SH-SY5Y neuroblastoma cell line (Biedler et al., Cancer Research, 38:3751–3757 (1978), which is incorpoated herein by reference), was cultured in RPMI 1640 medium buffered with 12.5 mM HEPES, pH 7.2, and contained 300 μg/ml L-glutamine, 100 U/ml penicillin, 100 μg/ml streptomycin, 50 μM 2-mercaptoethanol, 60 μM 2-ethanolamine and 10% iron-supplemented-bovine calf serum in 5% CO$_2$ at 37° C. Cells were cultured in medium containing 10 μM retinoic acid for six days before harvesting in order to differentiate the cells as previously described (Ya and Sadfe, J. Pharmacol. Exp. Ther., 245:350–355 (1988), which is incorporated herein by reference).

Cell membranes were prepared for use in the adenylyl cyclase assays as previously described (Law et al., Mol. Pharmacol., 23:26–35 (1983), which is herein incorporated by reference). After the initial centrifugation at 200×g for 15 min at 4° C., the cells were resuspended in sucrose buffer (0.32M sucrose, 40 mM HEPES, 2 mMEGTA, pH 7.6). Cells were centrifuged again at 200×g, then homogenized in sucrose buffer with five strokes of a Dounce Homogenizer (Wheaton Instruments, Millville, N.J.). Membranes were centrifuged at 22000×g for 20 min at 4° C., then resuspended in sucrose buffer. The protein concentration was determined by the method of Bradford (Bradford, supra), using BSA as the standard. SH-SY5Y membranes at a protein concentration of 1–4 mg/ml were stored at −80° C.

SH-SY5Y membranes were incubated in a final volume of 100 μl of 40 mM HEPES, pH 7.7, containing 15 units of creatine phosphokinase, 20 mM phosphocreatine, 1 mM 1,10-o-phenanthroline, 60 μM isobutylmethylxanthine (IBMX), 50 μM ATP, 50 μM GTP, 3 mM MgCl$_2$ and 100 mM NaCl. Each of the agonists and antagonists tested were included at final concentrations of 100 μM and 500 μM, respectively. The reaction was initiated by the addition of 36 μg of membrane protein. After 15 min at 30° C., the reaction was stopped by the addition of 100 μl of cold 4.5% perchloric acid. The samples were neutralized by the addition 40 μl of cold 30% potassium bicarbonate. Finally, the membranes were centrifuged at 12000×g for 4 min at 4° C. in a microcentrifuge. The amount of cyclic AMP present in 100 μl of the supernatant, equivalent to the cyclic AMP produced by 15 μg of membrane protein, was determined using a cyclic AMP kit (Diagnostic Products, Los Angeles, Calif.). This procedure, which uses a cyclic AMP binding protein in a competitive protein binding assay, is based on the method of Tovey et al. (Clin. Chim. Acts, 56:221–234), which is incorporated herein by reference), and was used with the following modification: [$^3$H]-cyclic AMP (specific activity 31.4 Ci/mmol), obtained from Amersham (Arlington Heights, Ill.), was used instead of the [$^3$H]-cyclic AMP included in the assay kit. [$^3$H]-cyclic AMP, 0.9 μCi, was added into 6 ml of H$_2$O, and 100 μl of the diluted [$^3$H]-cyclic AMP was added to the assay tubes. The final supernatants were counted in 10 ml of Ecolite (+) scintillation fluid (ICN Pharmaceuticals, Covina, Calif.).

A reduction of cyclic AMP levels to less than 70% the basal cyclic AMP levels was regarded as being indicative of an opioid agonist effect, provided that the inhibition of cyclic AMP was blocked by the opioid antagonist naloxone. Table 11 provides the results of the adenylyl cyclase assay and indicates which of the tested peptides are μ receptor agonists and which are μ receptor antagonists.

TABLE 11

ADENYLYL CYCLASE ASSAY FOR MU RECEPTOR AGONIST OR ANTAGONIST ACTIVITY

| | SEQ ID NO. | % Basal Control | | |
|---|---|---|---|---|
| AGONISTS | | | + Naloxone | + ICI 174,864 |
| YPFGFR—NH$_2$ | 70 | 53 ± 3 | 77 ± 8 | 28 ± 3 |
| WWPKHN—NH$_2$ | 49 | 43 ± 10 | 92 ± 3 | 26 ± 3 |
| WWPKHG—NH$_2$ | 48 | 35 ± 4 | 80 ± 0.6 | 32 ± 2 |
| WWPK—NH$_2$ | 68 | 47 ± 8 | 101 ± 2 | 36 ± 5 |
| WWPR—NH$_2$ | 69 | 35 ± 3 | 91 ± 3 | 34 ± 3 |
| Ac—FRWWYM—NH$_2$ | 8 | 46 ± 1 | 70 ± 2 | 30 ± 0.3 |
| DAMGO (100 µM) | — | 34 ± 6 | 77 ± 1 | 28 ± 3 |
| ANTAGONISTS | | | + Naloxone | + ICI 174,864 |
| Ac—RWIGWR—NH$_2$ | 28 | 105 ± 12 | | |
| DAMGO (1 µM) | — | 61 ± 5 | 101 ± 4 | 95 ± 3 |

EXAMPLE IV

Mu Receptor Agonist Or Antagonist Activity By Guinea-Pig Ileum And Mouse Vas Deferens Assays This example demonstrates by guinea-pig ileum and mouse vas deferens assays that certain of the novel opioid peptides are agonists of the receptor while others are antagonists.

Guinea-Pig Ileum Assay

The guinea-pig ileum (GPI) bioassay was carried out to determine whether a peptide is an opioid agonist (binds to receptor and initiates intracellular signal) or an opioid antagonist (binds to receptor but does not initiate an intracellular signal). Such information cannot be determined from the above-described radioreceptor binding assay.

The GPI assay (Kosterlitz et al., Br. J. Pharam. 39:398–418 (1970), which is incorporated herein by reference), is one of the most widely used assays for the determination of opioid activities in vitro. The assay is based on the ability of opioid agonists to inhibit electrically stimulated contraction in tissue. GPI is not a "clean" assay insofar as the ileum preparation contains both µ and κ receptors. However, µ receptor mediated-effects in the GPI can be distinguished from κ receptor mediated effects by determining K$_e$ values for naloxone as the antagonist (µ effects: K$_e$~1–3 nM); κ effects: K$_e$~20–30 nM) or by using specific µ or κ antagonists.

The guinea pigs were killed by decapitation. The ileum was removed and longitudinal muscle-myenteric plexus preparations were placed in Krebs solution (NaCl 118 mM, KCL 4.75 mM, NaH$_2$PO$_4$ 1 mM, NarCO$_3$ 25 mM, MgSO$_4$ 1.2 mM, glucose 11 mM and CaCl$_2$ 2.5 mM). The solution was gassed with 95% O$_2$ and 5% CO$_2$ and maintained at 37° C. The tissue was suspended under a final tension of 1 g in a 10 ml organ bath and stabilized for 1 hr. Electrical stimulation via a straight platinum electrode was applied, 0.4 ms pulses of supramaximal voltage, delivered at a rate of 0.1 Hz. Isometric contractions were measured via strain gauge force transducers and recorded on stripchart recorders.

Mouse Vas Deferens Assay

The mouse vas deferens (MVD) bioassay was also used to determine whether a peptide is an opioid agonist or an opiod antagonist. Again, such information is not available from the radioreceptor binding assay results.

The MVD assay (Henderson et al., Br. J. Pharma. 12:119–127 (1957), which is incorporated herein by reference) is another one of the most widely used assays for the determination of opioid activities in vitro. This assay, like the GPI assay, is based on the ability of opioid agonists to inhibit electrically stimulated contractions in tissue. The MVD assay is also not "clean" in that, in addition to the predominant δ receptor, the µ and κ receptors are also present. However, the use of a specific δ antagonist, such a H-Tyr-Tic-Phe-Phe—NH$_2$ (SEQ ID NO. ) (TIPP) permits an assessment as to whether or not an agonist effect observed in the MVD assay is indeed δ receptor mediated.

Mouse vasa deferentia were dissected and placed in Krebs solution. The responses of the longitudinal muscle were recorded under a basal tension of 0.5 g and excited by pulses of 1 millisecond duration.

In all bioassays, a dose-response curve with a reference compound (e.g., [D-Ala$^2$, Leu$^5$]enkephelinamide or U50, 488) is used in each preparation. This is important, since IC$_{50}$ values of a given compound can vary considerably from one preparation to another. Potencies of new compounds to be tested are determined relative to that of the reference compound, and their IC$_{50}$ values are normalized based on an average IC$_{50}$ value which has been obtained for the reference compound by performance of many determinations with a large number of preparations. In cases where peptides might be susceptible to enzymatic degradation, potencies are determined in the presence of a mixture of peptidase inhibitors (1-1eucyl-leucine, 2 mM; Bestatin, 10–30 µM; thiorphan, 0.3 µM; captopril, 10 µM), as recommended by McKnight et al., Eur. J. Pharm. 86:339–402 (1983). K$_e$ values for naloxone or other antagonists are determined from the ratio of IC$_{50}$ values (DR) obtained with the peptide under investigation in the presence and absence of a fixed concentration of the antagonist, using the formula K$_e$=a/(DR−1) ("a"=fixed concentration). A log dose-response curve is obtained with [Leu$^5$]enkephalin for each ileum and vas deferens preparation and the IC$_{50}$ value is determined. K$_e$ values for antagonists are determined from the ratio of IC$_{50}$ values obtained with [Leu$^5$]enkephalin in the presence and absence of a fixed antagonist concentration.

A log dose-response curve was obtained with [Leu$^5$] enkephalin for each ileum and vas preparation and the IC$_{50}$ value determined. K$_e$ values for antagonists were determined from the ratio of IC$_{50}$ values obtained with [Leu$^5$] enkephalin in the presence and absence of a fixed antagonist concentration of naloxone (Kosterlitz and Watt, Br. J. Pharamcol., 33:266–276 (1968), which is incorporated herein by reference).

Table 12 provides the results of two peptides, WWPKHN—NH$_2$ (SEQ ID NO. 49) and WWPKHK—NH$_2$ (SEQ ID NO. 50) tested in the GPI and MVP assays. These peptides were shown to be agonists in both assays. Their potencies were similar to that of leucine-enkephalin (YGGFL—OH) (SEQ ID NO. 218) in the GPI assay. The agonist effects of WWPKHN—NH$_2$ (SEQ ID NO. 49) and WWPKHK—NH$_2$ (SEQ ID NO. 50) in the GPI assay were antagonized by naloxone with K$_e$ values of 1.27±0.16 nM and 2.97±0.43 nM, respectively, indicating that they were µ receptor-mediated. While the IC$_{50}$ values in the MVD assay were much lower than those of the GPI assay, the MVD assay as discussed above, is predominantly responsive to compounds acting on the δ receptors. Activity in the MVD assay was not antagonized by TIPP, a highly δ-selective antagonist. It was, however, antagonized by naloxone, which preferentially antagonizes µ receptor-mediated effects and therefore, the activity observed in the MVD assay is mediated by the µ receptors presence in the tissue. The activity observed in these assays shows that peptides have potential analgesic activity in vivo.

TABLE 12

AGONIST ACTIVITIES IN THE GUINEA PIG ILEUM (GPI) AND MOUSE VAS DEFERENS (MVP) ASSAYS

| PEPTIDE | SEQ ID NO. | GPI IC$_{50}$ (nM) | MVD IC$_{50}$ (nM) | GPI/MVD ratio |
|---|---|---|---|---|
| WWPKHN—NH$_2$ | 49 | 220 ± 10 | 31 ± 10 | 7.07 |
| WWPKHK—NH$_2$ | 20 | 270 ± 19 | 45 ± 7 | 6.07 |
| YGGFL—OH | 218 | 246 ± 4 | 11 ± 1 | 21.6 |

Additional individual peptides shown to have agonist or antagonist activity either by the adenylyl cyclase assay or the GPI assay are provided in Table 13.

TABLE 13

MU RECEPTOR AGONIST OR ANTAGONIST ACTIVITY

| PEPTIDE | SEQ ID NO. | AGONIST OR ANTAGONIST |
|---|---|---|
| Pm and red {Me$_2$N—Tyr—Tyr—Phe—NH$_2$} | 162 | Antagonist |
| Ac—RFMWMK—NH$_2$ | 219 | Antagonist |
| (D)I—(D)M—(D)S—(D)W—(D)W—G—NH$_2$ | 220 | Agonist |
| (D)I—(D)M—(D)T—(D)W—G—(D)P—NH$_2$ | 15 | Agonist |

Although the invention has been described with reference to the examples provided above, it should be understood that various modifications can be made by those skilled in the art without departing from the invention. Accordingly, the invention is set out in the following claims.

---

We claim:

1. A peptide having the structure:

Ac-Phe-Arg-Trp-Trp-Tyr-Xaa—NH$_2$ (SEQ ID NO. 1), wherein Xaa is a naturally-occurring amino acid.

2. A peptide having the structure:

Ac-Arg-Trp-Ile-Gly-Trp-Xaa—NH$_2$ (SEQ ID NO. 2), wherein Xaa is a naturally-occurring amino acid.

3. A peptide having the structure:

Trp-Trp-Pro-Lys-His-Xaa—NH$_2$ (SEQ ID NO. 3), wherein Xaa is a naturally-occurring amino acid.

4. A peptide having the structure:

Trp-Trp-Pro-Xaa—NH$_2$ (SEQ ID NO. 4);

wherein Xaa is Lys or Arg.

5. A peptide having the structure:

Tyr-Pro-Phe-Gly-Phe-Xaa—NH$_2$ (SEQ ID NO. 5), wherein Xaa is a naturally-occurring amino acid.

6. A peptide having the structure:

(D)Ile-(D)Met-(D)Ser-(D)Trp-(D)Trp-Gly$_n$-Xaa—NH$_2$ (SEQ ID NO. 6), wherein n is 0 or 1 and wherein Xaa is Gly or the D-form-of a naturally-occurring amino acid.

7. A peptide having the structure:

(D)Ile-(D)Met-(D)Thr-(D)Trp-Gly-Xaa—NH$_2$ (SEQ ID NO. 7), wherein Xaa is Gly or the D-form of a naturally-occurring amino acid.

8. A peptide having the structure:

Tyr-A1-B2-C3—NH$_2$ (SEQ ID NO. 214);

wherein A1 is (D)Nve or (D)Nle;
   B2 is Gly, Phe, or Trp; and
   C3 is Trp or Nap.

9. A peptide having the structure:

Pm and red {Me$_x$H$_y$-Tyr-(NMe)$_z$-Tyr-Xaa$_z$—NH$_2$}(SEQ ID NO. 221), wherein
   x is 0, 1, or 2;
   y is 0, 1, or 2; and
   z is 0 or 1; and
   wherein Xaa is Phe, (D)Phe, or NHBzl, with the proviso that x and y together is never greater than 2.

10. A peptide having the structure:

Trp-Trp-Pro-D4-His$_z$-Xaa$_z$—NH$_2$; (SEQ ID NO. 222), wherein z is 0 or 1;
    wherein D4 is Lys or Arg; and
    wherein Xaa is a naturally-occurring amino acid.

* * * * *

UNITED STATES PATENT AND TRADEMARK OFFICE
CERTIFICATE OF CORRECTION

PATENT NO. : 5,641,861
DATED : June 24, 1997
INVENTOR(S) : Dooley et al.

It is certified that error appears in the above-indentified patent and that said Letters Patent is hereby corrected as shown below:

In column 1, before "BACKGROUND OF THE INVENTION" please insert --This invention was made with government support under grant DA09410 awarded by the National Institute on Drug Abuse, National Institutes of Health. The government has certain rights in the invention.--.

In column 10, line 34, please delete "Glyn" and replace therefor with --$Gly_n$--.

In column 10, Table 5, please delete "(SEQ ID NO. 2/5)" and replace therefor with --(SEQ ID NO. 215)--.

In column 10, Table 5-continued, please delete "(SEQ ID NO. 2/5)" and replace therefor with --(SEQ ID NO. 215)--.

In column 11, Table 6, please delete "(SEQ ID NO. 2/6)" and replace therefor with --(SEQ ID NO. 216)--.

In column 13, line 16, please delete "No. 8)" and replace therefor with --No. 214)--.

In column 13, line 58, please insert --]-- after $NH_2$.

In column 14, line 43, please delete "(2,6-die-Cl-Bzl)" and replace therefor with --(2,6-di-Cl-Bzl)--.

In column 14, line 62, please delete "4.4" and replace therefor with --4,4--.

In column 14, line 66, please delete "minx" and replace therefor with --min x--.

UNITED STATES PATENT AND TRADEMARK OFFICE
CERTIFICATE OF CORRECTION

PATENT NO. : 5,641,861
DATED : June 24, 1997
INVENTOR(S) : Dooley et al.

It is certified that error appears in the above-indentified patent and that said Letters Patent is hereby corrected as shown below:

In column 16, line 16, please delete "minx" and replace therefor with --min x--.

In column 17, line 23, please delete "B" and replace therefor with --$\mu$--.

In column 18, line 31, please delete "mMMgCl$_2$" and replace therefor with --mM MgCl$_2$--.

In column 19, line 26, please delete "$\beta$" and replace therefor with --$\mu$--.

In column 19, line 46, please delete the "," (comma) after "reference)", and insert therefor --. The cell line--.

In column 19, line 61, please delete "2 mMEGTA" and replace therefor with --2 mM EDTA--.

In column 21, line 51, please delete "NarCO$_3$" and replace therefor with --NaHCO$_3$--.

In column 21, line 62, please delete "opiod" and replace therefor with --opioid--.

UNITED STATES PATENT AND TRADEMARK OFFICE
CERTIFICATE OF CORRECTION

PATENT NO. : 5,641,861
DATED : June 24, 1997
INVENTOR(S) : Dooley, et. al.

It is certified that error appears in the above-identified patent and that said Letters Patent is hereby corrected as shown below:

In column 23, Table 12, in the column SEQ ID NO. please delete "20" and replace therefor with --50--.

Signed and Sealed this

Twelfth Day of January, 1999

Attest:

Attesting Officer

*Acting Commissioner of Patents and Trademarks*